(12) United States Patent  
Pfleger et al.

(10) Patent No.: US 8,846,354 B1
(45) Date of Patent: Sep. 30, 2014

(54) MICROORGANISMS FOR PRODUCING ORGANIC ACIDS

(71) Applicant: Wisconsin Alumni Research Foundation, Madison, WI (US)

(72) Inventors: Brian Frederick Pfleger, Madison, WI (US); Matthew Brett Begemann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/200,747

(22) Filed: Mar. 7, 2014

Related U.S. Application Data

(63) Continuation-in-part of application No. 13/798,835, filed on Mar. 13, 2013, now Pat. No. 8,715,973.

(60) Provisional application No. 61/647,001, filed on May 15, 2012.

(51) Int. Cl.
  *C12P 7/52* (2006.01)
  *C12P 7/40* (2006.01)
  *C12P 7/56* (2006.01)
  *C12P 7/48* (2006.01)
  *C12P 21/02* (2006.01)
  *A61K 38/00* (2006.01)

(52) U.S. Cl.
  CPC ..................................... *C12P 7/56* (2013.01)
  USPC ........................... 435/141; 435/139; 435/71.2

(58) Field of Classification Search
  None
  See application file for complete search history.

(56) References Cited

U.S. PATENT DOCUMENTS

| | | | |
|---|---|---|---|
| 8,048,624 | B1 | 11/2011 | Lynch |
| 2010/0210017 | A1 | 8/2010 | Gill |
| 2011/0125118 | A1 | 5/2011 | Lynch |
| 2011/0165637 | A1 | 7/2011 | Pfleger et al. |

OTHER PUBLICATIONS

Niederholtmeyer et al. "Engineering Cyanobacteria to Synthesize and Export Hydrophilic Products" Applied and Environmental Microbiology, Jun. 2010, vol. 76, No. 11p. 3462-3466.*
Altschul et al., Basic Local Alignment Search Tool, *J. Mol. Biol.* 1990, 215:403410.
Angermayr et al., Energy biotechnology with cyanobacteria. *Current Opinion in Biotechnology*, 2009, 20(3): p. 257-263.
Ansede et al., Metabolism of Acrylate to beta—Hydroxypropionate and Its Role in Dimethylsulfoniopropionate Lyase Induction by a Salt Marsh Sediment Bacterium, *Alcaligenes faecalis* M3A. *Appl. Environ. Microbiol.*, 1999. 65(11): p. 5075-5081.
Atsumi et al., Direct photosynthetic recycling of carbon dioxide to isobutyraldehyde. *Nat Biotech*, 2009, 27(12): p. 1177-1180.
Balasubramanian et al., Regulatory Roles for IscA and SufA in Iron Homeostasis and Redox Stress Responses in the Cyanobacterium *Synechococcus* sp. Strain PCC 7002. *J. Bacteriol.*, 2006, 188(9): p. 3182-3191.
Bauer, W., Acrylic Acid and Derivatives. *Kirk-Othmer Encyclopedia of Chemical Technology*. 2000: John Wiley & Sons, Inc.
Boynton et al., Intracellular Concentrations of Coenzyme A and Its Derivatives from *Clostridium acetobutylicum* ATCC 824 and Their Roles in Enzyme Regulation. *Appl. Environ. Microbiol.*, 1994, 60(1): p. 39-44.
Bozell et al., Technology development for the production of biobased products from biorefinery carbohydrates—the US Department of Energy's "Top 10" revisited. *Green Chemistry*, 2010, 12(4): p. 539-554.
Cherrington et al., Organic Acids: Chemistry, Antibacterial Activity and Practical Applications, in Advances in Microbial Physiology, A.H. Rose and D.W. Tempest, Editors. 1991, Academic Press. p. 87-108.
Chotani et al., The commercial production of chemicals using pathway engineering. *Biochimica et Biophysica Acta (BBA)—Protein Structure and Molecular Enzymology*, 2000, 1543(2): p. 434-455.
Current Protocols in Molecular Biology, F.M. Ausubel et al., eds., Current Protocols, a joint venture between Greene Publishing Associates, Inc. and John Wiley & Sons, Inc., (supplemented through 2008.
Dacey et al., Hydroxide decomposition of dimethylsulfoniopropionate to form dimethylsulfide. *Geophys. Res. Lett.* 1987, 14:1246-1249.
Ducat et al., Engineering cyanobacteria to generate high-value products. *Trends in Biotechnology*, 2011, 29(2): p. 95-103.
Feist et al., Reconstruction of biochemical networks in microorganisms. *Nat Rev Micro*, 2009, 7(2): p. 129-143.
Fridovich et al., Paraquat and the exacerbation of oxygen toxicity. *Trends in Biochemical Sciences*, 1979, 4(5): p. 113-115.
González et al., Genetics and Molecular Features of Bacterial Dimethylsulfoniopropionate (DMSP) and Dimethylsulfide (DMS) Transformations, in *Handbook of Hydrocarbon and Lipid Microbiology*, K.N. Timmis, Editor. 2010, Springer Berlin Heidelberg. p. 1201-1211.
Green et al., *Molecular Cloning: A laboratory Manual*, 4th ed., Cold Spring Harbor Laboratory Press, 2001.
Hashimoto et al., Nitrile Pathway Involving Acyl-CoA Synthetase. *Journal of Biological Chemistry*, 2005, 280(10): p. 8660-8667.
Henikoff & Henikoff, Amino acid substitution matrices from protein blocks, *Proc. Natl. Acad. Sci. USA*, 1989, 89:10915.

(Continued)

*Primary Examiner* — Manjunath Rao
*Assistant Examiner* — Gerard Lacourciere
(74) *Attorney, Agent, or Firm* — Daniel A. Blasiole; Joseph T. Leone, Esq.; DeWitt Ross & Stevens SC

(57) ABSTRACT

Organic acid-producing microorganisms and methods of using same. The organic acid-producing microorganisms comprise modifications that reduce or ablate AcsA activity or AcsA homolog activity. The modifications increase tolerance of the microorganisms to such organic acids as 3-hydroxypropionic acid, acrylic acid, propionic acid, lactic acid, and others. Further modifications to the microorganisms increase production of such organic acids as 3-hydroxypropionic acid, lactate, and others. Methods of producing such organic acids as 3-hydroxypropionic acid, lactate, and others with the modified microorganisms are provided. Methods of using acsA or homologs thereof as counter-selectable markers are also provided.

20 Claims, 12 Drawing Sheets

(56) References Cited

OTHER PUBLICATIONS

Holo, H., *Chloroflexus aurantiacus* secretes 3-hydroxypropionate, a possible intermediate in the assimilation of $CO^2$ and acetate. *Archives of Microbiology*, 1989, 151(3): p. 252-256.

Horswill et al., Studies of Propionate Toxicity in Salmonella enterica Identify 2-Methylcitrate as a Potent Inhibitor of Cell Growth. *Journal of Biological Chemistry*, 2001, 276(22): p. 19094-19101.

Howard, E.C., et al., *Bacterial Taxa That Limit Sulfur Flux from the Ocean. Science*, 2006. 314(5799): p. 649-652.

Howard et al., Abundant and diverse bacteria involved in DMSP degradation in marine surface waters. *Environmental Microbiology*, 2008, 10(9): p. 2397-2410.

Hugler et al., Malonyl-Coenzyme A Reductase from *Chloroflexus aurantiacus*, a Key Enzyme of the 3-Hydroxypropionate Cycle for Autotrophic $CO_2$ Fixation. J. Bacteriol., 2002, 184(9): p. 2404-2410.

Karlin et al., Application and statistics for multiple high-scoring segments in molecular sequences, *Proc. Natl. Acad. Sci. USA*, 1993, 90:5873-5787.

Kasuya et al. Participation of a medium chain acyl-CoA synthetase in glycine conjugation of the benzoic acid derivatives with the electron-donating groups. *Biochemical Pharmacology*, 1996, 51(6): p. 805-809.

Keasling, J.D., *Manufacturing Molecules Through Metabolic Engineering. Science*, 2010, 330(6009): p. 1355-1358.

Kiene et al., Dimethylsulfoniopropionate and Methanethiol Are Important Precursors of Methionine and Protein-Sulfur in Marine Bacterioplankton. *Appl. Environ. Microbiol.*, 1999, 65(10): p. 4549-4558.

Kumar et al., Development of suitable photobioreactors for $CO_2$ sequestration addressing global warming using green algae and cyanobacteria. *Bioresource Technology*, 2011, 102(8): p. 4945-4953.

Latifi et al., Oxidative stress in cyanobacteria. *FEMS Microbiology Reviews*, 2009, 33(2): p. 258-278.

Lindberg et al. Engineering a platform for photosynthetic isoprene production in cyanobacteria, using Synechocystis as the model organism. *Metabolic Engineering*, 2010, 12(1): p. 70-79.

Liu et al., Fatty acid production in genetically modified cyanobacteria. Proceedings of the National Academy of Sciences, 2011.

Malmstrom et al., Dimethylsulfoniopropionate (DMSP) Assimilation by *Synechococcus* in the Gulf of Mexico and Northwest Atlantic Ocean. *Limnology and Oceanography*, 2005, 50(6): p. 1924-1931.

Man et al., The binding of propionyl-CoA and carboxymethyl-CoA to Escherichia coli citrate synthase. *Biochimica et Biophysica Acta (BBA)—Protein Structure and Molecular Enzymology*, 1995, 1250(1): p. 69-75.

Maruyama et al., Mechanisms of Growth Inhibition by Propionate and Restoration of the Growth by Sodium Bicarbonate or Acetate in *Rhodopseudomonas sphaeroides* S. *Journal of Biochemistry*, 1985, 98(3): p. 819-824.

Nakamura et al, Metabolic engineering for the microbial production of 1,3-propanediol. *Current Opinion in Biotechnology*, 2003, 14(5): p. 454-459.

Needleman et al., A General Method Applicable to the Search for Similarities in the Amino Acid Sequence of Two Proteins, *J. Mol. Biol.* 1970, 48:443.

Niederholtmeyer et al., Engineering Cyanobacteria to Synthesize and Export Hydrophilic Products. *Appl. Environ. Microbiol.*, 2010, 76(11): p. 3462-3466.

Olins et al., A Novel Sequence Element Derived from Bacteriophage T7 mRNA Acts as an Enhancer of Translation of the lacZ Gene in *Escherichia coli, Journal of Biological Chemistry*, 1989, 264(29):16973-16976.

OPX nears commercial goal for bio-based acrylic acid Feb. 28, 2011; Available from: http://www.opxbio.com/news/opxbio-rapidly-achieves-bioacrylic-commercial-goals/.

Pearson et al., Improved tools for biological sequence comparison, *Proc. Nat'l. Acad. Sci. USA*, 1988, 85:2444.

Reisch et al., Novel pathway for assimilation of dimethylsulphoniopropionate widespread in marine bacteria. *Nature*, 2011, 473(7346): p. 208-211.

Riddles et al., Ellman's reagent: 5,5'-dithiobis(2-nitrobenzoic acid)—a reexamination, *Analytical Biochemistry*, 1979, 94(1):75-81.

Ross et al., Intraspecific Variation In Stress-Induced Hydrogen Peroxide Scavenging By The Ulvoid Macroalga Ulva Lactucal. *Journal of Phycology*, 2007, 43(3): p. 466-474.

Russell, T.B., Another explanation for the toxicity of fermentation acids at low pH: anion accumulation versus uncoupling. *Journal of Applied Microbiology*, 1992, 73(5): p. 363-370.

Sakamoto et al., Growth on Urea Can Trigger Death and Peroxidation of the Cyanobacterium *Synechococcus* sp. Strain PCC 7002. *Appl. Environ. Microbiol.*, 1998, 64(7): p. 2361-2366.

Sambrook et al., *Molecular cloning: A Laboratory Manual*, $3^{rd}$ ed., Cold Spring Harbor Laboratory Press, 2001.

Simó, R., Production of atmospheric sulfur by oceanic plankton: biogeochemical, ecological and evolutionary links. *Trends in Ecology & Evolution*, 2001, 16(6): p. 287-294.

Simó et al., Coupled Dynamics of Dimethylsulfoniopropionate and Dimethylsulfide Cycling and the Microbial Food Web in Surface Waters of the North Atlantic. *Limnology and Oceanography*, 2002, 47(1): p. 53-61.

Smith et al., Comparison of Biosequences, *Adv. Appl. Math.* 1981, 2:482-489.

Steinke et al., Determinations of dimethylsulphoniopropionate (DMSP) lyase activity using headspace analysis of dimethylsulphide (DMS). *Journal of Sea Research*, 2000. 43(3-4): p. 233-244.

Straathof, A.J.J., et al., Feasibility of acrylic acid production by fermentation. *Applied Microbiology and Biotechnology*, 2005. 67(6): p. 727-734.

Stefels, J., Physiological aspects of the production and conversion of DMSP in marine algae and higher plants. *Journal of Sea Research*, 2000, 43(3-4): p. 183-197.

Sunda et al., An antioxidant function for DMSP and DMS in marine algae. *Nature*, 2002, 418(6895): p. 317-320.

Thiel, T., Genetic Analysis of Cyanobacteria, in *The Molecular Biology of Cyanobacteria*, D.A. Bryant, Editor. 2004, Springer Netherlands. p. 581-611.

Vila-Costa et al., Dimethylsulfoniopropionate Uptake by Marine Phytoplankton. *Science*, 2006, 314(5799): p. 652-654.

Visscher et al., Production and Consumption of Dimethylsulfoniopropionate in Marine Microbial Mats. *Applied and Environmental Microbiology*, 1991, 57:3237-3242.

Warnecke et al., Rapid dissection of a complex phenotype through genomic-scale mapping of fitness altering genes, *Metabolic Engineering*, 2010, 12:241-250.

Xu et al., Expression of Genes in Cyanobacteria: Adaptation of Endogenous Plasmids as Platforms for High-Level Gene Expression in *Synechococcus* sp. PCC 7002, in *Photosynthesis Research Protocols*, R. Carpentier, Editor. 2011, Humana Press. p. 273-293.

Yoch, D.C., Dimethylsulfoniopropionate: Its Sources, Role in the Marine Food Web, and Biological Degradation to Dimethylsulfide. *Appl. Environ. Microbiol.*, 2002, 68(12): p. 5804-5815.

Zaldivar et al., Effect of organic acids on the growth and fermentation of ethanologenic *Escherichia coli* LY01. *Biotechnology and Bioengineering*; Journal vol. 66; Journal Issue: 4; Other Information: PBD: 1999: p. Medium: X; Size: pp. 203-210.

\* cited by examiner

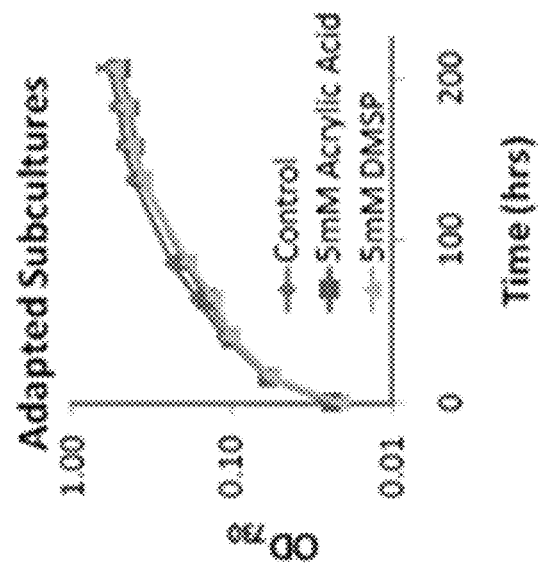
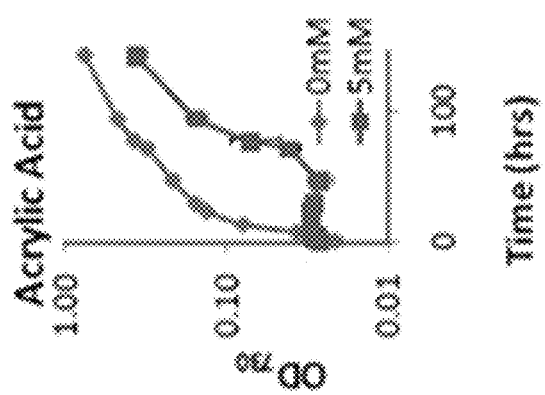
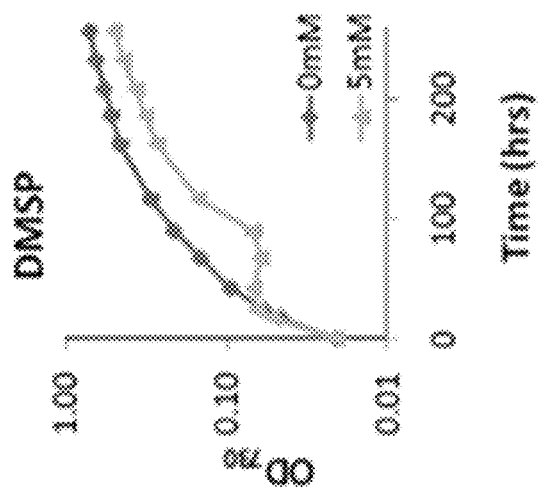
FIG. 2A
FIG. 2B
FIG. 2C

Lactate dehydrogenase

Transhydrogenase

SEQUENCE LISTING

<160> NUMBER OF SEQ ID NOS: 22

<210> SEQ ID NO 1
<211> LENGTH: 1965
<212> TYPE: DNA
<213> ORGANISM: Synechococcus PCC7002

<400> SEQUENCE: 1

```
atgtccgaac aaaacattga atccatcctc caggagcagc gccttttttc gcctgcacca      60
gactttgctg ccgaggccca gatcaagagc ttagaccagt accaagccct ctacgaccgg     120
gcgaaaaatg accccgaagg cttttggggg gaactcgccg aacaggaatt ggaatggttt     180
gagaaatggg acaaggtgct cgattggcaa ccgcccttcg ccaaatggtt tgtcaacggg     240
aaaattaaca tttcctacaa ttgcctcgac cgtcatctca aaacctggcg caaaaataaa     300
gccgccctca tctgggaagg ggaacccggt gactcccgta ccctcaccta tgcccagcta     360
caccacgagg tctgccagtt tgccaatgcg atgaaaaagt tgggcgtcaa aaaaggcgat     420
cgcgtcggga tttatatgcc aatgatcccg gaagccgtcg ttgccctcct cgcctgtgcc     480
cgcattggtg cgccccatac ggtgatattt ggtggcttta gtgccgaagc cctccgcagt     540
cgcctcgaag acgctgaagc caaactggtg atcaccgccg acgggggctt ccgcaaagat     600
aaagcggtac ccctcaagga tcaagtagat gcggcgatcg ccgatcacca tgcccccagc     660
gttgagaatg ttttggtcgt tcaacgcacc aaagagcctg tccacatgga agccgggcgg     720
gatcactggt ggcatgattt gcaaaaagaa gtctccgctg actgtccccgc cgagccgatg     780 gatgccgaag atatgctctt catcctctat accagcggca ccacgggtaa acccaagggc     840
```

-continued

```
gttgtccaca ctacgggcgg ttataatctc tacacccata taacgaccaa gtggatcttt       900
gatctcaaag atgatgacgt gtattggtgt ggtgctgatg tgggttggat caccggccac       960
agttacatta cctatggccc tctatctaac ggggcaacgg tcttaatgta tgaaggcgca      1020
ccccgtccgt ctaatcccgg ttgctattgg gaaattattc aaaaatatgg tgtcaccatt      1080
ttctatacgg cacccacagc gattcgggcc tttatcaaaa tgggtgaagg catccccaat      1140
aaatatgaca tgagttccct cgcctcttta ggaaccgtgg gtgaaccgat taacccagaa      1200
gcttggatgt ggtaccaccg ggtcattggt ggcgaacgtt gtcccattgt tgatacatgg      1260
tggcaaacgg aaaccggtgg tgtgatgatt acgcctttac ccggtgcaac tcccacaaaa      1320
cccggctcgg caactcgtcc ttttccgggg attgtggcgg atgtcgttga ccttgatgga      1380
aattccgttg gtgacaacga aggcggctac ctggtagtga acaaccctg  gcctgggatg      1440 atgcgtactg tttacggcaa tcccgaacgc ttccggtcta cctattggga gcacatcgcc      1500
ccgaaagatg gacaatacct ttatttcgca ggtgacgggg cacgccgtga ccaagatggc      1560
tatttttgga ttatgggtcg cgtcgatgat gtcttaaatg tttcgggcca tcgcctcggc      1620
accatggaag tggaatcggc cctcgtttcc caccctgccg tcgccgaagc agccgtggtt      1680
ggaaagccag atccggttaa gggggaagag gtgtttgcct ttgtcaccct tgagggcacc      1740
tacagtccga cgacgatct  cgtaacggaa ctcaaggccc atgtggtgaa agaaattggg      1800
gcgatcgccc gtccgggaga aatccgtttt gccgatgtaa tgcccaaaac ccgttctggg      1860
aagatcatgc ggcgtttgtt gcgaaaccta gccgcaggtc aggaaattgt gggcgacacc      1920
tccaccctcg aagaccgcag cgtcctcgat caactccggg gctaa                     1965
```

<210> SEQ ID NO 2
<211> LENGTH: 654
<212> TYPE: PRT
<213> ORGANISM: Synechococcus PCC7002

<400> SEQUENCE: 2

```
Met Ser Glu Gln Asn Ile Glu Ser Ile Leu Gln Glu Gln Arg Leu Phe
1               5                  10                  15

Ser Pro Ala Pro Asp Phe Ala Ala Glu Ala Gln Ile Lys Ser Leu Asp
            20                  25                  30

Gln Tyr Gln Ala Leu Tyr Asp Arg Ala Lys Asn Asp Pro Glu Gly Phe
        35                  40                  45

Trp Gly Glu Leu Ala Glu Gln Glu Leu Glu Trp Phe Glu Lys Trp Asp
    50                  55                  60

Lys Val Leu Asp Trp Gln Pro Pro Phe Ala Lys Trp Phe Val Asn Gly
65                  70                  75                  80

Lys Ile Asn Ile Ser Tyr Asn Cys Leu Asp Arg His Leu Lys Thr Trp
                85                  90                  95

Arg Lys Asn Lys Ala Ala Leu Ile Trp Glu Gly Glu Pro Gly Asp Ser
            100                 105                 110

Arg Thr Leu Thr Tyr Ala Gln Leu His His Glu Val Cys Gln Phe Ala
        115                 120                 125

Asn Ala Met Lys Lys Leu Gly Val Lys Lys Gly Asp Arg Val Gly Ile
    130                 135                 140

Tyr Met Pro Met Ile Pro Glu Ala Val Val Ala Leu Leu Ala Cys Ala
145                 150                 155                 160

Arg Ile Gly Ala Pro His Thr Val Ile Phe Gly Gly Phe Ser Ala Glu
                165                 170                 175
```

-continued

Ala Leu Arg Ser Arg Leu Glu Asp Ala Glu Ala Lys Leu Val Ile Thr
            180                 185                 190

Ala Asp Gly Gly Phe Arg Lys Asp Lys Ala Val Pro Leu Lys Asp Gln
            195                 200                 205

Val Asp Ala Ala Ile Ala Asp His His Ala Pro Ser Val Glu Asn Val
210                 215                 220

Leu Val Val Gln Arg Thr Lys Glu Pro Val His Met Glu Ala Gly Arg
225                 230                 235                 240

Asp His Trp Trp His Asp Leu Gln Lys Glu Val Ser Ala Asp Cys Pro
                245                 250                 255

Ala Glu Pro Met Asp Ala Glu Asp Met Leu Phe Ile Leu Tyr Thr Ser
            260                 265                 270

Gly Thr Thr Gly Lys Pro Lys Gly Val Val His Thr Thr Gly Gly Tyr
            275                 280                 285

Asn Leu Tyr Thr His Ile Thr Thr Lys Trp Ile Phe Asp Leu Lys Asp
            290                 295                 300

Asp Asp Val Tyr Trp Cys Gly Ala Asp Val Gly Trp Ile Thr Gly His
305                 310                 315                 320

Ser Tyr Ile Thr Tyr Gly Pro Leu Ser Asn Gly Ala Thr Val Leu Met
                325                 330                 335

Tyr Glu Gly Ala Pro Arg Pro Ser Asn Pro Gly Cys Tyr Trp Glu Ile
            340                 345                 350

Ile Gln Lys Tyr Gly Val Thr Ile Phe Tyr Thr Ala Pro Thr Ala Ile
            355                 360                 365

Arg Ala Phe Ile Lys Met Gly Glu Gly Ile Pro Asn Lys Tyr Asp Met
            370                 375                 380

Ser Ser Leu Arg Leu Leu Gly Thr Val Gly Glu Pro Ile Asn Pro Glu
385                 390                 395                 400

Ala Trp Met Trp Tyr His Arg Val Ile Gly Gly Glu Arg Cys Pro Ile
                405                 410                 415

Val Asp Thr Trp Trp Gln Thr Glu Thr Gly Gly Val Met Ile Thr Pro
            420                 425                 430

Leu Pro Gly Ala Thr Pro Thr Lys Pro Gly Ser Ala Thr Arg Pro Phe
            435                 440                 445

Pro Gly Ile Val Ala Asp Val Val Asp Leu Asp Gly Asn Ser Val Gly
450                 455                 460

Asp Asn Glu Gly Gly Tyr Leu Val Val Lys Gln Pro Trp Pro Gly Met
465                 470                 475                 480

Met Arg Thr Val Tyr Gly Asn Pro Glu Arg Phe Arg Ser Thr Tyr Trp
                485                 490                 495

Glu His Ile Ala Pro Lys Asp Gly Gln Tyr Leu Tyr Phe Ala Gly Asp
            500                 505                 510

Gly Ala Arg Arg Asp Gln Asp Gly Tyr Phe Trp Ile Met Gly Arg Val
            515                 520                 525

Asp Asp Val Leu Asn Val Ser Gly His Arg Leu Gly Thr Met Glu Val
            530                 535                 540

Glu Ser Ala Leu Val Ser His Pro Ala Val Ala Glu Ala Ala Val Val
545                 550                 555                 560

Gly Lys Pro Asp Pro Val Lys Gly Glu Glu Val Phe Ala Phe Val Thr
            565                 570                 575

Leu Glu Gly Thr Tyr Ser Pro Ser Asp Asp Leu Val Thr Glu Leu Lys
            580                 585                 590

```
Ala His Val Val Lys Glu Ile Gly Ala Ile Ala Arg Pro Gly Glu Ile
        595                 600                 605

Arg Phe Ala Asp Val Met Pro Lys Thr Arg Ser Gly Lys Ile Met Arg
    610                 615                 620

Arg Leu Leu Arg Asn Leu Ala Ala Gly Gln Glu Ile Val Gly Asp Thr
625                 630                 635                 640

Ser Thr Leu Glu Asp Arg Ser Val Leu Asp Gln Leu Arg Gly
                645                 650

<210> SEQ ID NO 3
<211> LENGTH: 1962
<212> TYPE: DNA
<213> ORGANISM: Synechocystis PCC6803

<400> SEQUENCE: 3
atgtcagata ccattgaatc catcctgcag gaagagcgac tgtttgatcc ccctacagaa      60
tttagtgagc gggcttacgt gcgtagtggg cgggagtatg agcaactgta cagccgggcg     120
gccagcaatc cggagaagtt ttggggtgag ctggcggagc aggaattaca ttggtttaaa     180
aaatgggacc aggttttgga ttggcaacct ccctttgcga atggtttgt gggggtcag      240 ttaaatattt cccataactg tttggatcgg cacttaacca cctggcggcg caataaggcg     300
gccattattt ggaggggga accgggagat tcccggataa ttacctatgc caactccat      360 cgggaagtgt gtcagtttgc caatgccctg aaaagtttag gcgtgcaaaa aggtgatcgg     420
gtagcaattt atctgcccat gattcccgaa gcggcgatca ccatgttggc ctgttcccgt     480
atcggtgcgc cccatagtgt tgtgtttggt gggtttagtg cggaagccct gcgggatcga     540
ttagtggatg ctgaagccaa attggtcata actgccgacg gtggttttcg taagataag      600 gcgatcgccc tgaagcagga gtggataag gccctggaac acggtgcccc cagcgtggaa     660
aacgtcatcg tcgtgcaaag aactaaagcc gatgtgacca tgacggcggg acgggaccac     720
tggtggcaca actccaacc tcaacagtcg gcccattgcc cagcggaacc catagacagt     780
gaagatatgc tgtttattct ctacacctct ggcagtactg gcaaaccaaa aggcgtggtc     840
cacaccaccg ggggtacaa cctttacacc cacatgacca ccaaatggat ctttgacctc     900
aaagatacgg acgtttattg gtgtaccgct gatgtgggtt ggattacggg ccacagctac     960
attgtttacg gccccctgtc caacggtgca acaacggtaa tgtatgaagg ggtgccccgc    1020
ccctccaacc ccggttgttt tgggacgta attgaaaggt atggggtgaa tattttctac    1080
accgccccca ccgccatccg agcctttatt cgcatggggg aagccgtacc caacgccagg    1140
gatttatcct ctctccgttt actgggcact gtgggggaac ccattaaccc cgaagcttgg    1200
atgtggtacc accgggtcat ggcggcggt aaatgcccca ttgtcgatac ctggtggcaa    1260
acggaaaccg gcggcattat gctcactccc ctacctggag ctatccctac caaacccggt    1320
tcttgtacca aaccttttcc cggcattgtg gcggaaattg ttgatttaga tggcaatccc    1380
gtcgagtcag accaagggg cttttagtg attaaacaac cttggccag catgattcgg      1440 gatgtgtacg gcgacaccga tcgcttccgc catacctatt ggaacatat tcaacccaag    1500 gagggacaat atctctactt tgctggggac ggggcccgcc gggataaaga cggttatttt    1560
tgggtcatgg gccgggtgga tgatgtgatt aatgtctctg gtcaccgttt aggcactatg    1620
gaaattgaat cggctttggt tccccatccc ctcgtagcgg aagcggcggt ggtgggtcgc    1680
cccgatgaat tgactgggga agccattttc gcctttgttt ctctggaggg taacgctgaa    1740
cccagtgaag agttgaaaaa agatttggtc aagcacgtca ctgaagaaat tgggggcgatc    1800
```

-continued

```
gccaggccag cggaaatccg tttcaccgat gtgttaccca aaacccgttc cggcaaaatt    1860
atgcgtcgtc tgttgcggag tttagcctcc gggcaggaaa tttccgggga cacttccacc    1920
ctggaggacc ggacagtgct ggacaaatta cgggagggct aa                        1962
```

```
<210> SEQ ID NO 4
<211> LENGTH: 653
<212> TYPE: PRT
<213> ORGANISM: Synechocystis PCC6803

<400> SEQUENCE: 4
```

| Met | Ser | Asp | Thr | Ile | Glu | Ser | Ile | Leu | Gln | Glu | Glu | Arg | Leu | Phe | Asp |
|---|---|---|---|---|---|---|---|---|---|---|---|---|---|---|---|
| 1 | | | | 5 | | | | | 10 | | | | | 15 | |

| Pro | Pro | Thr | Glu | Phe | Ser | Glu | Arg | Ala | Tyr | Val | Arg | Ser | Gly | Arg | Glu |
| | | 20 | | | | | 25 | | | | | 30 | | | |

| Tyr | Glu | Gln | Leu | Tyr | Ser | Arg | Ala | Ala | Ser | Asn | Pro | Glu | Lys | Phe | Trp |
| | | | 35 | | | | | 40 | | | | | 45 | | |

| Gly | Glu | Leu | Ala | Glu | Gln | Glu | Leu | His | Trp | Phe | Lys | Lys | Trp | Asp | Gln |
| | 50 | | | | | 55 | | | | | 60 | | | | |

| Val | Leu | Asp | Trp | Gln | Pro | Pro | Phe | Ala | Lys | Trp | Phe | Val | Gly | Gly | Gln |
| 65 | | | | | 70 | | | | | 75 | | | | | 80 |

| Leu | Asn | Ile | Ser | His | Asn | Cys | Leu | Asp | Arg | His | Leu | Thr | Thr | Trp | Arg |
| | | | | 85 | | | | | 90 | | | | | 95 | |

| Arg | Asn | Lys | Ala | Ala | Ile | Ile | Trp | Glu | Gly | Glu | Pro | Gly | Asp | Ser | Arg |
| | | | 100 | | | | | 105 | | | | | 110 | | |

| Ile | Ile | Thr | Tyr | Ala | Gln | Leu | His | Arg | Glu | Val | Cys | Gln | Phe | Ala | Asn |
| | | 115 | | | | | 120 | | | | | 125 | | | |

| Ala | Leu | Lys | Ser | Leu | Gly | Val | Gln | Lys | Gly | Asp | Arg | Val | Ala | Ile | Tyr |
| | 130 | | | | | 135 | | | | | 140 | | | | |

| Leu | Pro | Met | Ile | Pro | Glu | Ala | Ala | Ile | Thr | Met | Leu | Ala | Cys | Ser | Arg |
| 145 | | | | | 150 | | | | | 155 | | | | | 160 |

| Ile | Gly | Ala | Pro | His | Ser | Val | Val | Phe | Gly | Phe | Ser | Ala | Glu | Ala |
| | | | | 165 | | | | | 170 | | | | | 175 |

| Leu | Arg | Asp | Arg | Leu | Val | Asp | Ala | Glu | Ala | Lys | Leu | Val | Ile | Thr | Ala |
| | | | 180 | | | | | 185 | | | | | 190 | | |

| Asp | Gly | Gly | Phe | Arg | Lys | Asp | Lys | Ala | Ile | Ala | Leu | Lys | Gln | Glu | Val |
| | | 195 | | | | | 200 | | | | | 205 | | | |

| Asp | Lys | Ala | Leu | Glu | His | Gly | Ala | Pro | Ser | Val | Glu | Asn | Val | Ile | Val |
| | 210 | | | | | 215 | | | | | 220 | | | | |

| Val | Gln | Arg | Thr | Lys | Ala | Asp | Val | Thr | Met | Thr | Ala | Gly | Arg | Asp | His |
| 225 | | | | | 230 | | | | | 235 | | | | | 240 |

| Trp | Trp | His | Glu | Leu | Gln | Pro | Gln | Gln | Ser | Ala | His | Cys | Pro | Ala | Glu |
| | | | | 245 | | | | | 250 | | | | | 255 | |

| Pro | Ile | Asp | Ser | Glu | Asp | Met | Leu | Phe | Ile | Leu | Tyr | Thr | Ser | Gly | Ser |
| | | | 260 | | | | | 265 | | | | | 270 | | |

| Thr | Gly | Lys | Pro | Lys | Gly | Val | Val | His | Thr | Thr | Gly | Gly | Tyr | Asn | Leu |
| | | 275 | | | | | 280 | | | | | 285 | | | |

| Tyr | Thr | His | Met | Thr | Thr | Lys | Trp | Ile | Phe | Asp | Leu | Lys | Asp | Thr | Asp |
| | 290 | | | | | 295 | | | | | 300 | | | | |

| Val | Tyr | Trp | Cys | Thr | Ala | Asp | Val | Gly | Trp | Ile | Thr | Gly | His | Ser | Tyr |
| 305 | | | | | 310 | | | | | 315 | | | | | 320 |

| Ile | Val | Tyr | Gly | Pro | Leu | Ser | Asn | Gly | Ala | Thr | Thr | Val | Met | Tyr | Glu |
| | | | | 325 | | | | | 330 | | | | | 335 | |

| Gly | Val | Pro | Arg | Pro | Ser | Asn | Pro | Gly | Cys | Phe | Trp | Asp | Val | Ile | Glu |

```
            340                 345                 350
Arg Tyr Gly Val Asn Ile Phe Tyr Thr Ala Pro Thr Ala Ile Arg Ala
            355                 360                 365
Phe Ile Arg Met Gly Glu Ala Val Pro Asn Ala Arg Asp Leu Ser Ser
        370                 375                 380
Leu Arg Leu Leu Gly Thr Val Gly Glu Pro Ile Asn Pro Glu Ala Trp
385                 390                 395                 400
Met Trp Tyr His Arg Val Ile Gly Gly Lys Cys Pro Ile Val Asp
                405                 410                 415
Thr Trp Trp Gln Thr Glu Thr Gly Gly Ile Met Leu Thr Pro Leu Pro
                420                 425                 430
Gly Ala Ile Pro Thr Lys Pro Gly Ser Cys Thr Lys Pro Phe Pro Gly
            435                 440                 445
Ile Val Ala Glu Ile Val Asp Leu Asp Gly Asn Pro Val Glu Ser Asp
        450                 455                 460
Gln Gly Gly Phe Leu Val Ile Lys Gln Pro Trp Pro Ser Met Ile Arg
465                 470                 475                 480
Asp Val Tyr Gly Asp Thr Asp Arg Phe Arg His Thr Tyr Trp Glu His
                485                 490                 495
Ile Gln Pro Lys Glu Gly Gln Tyr Leu Tyr Phe Ala Gly Asp Gly Ala
                500                 505                 510
Arg Arg Asp Lys Asp Gly Tyr Phe Trp Val Met Gly Arg Val Asp Asp
            515                 520                 525
Val Ile Asn Val Ser Gly His Arg Leu Gly Thr Met Glu Ile Glu Ser
        530                 535                 540
Ala Leu Val Ser His Pro Leu Val Ala Glu Ala Val Val Gly Arg
545                 550                 555                 560
Pro Asp Glu Leu Thr Gly Glu Ala Ile Phe Ala Phe Val Ser Leu Glu
                565                 570                 575
Gly Asn Ala Glu Pro Ser Glu Glu Leu Lys Lys Asp Leu Val Lys His
                580                 585                 590
Val Thr Glu Glu Ile Gly Ala Ile Ala Arg Pro Ala Glu Ile Arg Phe
            595                 600                 605
Thr Asp Val Leu Pro Lys Thr Arg Ser Gly Lys Ile Met Arg Arg Leu
        610                 615                 620
Leu Arg Ser Leu Ala Ser Gly Gln Glu Ile Ser Gly Asp Thr Ser Thr
625                 630                 635                 640
Leu Glu Asp Arg Thr Val Leu Asp Lys Leu Arg Glu Gly
                645                 650

<210> SEQ ID NO 5
<211> LENGTH: 1971
<212> TYPE: DNA
<213> ORGANISM: Synechococcus PCC7942

<400> SEQUENCE: 5
atgagccagc caacgatcga gtcgatcctc aagagaagc gggttttttcc tccctcggca    60 gaatttgcca gtgcggcgcg aatcaatccc gaagcgtacg aagcgctctg ccagaaagcg   120
gcggccgatc cggtggcttt ttggggcgaa ttggcagctc aggagctgga ctggttttgag  180 ccttggcaac agacgctgga ctggagcaat ccgccgtttg cgaagtggtt tgtcggtggc   240
aaactcaata tttcccacaa ctgcctcgat cgccacttga cgacttggcg caaaaataaa   300
gcggcgatta tctgggaagg cgaacccggt gactcacgga cgctgaccta cgcgcaactg   360
```

-continued

| | |
|---|---|
| catcgcgagg tctgtcagtt cgccaacgtg ctcaaatcct tgggcattca aaaaggtgat | 420 |
| gtcgttggcg tttacatgcc gatgattccc gaagcggcga tcgccatgct ggcctgtgcg | 480 |
| cggattggcg cagtgcatag cgttgtcttt gggggcttta gtgcggaagc actgcgcgat | 540 |
| cgcttggtgg atggccaagc caagctggtt gtcacggcgg atggtggctg cgcaaagat | 600 |
| gcgatcgtgc ccctcaagga ttctgttgat caagccctgg aaggcaatgc ctgccccagc | 660 |
| gtccagcatg tcctcgtggt ggaacggacg aagcaagaca tccacatgga accggggcgc | 720 |
| gaccattggt ggcatgagct gcaacagacc gtcagcgcta cctgtccggc ggagccgatg | 780 |
| gacagcgaag atctgctctt cgtgctctac acctccggta gcaccggcaa acccaagggt | 840 |
| gtcgtccaca ccaccggcgg ctacaacctc tacgcccaca tcaccaccca gtggactttt | 900 |
| gacctgcagg ataccgatgt ctactggtgt acggcggacg tcggctggat taccggtcac | 960 |
| agctacatcg tctacgggcc gctctccaac ggtgcgacca cactgatgta tgagggtgcc | 1020 |
| ccccgcgctt ctaatcccgg ttgcttctgg gatgtgattg aaaagtatgg cgttacgacc | 1080 |
| ttctacacag cccaacagc gatccgcgcc ttcatcaaaa tgggtgagca gcatcccgcc | 1140 |
| gctcgcgacc tctcctcatt gcgactgttg ggcaccgtcg gagagcccat caatcccgaa | 1200 |
| gcttggatct ggtatcaccg cgtcattggt ggcgatcgct gcccgattgt cgatacctgg | 1260 |
| tggcagaccg aaacgggcgg ccatatgatt acgtcgctgc cgggagccgt gccgaccaaa | 1320 |
| ccgggctctg ccactaaacc tttccccggg atccttggcag acgttgtcga tctggatggg | 1380 |
| cgatcggtgc cggataacga aggtggctac ttggtgattc gccatccttg gccaggcatg | 1440 |
| atgcgcacgg tctacggcga tcccgatcgc ttccgtcgca cctattggga gcatattcct | 1500 |
| ccgcaaaatg gccagtatct ctacttcgcc ggcgatggcg cgcgccgcga tgccgatggc | 1560 |
| tatttctggg tgatggggcg cgtcgatgac gtgatcaatg tctcaggtca ccgtctcggc | 1620 |
| acgatggaaa ttgagtcggc cttggtctcc catccggcag ttgccgaagc tgcagttgtc | 1680 |
| ggtcggcctg acgatctcaa aggtgaaggc attgttgctt tcatcacgct ggaatcgggc | 1740 |
| attgagactg gcgatgagtt agttaaagac ctgaagaaac acgtcgccca gaaaattggc | 1800 |
| gcgatcgctc gtcccgatga aattcgcttc agtgaggcgc tgcccaaaac gcgatcgggc | 1860 |
| aagattatgc gccgtctgtt gcgcagtctc gccgctggtc aagaagtttc gggcgacact | 1920 |
| tccaccttgg aagatcgctc ggtgctcgat aagctgcgtc aaggcactta g | 1971 |

<210> SEQ ID NO 6
<211> LENGTH: 656
<212> TYPE: PRT
<213> ORGANISM: Synechococcus PCC7942

<400> SEQUENCE: 6

```
Met Ser Gln Pro Thr Ile Glu Ser Ile Leu Gln Glu Lys Arg Val Phe
1               5                   10                  15

Pro Pro Ser Ala Glu Phe Ala Ser Ala Ala Arg Ile Asn Pro Glu Ala
            20                  25                  30

Tyr Glu Ala Leu Cys Gln Lys Ala Ala Ala Asp Pro Val Ala Phe Trp
        35                  40                  45

Gly Glu Leu Ala Ala Gln Glu Leu Asp Trp Phe Glu Pro Trp Gln Gln
    50                  55                  60

Thr Leu Asp Trp Ser Asn Pro Pro Phe Ala Lys Trp Phe Val Gly Gly
65                  70                  75                  80

Lys Leu Asn Ile Ser His Asn Cys Leu Asp Arg His Leu Thr Thr Trp
                85                  90                  95
```

```
Arg Lys Asn Lys Ala Ile Ile Trp Glu Gly Glu Pro Gly Asp Ser
            100                 105                 110

Arg Thr Leu Thr Tyr Ala Gln Leu His Arg Glu Val Cys Gln Phe Ala
            115                 120                 125

Asn Val Leu Lys Ser Leu Gly Ile Gln Lys Gly Asp Val Val Gly Val
        130                 135                 140

Tyr Met Pro Met Ile Pro Glu Ala Ala Ile Ala Met Leu Ala Cys Ala
145                 150                 155                 160

Arg Ile Gly Ala Val His Ser Val Val Phe Gly Gly Phe Ser Ala Glu
                165                 170                 175

Ala Leu Arg Asp Arg Leu Val Asp Gly Gln Ala Lys Leu Val Val Thr
            180                 185                 190

Ala Asp Gly Gly Trp Arg Lys Asp Ala Ile Val Pro Leu Lys Asp Ser
        195                 200                 205

Val Asp Gln Ala Leu Glu Gly Asn Ala Cys Pro Ser Val Gln His Val
210                 215                 220

Leu Val Val Glu Arg Thr Lys Gln Asp Ile His Met Glu Pro Gly Arg
225                 230                 235                 240

Asp His Trp Trp His Glu Leu Gln Gln Thr Val Ser Ala Thr Cys Pro
                245                 250                 255

Ala Glu Pro Met Asp Ser Glu Asp Leu Leu Phe Val Leu Tyr Thr Ser
            260                 265                 270

Gly Ser Thr Gly Lys Pro Lys Gly Val Val His Thr Thr Gly Gly Tyr
        275                 280                 285

Asn Leu Tyr Ala His Ile Thr Thr Gln Trp Thr Phe Asp Leu Gln Asp
        290                 295                 300

Thr Asp Val Tyr Trp Cys Thr Ala Asp Val Gly Trp Ile Thr Gly His
305                 310                 315                 320

Ser Tyr Ile Val Tyr Gly Pro Leu Ser Asn Gly Ala Thr Thr Leu Met
                325                 330                 335

Tyr Glu Gly Ala Pro Arg Ala Ser Asn Pro Gly Cys Phe Trp Asp Val
            340                 345                 350

Ile Glu Lys Tyr Gly Val Thr Thr Phe Tyr Thr Ala Pro Thr Ala Ile
        355                 360                 365

Arg Ala Phe Ile Lys Met Gly Glu Gln His Pro Ala Ala Arg Asp Leu
370                 375                 380

Ser Ser Leu Arg Leu Leu Gly Thr Val Gly Glu Pro Ile Asn Pro Glu
385                 390                 395                 400

Ala Trp Ile Trp Tyr His Arg Val Ile Gly Asp Arg Cys Pro Ile
                405                 410                 415

Val Asp Thr Trp Trp Gln Thr Glu Thr Gly Gly His Met Ile Thr Ser
            420                 425                 430

Leu Pro Gly Ala Val Pro Thr Lys Pro Gly Ser Ala Thr Lys Pro Phe
        435                 440                 445

Pro Gly Ile Leu Ala Asp Val Val Asp Leu Asp Gly Arg Ser Val Pro
        450                 455                 460

Asp Asn Glu Gly Gly Tyr Leu Val Ile Arg His Pro Trp Pro Gly Met
465                 470                 475                 480

Met Arg Thr Val Tyr Gly Asp Pro Asp Arg Phe Arg Arg Thr Tyr Trp
                485                 490                 495

Glu His Ile Pro Pro Gln Asn Gly Gln Tyr Leu Tyr Phe Ala Gly Asp
            500                 505                 510
```

```
Gly Ala Arg Arg Asp Ala Asp Gly Tyr Phe Trp Val Met Gly Arg Val
            515                 520                 525

Asp Asp Val Ile Asn Val Ser Gly His Arg Leu Gly Thr Met Glu Ile
        530                 535                 540

Glu Ser Ala Leu Val Ser His Pro Ala Val Glu Ala Ala Val Val
545                 550                 555                 560

Gly Arg Pro Asp Asp Leu Lys Gly Glu Gly Ile Val Ala Phe Ile Thr
                565                 570                 575

Leu Glu Ser Gly Ile Glu Thr Gly Asp Glu Leu Val Lys Asp Leu Lys
            580                 585                 590

Lys His Val Ala Gln Glu Ile Gly Ala Ile Ala Arg Pro Asp Glu Ile
        595                 600                 605

Arg Phe Ser Glu Ala Leu Pro Lys Thr Arg Ser Gly Lys Ile Met Arg
    610                 615                 620

Arg Leu Leu Arg Ser Leu Ala Ala Gly Gln Glu Val Ser Gly Asp Thr
625                 630                 635                 640

Ser Thr Leu Glu Asp Arg Ser Val Leu Asp Lys Leu Arg Gln Gly Thr
                645                 650                 655

<210> SEQ ID NO 7
<211> LENGTH: 3898
<212> TYPE: DNA
<213> ORGANISM: Chloroflexus aurantiacus

<400> SEQUENCE: 7
aacatcatgg tatactatac ctatcgataa ttcttcaact aattgcataa cagaacagcg      60
atggcgacgg gggagtccat gagcggaaca ggacgactgg caggaaagat tgcgttaatt     120
accggtggcg ccgcaatat cggcagtgaa ttgacacgtc gctttctcgc agagggagcg     180
acggtcatta ttagtggacg gaatcgggcg aagttgaccg cactggccga acggatgcag     240
gcagaggcag gagtgccggc aaagcgcatc gatctcgaag tcatggatgg gagtgatccg     300
gtcgcggtac gtgccggtat cgaagcgatt gtggcccgtc acggccagat cgacattctg     360
gtcaacaatg caggaagtgc cggtgcccag cgtcgtctgg ccgagattcc actcactgaa     420
gctgaattag cccctggcgc cgaagagacg cttcatgcca gcatcgccaa tttacttggt     480
atgggatggc atctgatgcg tattgcggca cctcatatgc cggtaggaag tgcggtcatc     540
aatgtctcga ccatcttttc acgggctgag tactacgggc ggattccgta tgtcaccccct    600 aaagctgctc ttaatgctct atctcaactt gctgcgcgtg agttaggtgc acgtggcatc     660
cgcgttaata cgatctttcc cggccccgatt gaaagtgatc gcatccgtac agtgttccag    720
cgtatggatc agctcaaggg gcggcccgaa ggcgacacag cgcaccattt tttgaacacc     780
atgcgattgt gtcgtgccaa cgaccagggc gcgcttgaac gtcggttccc ctcccgtcgg    840
gatgtggcag acgccgctgt ctttctggcc agtgccgaat ccgccgctct ctccggtgag     900
acgattgagg ttacgcacgg aatggagttg ccggcctgca gtgagaccag cctgctggcc     960
cgtactgatc tgcgcacgat tgatgccagt ggccgcacga cgctcatctg cgccggcgac    1020
cagattgaag aggtgatggc gctcaccggt atgttgcgta cctgtgggag tgaagtgatc    1080
atcggcttcc gttcggctgc ggcgctggcc cagttcgagc aggcagtcaa tgagagtcgg    1140
cggctggccg cgcagactt tacgcctccc attgccttgc cactcgatcc acgcgatccg    1200
gcaacaattg acgctgtctt cgattggggg gccggcgaga ataccggcgg gattcatgca     1260
gcggtgattc tgcctgctac cagtcacgaa ccggcaccgt gcgtgattga ggttgatgat    1320
```

-continued

```
gagcgggtgc tgaattttct ggccgatgaa atcaccggga caattgtgat tgccagtcgc   1380
ctggcccgtt actggcagtc gcaacggctt accccggcg cacgtgcgcg tgggccgcgt    1440 gtcattttc tctcgaacgg tgccgatcaa aatgggaatg tttacggacg cattcaaagt   1500
gccgctatcg gtcagctcat tcgtgtgtgg cgtcacgagg ctgaacttga ctatcagcgt   1560
gccagcgccg ccggtgatca tgtgctgccg ccggtatggg ccaatcagat tgtgcgcttc   1620
gctaaccgca gccttgaagg gttagaattt gcctgtgcct ggacagctca attgctccat   1680
agtcaacgcc atatcaatga gattaccctc aacatccctg ccaacattag cgccaccacc   1740
ggcgcacgca gtgcatcggt cggatgggcg gaaagcctga tcggttgca tttggggaaa    1800 gttgccttga ttaccggtgg cagcgccggt attggtgggc agatcgggcg cctcctggct   1860
ttgagtggcg cgcgcgtgat gctggcagcc cgtgatcggc ataagctcga acagatgcag   1920
gcgatgatcc aatctgagct ggctgaggtg gggtataccg atgtcgaaga tcgcgtccac   1980
attgcaccgg gctgcgatgt gagtagcgaa gcgcagcttg cggatcttgt tgaacgtacc   2040
ctgtcagctt ttggcaccgt cgattatctg atcaacaacg ccgggatcgc cggtgtcgaa   2100
gagatggtta tcgatatgcc agttgaggga tggcgccata ccctcttcgc caatctgatc   2160
agcaactact cgttgatgcg caaactggcg ccgttgatga aaaacaggg tagcggttac    2220 atccttaacg tctcatcata ctttggcggt gaaaagatg cggccattcc ctaccccaac    2280
cgtgccgatt acgcgtctc gaaggctggt cagcgggcaa tggccgaagt ctttgcgcgc   2340
ttccttggcc cggagataca gatcaatgcc attgcgccgg gtccggtcga aggtgatcgc   2400
ttgcgcggta ccggtgaacg tcccggcctc tttgcccgtc gggcgcggct gattttggag   2460
aacaagcggc tgaatgagct tcacgctgct cttatcgcgg ctgcgcgcac cgatgagcga   2520
tctatgcacg aactggttga actgctctta cccaatgatg tggccgcact agagcagaat   2580
cccgcagcac ctaccgcgtt gcgtgaactg gcacgacgtt ttcgcagcga aggcgatccg   2640
gcggcatcat caagcagtgc gctgctgaac cgttcaattg ccgctaaatt gctggctcgt   2700
ttgcataatg gtggctatgt gttgcctgcc gacatctttg caaacctgcc aaacccgccc   2760
gatcccttct tcacccgagc ccagattgat cgcgaggctc gcaaggttcg tgacggcatc   2820
atggggatgc tctacctgca acggatgccg actgagtttg atgtcgcaat ggccaccgtc   2880
tattaccttg ccgaccgcaa tgtcagtggt gagacattcc acccatcagg tggtttgcgt   2940
tacgaacgca cccctaccgg tggcgaactc ttcggcttgc cctcaccgga acggctggcg   3000
gagctggtcg gaagcacggt ctatctgata ggtgaacatc tgactgaaca ccttaacctg   3060
cttgcccgtg cgtacctcga acgttacggg gcacgtcagg tagtgatgat tgttgagaca   3120
gaaaccgggg cagagacaat gcgtcgcttg ctccacgatc acgtcgaggc tggtcggctg   3180
atgactattg tggccggtga tcagatcgaa gccgctatcg accaggctat cactcgctac   3240
ggtcgcccag gccggtcgt ctgtacccc ttccggccac tgccgacggt accactggtc     3300
gggcgtaaag acagtgactg gagcacagtg ttgagtgagg ctgaatttgc cgagttgtgc   3360
gaacaccagc tcacccacca tttccgggta gcgcgcaaga ttgccctgag tgatggtgcc   3420
agtctcgcgc tggtcactcc cgaaactacg gctacctcaa ctaccgagca atttgctctg   3480
gctaacttca tcaaaacgac ccttcacgct tttacggcta cgattggtgt cgagagcgaa   3540
agaactgctc agcgcattct gatcaatcaa gtcgatctga cccggcgtgc gcgtgccgaa   3600
gagccgcgtg atccgcacga gcgtcaacaa gaactggaac gttttatcga ggcagtcttg   3660
ctggtcactg caccactccc gcctgaagcc gatacccgtt acgccgggcg gattcatcgc   3720
```

```
ggacgggcga ttaccgtgta aattctacgc cacaggaacc actaccaaac cagcatagta    3780
agagaacgat agagacgttg caatgcgacg tctctatcat atttccggcc ccccctagac    3840 aaaccccac gtcttcgtgt agactagaaa caggaggctg tatgcacgtc aacaaga       3898
```

<210> SEQ ID NO 8
<211> LENGTH: 1220
<212> TYPE: PRT
<213> ORGANISM: Chloroflexus aurantiacus

<400> SEQUENCE: 8

```
Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
```

```
                340                 345                 350
Ser Arg Arg Leu Ala Gly Ala Asp Phe Thr Pro Ile Ala Leu Pro
            355                 360                 365

Leu Asp Pro Arg Asp Pro Ala Thr Ile Asp Ala Val Phe Asp Trp Gly
        370                 375                 380

Ala Gly Glu Asn Thr Gly Gly Ile His Ala Ala Val Ile Leu Pro Ala
385                 390                 395                 400

Thr Ser His Glu Pro Ala Pro Cys Val Ile Glu Val Asp Asp Glu Arg
                405                 410                 415

Val Leu Asn Phe Leu Ala Asp Glu Ile Thr Gly Thr Ile Val Ile Ala
            420                 425                 430

Ser Arg Leu Ala Arg Tyr Trp Gln Ser Gln Arg Leu Thr Pro Gly Ala
        435                 440                 445

Arg Ala Arg Gly Pro Arg Val Ile Phe Leu Ser Asn Gly Ala Asp Gln
                450                 455                 460

Asn Gly Asn Val Tyr Gly Arg Ile Gln Ser Ala Ala Ile Gly Gln Leu
465                 470                 475                 480

Ile Arg Val Trp Arg His Glu Ala Glu Leu Asp Tyr Gln Arg Ala Ser
                485                 490                 495

Ala Ala Gly Asp His Val Leu Pro Pro Val Trp Ala Asn Gln Ile Val
            500                 505                 510

Arg Phe Ala Asn Arg Ser Leu Glu Gly Leu Glu Phe Ala Cys Ala Trp
        515                 520                 525

Thr Ala Gln Leu Leu His Ser Gln Arg His Ile Asn Glu Ile Thr Leu
    530                 535                 540

Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
                565                 570                 575

Leu Ile Thr Gly Gly Ser Ala Gly Ile Gly Gly Gln Ile Gly Arg Leu
            580                 585                 590

Leu Ala Leu Ser Gly Ala Arg Val Met Leu Ala Ala Arg Asp Arg His
        595                 600                 605

Lys Leu Glu Gln Met Gln Ala Met Ile Gln Ser Glu Leu Ala Glu Val
    610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
            660                 665                 670

Val Glu Glu Met Val Ile Asp Met Pro Val Glu Gly Trp Arg His Thr
        675                 680                 685

Leu Phe Ala Asn Leu Ile Ser Asn Tyr Ser Leu Met Arg Lys Leu Ala
    690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                725                 730                 735

Asp Tyr Ala Val Ser Lys Ala Gly Gln Arg Ala Met Ala Glu Val Phe
            740                 745                 750

Ala Arg Phe Leu Gly Pro Glu Ile Gln Ile Asn Ala Ile Ala Pro Gly
        755                 760                 765
```

```
Pro Val Glu Gly Asp Arg Leu Arg Gly Thr Gly Glu Arg Pro Gly Leu
    770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Arg Thr Asp Glu Arg Ser Met
                805                 810                 815

His Glu Leu Val Glu Leu Leu Pro Asn Asp Val Ala Ala Leu Glu
                820                 825                 830

Gln Asn Pro Ala Ala Pro Thr Ala Leu Arg Glu Leu Ala Arg Arg Phe
            835                 840                 845

Arg Ser Glu Gly Asp Pro Ala Ala Ser Ser Ser Ala Leu Leu Asn
    850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
                885                 890                 895

Phe Phe Thr Arg Ala Gln Ile Asp Arg Glu Ala Arg Lys Val Arg Asp
                900                 905                 910

Gly Ile Met Gly Met Leu Tyr Leu Gln Arg Met Pro Thr Glu Phe Asp
                915                 920                 925

Val Ala Met Ala Thr Val Tyr Tyr Leu Ala Asp Arg Asn Val Ser Gly
                930                 935                 940

Glu Thr Phe His Pro Ser Gly Gly Leu Arg Tyr Glu Arg Thr Pro Thr
945                 950                 955                 960

Gly Gly Glu Leu Phe Gly Leu Pro Ser Pro Glu Arg Leu Ala Glu Leu
                965                 970                 975

Val Gly Ser Thr Val Tyr Leu Ile Gly Glu His Leu Thr Glu His Leu
                980                 985                 990

Asn Leu Leu Ala Arg Ala Tyr Leu Glu Arg Tyr Gly Ala Arg Gln Val
            995                 1000                1005

Val Met Ile Val Glu Thr Glu Thr Gly Ala Glu Thr Met Arg Arg
    1010                1015                1020

Leu Leu His Asp His Val Glu Ala Gly Arg Leu Met Thr Ile Val
    1025                1030                1035

Ala Gly Asp Gln Ile Glu Ala Ala Ile Asp Gln Ala Ile Thr Arg
    1040                1045                1050

Tyr Gly Arg Pro Gly Pro Val Val Cys Thr Pro Phe Arg Pro Leu
    1055                1060                1065

Pro Thr Val Pro Leu Val Gly Arg Lys Asp Ser Asp Trp Ser Thr
    1070                1075                1080

Val Leu Ser Glu Ala Glu Phe Ala Glu Leu Cys Glu His Gln Leu
    1085                1090                1095

Thr His His Phe Arg Val Ala Arg Lys Ile Ala Leu Ser Asp Gly
    1100                1105                1110

Ala Ser Leu Ala Leu Val Thr Pro Glu Thr Thr Ala Thr Ser Thr
    1115                1120                1125

Thr Glu Gln Phe Ala Leu Ala Asn Phe Ile Lys Thr Thr Leu His
    1130                1135                1140

Ala Phe Thr Ala Thr Ile Gly Val Glu Ser Glu Arg Thr Ala Gln
    1145                1150                1155

Arg Ile Leu Ile Asn Gln Val Asp Leu Thr Arg Arg Ala Arg Ala
    1160                1165                1170
```

-continued

```
Glu Glu Pro Arg Asp Pro His Glu Arg Gln Gln Glu Leu Glu Arg
    1175                1180                1185

Phe Ile Glu Ala Val Leu Leu Val Thr Ala Pro Leu Pro Pro Glu
    1190                1195                1200

Ala Asp Thr Arg Tyr Ala Gly Arg Ile His Arg Gly Arg Ala Ile
    1205                1210                1215

Thr Val
    1220

<210> SEQ ID NO 9
<211> LENGTH: 652
<212> TYPE: PRT
<213> ORGANISM: Escherichia coli

<400> SEQUENCE: 9

Met Ser Gln Ile His Lys His Thr Ile Pro Ala Asn Ile Ala Asp Arg
1               5                   10                  15

Cys Leu Ile Asn Pro Gln Gln Tyr Glu Ala Met Tyr Gln Gln Ser Ile
                20                  25                  30

Asn Val Pro Asp Thr Phe Trp Gly Glu Gln Gly Lys Ile Leu Asp Trp
            35                  40                  45

Ile Lys Pro Tyr Gln Lys Val Lys Asn Thr Ser Phe Ala Pro Gly Asn
    50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
                85                  90                  95

Trp Glu Gly Asp Asp Ala Ser Gln Ser Lys His Ile Ser Tyr Lys Glu
                100                 105                 110

Leu His Arg Asp Val Cys Arg Phe Ala Asn Thr Leu Leu Glu Leu Gly
            115                 120                 125

Ile Lys Lys Gly Asp Val Val Ala Ile Tyr Met Pro Met Val Pro Glu
    130                 135                 140

Ala Ala Val Ala Met Leu Ala Cys Ala Arg Ile Gly Ala Val His Ser
145                 150                 155                 160

Val Ile Phe Gly Gly Phe Ser Pro Glu Ala Val Ala Gly Arg Ile Ile
                165                 170                 175

Asp Ser Asn Ser Arg Leu Val Ile Thr Ser Asp Glu Gly Val Arg Ala
            180                 185                 190

Gly Arg Ser Ile Pro Leu Lys Lys Asn Val Asp Asp Ala Leu Lys Asn
    195                 200                 205

Pro Asn Val Thr Ser Val Glu His Val Val Val Leu Lys Arg Thr Gly
    210                 215                 220

Gly Lys Ile Asp Trp Gln Glu Gly Arg Asp Leu Trp Trp His Asp Leu
225                 230                 235                 240

Val Glu Gln Ala Ser Asp Gln His Gln Ala Glu Glu Met Asn Ala Glu
                245                 250                 255

Asp Pro Leu Phe Ile Leu Tyr Thr Ser Gly Ser Thr Gly Lys Pro Lys
            260                 265                 270

Gly Val Leu His Thr Thr Gly Gly Tyr Leu Val Tyr Ala Ala Leu Thr
    275                 280                 285

Phe Lys Tyr Val Phe Asp Tyr His Pro Gly Asp Ile Tyr Trp Cys Thr
    290                 295                 300

Ala Asp Val Gly Trp Val Thr Gly His Ser Tyr Leu Leu Tyr Gly Pro
305                 310                 315                 320
```

Leu Ala Cys Gly Ala Thr Thr Leu Met Phe Glu Gly Val Pro Asn Trp
                325                 330                 335

Pro Thr Pro Ala Arg Met Ala Gln Val Val Asp Lys His Gln Val Asn
            340                 345                 350

Ile Leu Tyr Thr Ala Pro Thr Ala Ile Arg Ala Leu Met Ala Glu Gly
        355                 360                 365

Asp Lys Ala Ile Glu Gly Thr Asp Arg Ser Ser Leu Arg Ile Leu Gly
    370                 375                 380

Ser Val Gly Glu Pro Ile Asn Pro Glu Ala Trp Glu Trp Tyr Trp Lys
385                 390                 395                 400

Lys Ile Gly Asn Glu Lys Cys Pro Val Val Asp Thr Trp Trp Gln Thr
                405                 410                 415

Glu Thr Gly Gly Phe Met Ile Thr Pro Leu Pro Gly Ala Thr Glu Leu
            420                 425                 430

Lys Ala Gly Ser Ala Thr Arg Pro Phe Phe Gly Val Gln Pro Ala Leu
        435                 440                 445

Val Asp Asn Glu Gly Asn Pro Leu Glu Gly Ala Thr Glu Gly Ser Leu
    450                 455                 460

Val Ile Thr Asp Ser Trp Pro Gly Gln Ala Arg Thr Leu Phe Gly Asp
465                 470                 475                 480

His Glu Arg Phe Glu Gln Thr Tyr Phe Ser Thr Phe Lys Asn Met Tyr
                485                 490                 495

Phe Ser Gly Asp Gly Ala Arg Arg Asp Glu Asp Gly Tyr Tyr Trp Ile
            500                 505                 510

Thr Gly Arg Val Asp Asp Val Leu Asn Val Ser Gly His Arg Leu Gly
        515                 520                 525

Thr Ala Glu Ile Glu Ser Ala Leu Val Ala His Pro Lys Ile Ala Glu
    530                 535                 540

Ala Ala Val Val Gly Ile Pro His Asn Ile Lys Gly Gln Ala Ile Tyr
545                 550                 555                 560

Ala Tyr Val Thr Leu Asn His Gly Glu Glu Pro Ser Pro Glu Leu Tyr
                565                 570                 575

Ala Glu Val Arg Asn Trp Val Arg Lys Glu Ile Gly Pro Leu Ala Thr
            580                 585                 590

Pro Asp Val Leu His Trp Thr Asp Ser Leu Pro Lys Thr Arg Ser Gly
        595                 600                 605

Lys Ile Met Arg Arg Ile Leu Arg Lys Ile Ala Ala Gly Asp Thr Ser
    610                 615                 620

Asn Leu Gly Asp Thr Ser Thr Leu Ala Asp Pro Gly Val Val Glu Lys
625                 630                 635                 640

Leu Leu Glu Glu Lys Gln Ala Ile Ala Met Pro Ser
                645                 650

<210> SEQ ID NO 10
<211> LENGTH: 645
<212> TYPE: PRT
<213> ORGANISM: Pseudomonas fulva

<400> SEQUENCE: 10

Met Ser Leu Pro His Arg Tyr Pro Val Ser Asp Ala Ala Arg Gln Arg
1               5                   10                  15

Thr His Leu Asp Asp Thr Ala Tyr Gln Arg Leu Tyr Arg Gln Ser Val
            20                  25                  30

Asp Asp Pro Gln Thr Phe Trp Gly Glu Gln Ala Lys Ala Phe Leu Asp

```
                35                  40                  45
Trp Phe Lys Pro Trp Asp Glu Val Cys Ser Gly Ser Leu Ser Lys Gly
 50                  55                  60

Asp Ile Arg Trp Phe Ser Gly Gln Leu Asn Ile Ser His Asn Cys
 65                  70                  75                  80

Ile Asp Arg His Leu Ala Lys Arg Gly Asp Gln Val Ala Leu Ile Trp
                 85                  90                  95

Glu Gly Asp Asp Pro Met Asp Ser Ala Arg Ile Thr Tyr Arg Glu Leu
                100                 105                 110

His Glu Gln Val Cys Arg Leu Ala Asn Val Leu Lys Ser Arg Gly Val
            115                 120                 125

Lys Lys Gly Asp Arg Val Cys Ile Tyr Met Pro Met Val Pro Gln Ala
        130                 135                 140

Ala Tyr Ala Met Leu Ala Cys Thr Arg Ile Gly Ala Val His Ser Val
145                 150                 155                 160

Val Phe Gly Gly Phe Ser Pro Asp Ala Leu Arg Asp Arg Ile Leu Asp
                165                 170                 175

Ala Asp Cys Arg Thr Val Ile Thr Ala Asp Glu Ala Val Arg Gly Gly
            180                 185                 190

Lys Leu Ile Pro Leu Lys Ser Asn Val Asp Lys Ala Leu Ala Ser Cys
        195                 200                 205

Pro Asn Val Ser Thr Val Leu Val Val Lys Arg Thr Gly Asn Lys Val
210                 215                 220

Asp Trp Asp Asp Lys Arg Asp Leu Trp Tyr Ala Glu Ala Val Gln Gln
225                 230                 235                 240

Ala Gly Ala Asp Cys Pro Ala Glu Pro Met Asp Ala Glu Asp Pro Leu
                245                 250                 255

Phe Ile Leu Tyr Thr Ser Gly Ser Thr Gly Lys Pro Lys Gly Val Leu
                260                 265                 270

His Ser Thr Ala Gly Tyr Leu Leu Gln Ala Ala Met Thr His Lys Tyr
            275                 280                 285

Val Phe Asp Tyr His Asp Gly Asp Ile Tyr Trp Cys Thr Ala Asp Val
        290                 295                 300

Gly Trp Val Thr Gly His Ser Tyr Ile Val Tyr Gly Pro Leu Ala Asn
305                 310                 315                 320

Gly Ala Thr Ser Leu Ile Phe Glu Gly Val Pro Asn Tyr Pro Asp Thr
                325                 330                 335

Ser Arg Phe Trp Gln Val Ile Asp Lys His Gln Val Asn Ile Phe Tyr
                340                 345                 350

Thr Ala Pro Thr Ala Leu Arg Ala Leu Met Arg Glu Gly Glu Ala Pro
            355                 360                 365

Val Lys Lys Ala Ser Arg Ser Ser Leu Arg Leu Leu Gly Ser Val Gly
        370                 375                 380

Glu Pro Ile Asn Pro Glu Ala Trp Glu Trp Tyr Phe Lys Val Val Gly
385                 390                 395                 400

Glu Gln Arg Cys Pro Ile Val Asp Thr Trp Trp Gln Thr Glu Thr Gly
                405                 410                 415

Ala Ile Met Ile Thr Pro Leu Pro Gly Ala Thr Asp Leu Lys Pro Gly
                420                 425                 430

Ser Ala Thr Arg Pro Phe Phe Gly Val Gln Pro Val Leu Leu Asp Glu
            435                 440                 445

Gln Gly Lys Glu Ile Asp Gly Pro Gly Ala Gly Val Leu Ala Ile Lys
        450                 455                 460
```

```
Ala Ser Trp Pro Ser Gln Ile Arg Ser Val Tyr Gly Asp His Lys Arg
465                 470                 475                 480

Met Leu Glu Thr Tyr Phe Thr Ala Tyr Pro Gly Tyr Tyr Phe Ser Gly
            485                 490                 495

Asp Gly Ala Arg Arg Asp Glu Asp Gly Tyr Trp Trp Ile Thr Gly Arg
            500                 505                 510

Ile Asp Asp Val Ile Asn Val Ser Gly His Arg Ile Gly Thr Ala Glu
                515                 520                 525

Val Glu Ser Ala Leu Val Leu His Asp Ala Val Ala Glu Ala Ala Val
            530                 535                 540

Val Gly Tyr Pro His Asp Val Lys Gly Gln Gly Ile Tyr Ala Phe Val
545                 550                 555                 560

Thr Thr Met Asn Gly Val Glu Pro Ser Asp Glu Leu Lys Lys Glu Leu
                565                 570                 575

Leu Ser Leu Val Gly Lys Glu Ile Gly Asn Phe Ala Lys Pro Glu Leu
            580                 585                 590

Ile Gln Trp Ala Pro Gly Leu Pro Lys Thr Arg Ser Gly Lys Ile Met
            595                 600                 605

Arg Arg Ile Leu Arg Lys Ile Ala Cys Asn Glu Leu Asp Ser Leu Gly
610                 615                 620

Asp Thr Ser Thr Leu Ala Asp Pro Ser Val Val Asp Ser Leu Ile Glu
625                 630                 635                 640

Gln Arg Val Asn Asn
                645

<210> SEQ ID NO 11
<211> LENGTH: 1080
<212> TYPE: DNA
<213> ORGANISM: Sulfolobus tokodaii

<400> SEQUENCE: 11
gtgatactca tgaggagaac attaaaagcc gcaatattag gtgctactgg tttagtagga     60
atcgaatacg taagaatgct atcaaatcat ccttatatta aaccagcata tttagctgga    120
aaaggttcag tgggtaaacc gtatggtgag gtagtaagat ggcaaacagt aggacaagtt    180
cctaaggaaa tagctgatat ggaaataaaa ccaactgatc ctaagttaat ggatgatgta    240 gacataaatat tttctccatt acctcaaggt gctgctggcc cagtagaaga caaatttgca    300
aaagaaggat tccctgtgat tagtaattca ccagatcata gatttgatcc tgatgttccc    360
ttattggttc ctgaactaaa tcctcatact attagcttaa ttgatgagca agaaaaaga     420 agagaatgga aggatttat agtaactaca ccactatgca cagcccaggg tgcagcaata    480
ccattaggtg ctatatttaa agattataag atggatggag catttataac tactattcaa    540
tcgctatctg gtgccggtta tccaggaata ccatcattag atgtagtaga taatatcttg    600
cctttaggtg atggatacga tgccaagacg ataaaagaga tcttcagaat tttaagcgaa    660
gttaagagaa atgtagatga acctaaatta gaagatgtaa gcttagcagc aacaactcat    720
agaatagcta ctatacatgg tcattatgaa gtactatatg tatcgttcaa agaggaaact    780
gctgctgaaa aagttaagga actttagaa aactttagag gggaaccaca agatctaaaa    840
ttaccaactg caccttcaaa gccaattatc gttatgaatg aggatacaag acctcaagtc    900
tattttgata gatgggctgg ggatattcca ggaatgagtg tagttgtagg tagattaaag    960
caagtgaata gagaatgat aaggttagta tcattaattc ataacacggt cagaggagcc   1020
```
gcaggaggag gtatattagc agctgaatta cttgtcgaaa aaggatatat tgaaaagtaa    1080

<210> SEQ ID NO 12
<211> LENGTH: 1071
<212> TYPE: DNA
<213> ORGANISM: Artificial Sequence
<220> FEATURE:
<223> OTHER INFORMATION: Codon-optimized coding sequence for Sulfolobus
      tokodaii malonate semialdehyde reductase

<400> SEQUENCE: 12

```
atgcgtcgca cacttaaagc cgcgattctg ggcgcaaccg gtctcgtggg gatcgaatac      60
gtgcgtatgc tcagtaacca ccctacatt aaaccggcgt atttagcagg taaaggtagc     120
gtcggtaaac cctatggtga ggtggtccgc tggcaaactg ttggtcaggt accgaaagaa    180
attgctgata tggagattaa acccacggat cccaaactga tggatgatgt ggatatcatt    240
tttagcccccc ttccccaagg tgccgcgggt ccagtggaag aacaattcgc caaggaaggc    300
ttcccagtca tcagtaactc cccggaccac cgttttgatc ccgatgtccc gctcctcgtg    360
cccgaattga atccccacac catttccctc atcgatgaac agcgaaagcg acgcgagtgg    420
aagggcttca ttgttaccac acctctgtgt accgcccaag gggcggcgat tcccttaggt    480
gcgattttca aagactataa aatggatggc gcctttatta ctaccatcca atccctcagt    540
ggggctggct atcccggtat tccgagtctg gatgtggtcg acaacatttt accgctgggg    600
gatggttatg acgctaaaac cattaaagaa atttttcgca tcttatcgga ggttaaacgg    660
aatgttgacg aacccaaact tgaagatgtc tcgttagccg cgaccactca tcggattgct    720
acgattcatg gtcattatga ggtcctctat gtgtccttca agaagaaac cgcggcagaa    780
aaagtgaaag agaccttaga aaattttcga ggggagcctc aagatctgaa actgccgacc    840
gcacccagta aacccatcat tgtaatgaac gaagacacgc ggccacaggt ttactttgat    900
cgttgggccg cgatatccc cgggatgtct gtcgtggtgg ggcgtttgaa acaagtaaat    960
aagcgcatga ttcggctggt gtccttaatc acaacactg tacgcggtgc tgcgggcggt   1020
ggcatcctgg cggccgaact gttggtggag aaaggctaca ttgaaaaata a            1071
```

<210> SEQ ID NO 13
<211> LENGTH: 359
<212> TYPE: PRT
<213> ORGANISM: Sulfolobus tokodaii

<400> SEQUENCE: 13

Met Ile Leu Met Arg Arg Thr Leu Lys Ala Ala Ile Leu Gly Ala Thr
1               5                   10                  15

Gly Leu Val Gly Ile Glu Tyr Val Arg Met Leu Ser Asn His Pro Tyr
            20                  25                  30

Ile Lys Pro Ala Tyr Leu Ala Gly Lys Gly Ser Val Gly Lys Pro Tyr
        35                  40                  45

Gly Glu Val Val Arg Trp Gln Thr Val Gly Gln Val Pro Lys Glu Ile
    50                  55                  60

Ala Asp Met Glu Ile Lys Pro Thr Asp Pro Lys Leu Met Asp Asp Val
65                  70                  75                  80

Asp Ile Ile Phe Ser Pro Leu Pro Gln Gly Ala Ala Gly Pro Val Glu
                85                  90                  95

Glu Gln Phe Ala Lys Glu Gly Phe Pro Val Ile Ser Asn Ser Pro Asp
            100                 105                 110

His Arg Phe Asp Pro Asp Val Pro Leu Leu Val Pro Glu Leu Asn Pro

|   | 115 |   |   |   | 120 |   |   |   |   | 125 |   |   |
|---|---|---|---|---|---|---|---|---|---|---|---|---|

His Thr Ile Ser Leu Ile Asp Glu Gln Arg Lys Arg Arg Glu Trp Lys
     130                 135                 140

Gly Phe Ile Val Thr Thr Pro Leu Cys Thr Ala Gln Gly Ala Ala Ile
145                 150                 155                 160

Pro Leu Gly Ala Ile Phe Lys Asp Tyr Lys Met Asp Gly Ala Phe Ile
                165                 170                 175

Thr Thr Ile Gln Ser Leu Ser Gly Ala Gly Tyr Pro Gly Ile Pro Ser
            180                 185                 190

Leu Asp Val Val Asp Asn Ile Leu Pro Leu Gly Asp Gly Tyr Asp Ala
        195                 200                 205

Lys Thr Ile Lys Glu Ile Phe Arg Ile Leu Ser Glu Val Lys Arg Asn
    210                 215                 220

Val Asp Glu Pro Lys Leu Glu Asp Val Ser Leu Ala Ala Thr Thr His
225                 230                 235                 240

Arg Ile Ala Thr Ile His Gly His Tyr Glu Val Leu Tyr Val Ser Phe
                245                 250                 255

Lys Glu Glu Thr Ala Ala Glu Lys Val Lys Glu Thr Leu Glu Asn Phe
            260                 265                 270

Arg Gly Glu Pro Gln Asp Leu Lys Leu Pro Thr Ala Pro Ser Lys Pro
        275                 280                 285

Ile Ile Val Met Asn Glu Asp Thr Arg Pro Gln Val Tyr Phe Asp Arg
    290                 295                 300

Trp Ala Gly Asp Ile Pro Gly Met Ser Val Val Gly Arg Leu Lys
305                 310                 315                 320

Gln Val Asn Lys Arg Met Ile Arg Leu Val Ser Leu Ile His Asn Thr
                325                 330                 335

Val Arg Gly Ala Ala Gly Gly Gly Ile Leu Ala Ala Glu Leu Leu Val
            340                 345                 350

Glu Lys Gly Tyr Ile Glu Lys
        355

<210> SEQ ID NO 14
<211> LENGTH: 945
<212> TYPE: DNA
<213> ORGANISM: Metallosphaera sedula

<400> SEQUENCE: 14

```
atgactgaaa aggtatctgt agttggagca ggagttatag gcgtaggttg ggcgacccct     60
tttgcgtcta agggatacag cgtctctctc tacaccgaaa agaaggaaac cctagacaag    120
ggaatagaga agctaaggaa ctacgttcag gtgatgaaga caactcccca gataaccgag    180
gacgtcaata ccgtgatctc gagggtttct cccaccacga atctggatga ggccgttagg    240
ggagccaact tcgtcattga ggcagttatt gaggattatg acgcaaaaaa gaaaatcttt    300
ggatacttgg acagcgtcct tgacaaggag gttatactag ctagcagtac ttcaggtctc    360
ctcataacag aggttcagaa ggcaatgtcc aagcaccctg agagggcggt gatagcccat    420
ccctggaatc cacccacct tctaccgctt gtcgagatag ttccaggaga aagaccagt     480
atggaagtgg tggagaggac gaagtccctc atggagaagc tggacagaat agtagtggtg    540
ctcaagaagg agattccggg tttcataggg aacaggctcg cctttgctct tttccgagag    600
gccgtatacc ttgtagacga gggtgtggcc actgtggagg acatcgacaa ggtaatgaca    660
gcggcaattg gactcagatg ggccttcatg ggtccgttcc tcacatacca tctaggtggt    720
```

```
ggagaaggag ggcttgagta cttctttaat aggggttttg ggtacggtgc taacgaatgg      780
atgcataccc tggcaaaata cgacaagttc ccctacactg gggttacgaa agcgatacag      840
caaatgaagg aatactcctt cataaagggt aagactttcc aggaaatttc gaagtggagg      900
gacgaaaagc tcctgaaggt atacaaacta gtttgggaaa ataa                       945
```

<210> SEQ ID NO 15
<211> LENGTH: 945
<212> TYPE: DNA
<213> ORGANISM: Artificial Sequence
<220> FEATURE:
<223> OTHER INFORMATION: Codon-optimized coding sequence for
      Metallosphaera sedula malonyl-CoA reductase

<400> SEQUENCE: 15

```
atgaccgaaa agtatctgt cgtgggtgct ggggtgatcg gcgttggatg ggccacccttt     60 tttgccagca agggtattc cgtcagtttg tataccgaaa aaaagaaac actcgataaa       120 ggaattgaaa actgcggaa ctatgtgcag gtgatgaaaa ataatagcca atcacggaa       180 gatgtcaata ccgtgattag tcgcgtgtcc cctaccacca atttggatga agccgttcgc    240
ggcgcgaact tcgttatcga agccgtcatt gaagactatg atgccaagaa aaaaattttt    300
ggatacctcg atagtgttct cgataaagaa gttatttgg cttcgtccac aagcgggctc    360
ttgattacag aagttcaaaa agcgatgtct aaacatcccg aacgcgcggt gattgcacat    420
ccttggaatc caccccacct gctgcccttg gtcgaaatcg ttcccggaga aaaaaccagc    480
atggaggtcg tcgaacgcac gaaatccctc atggaaaaaac tcgatcgcat cgtggtggtc    540
ctcaaaaaag aaattcctgg tttttatcggc aatcgtctcg cctttgcatt attccgtgaa    600
gccgtctacc tggttgatga gggggtggcg accgtggaag atatcgataa agtaatgacc    660
gccgcgattg gattacggtg ggcctttatg ggcccatttc tcacctacca cctcggtggc    720
ggggaaggcg gtttggaata tttttttaac cggggctttg gctatggcgc aaatgaatgg    780
atgcataccc ttgccaaata tgataagttt ccctatactg gtgtaaccaa ggccattcaa    840
caaatgaagg aatactcgtt tattaagggt aaaacgttcc aggaaatctc caaatggcgg    900
gatgagaaac tcttaaaagt ctacaaactg gtctgggaaa ataa                     945
```

<210> SEQ ID NO 16
<211> LENGTH: 314
<212> TYPE: PRT
<213> ORGANISM: Metallosphaera sedula

<400> SEQUENCE: 16

```
Met Thr Glu Lys Val Ser Val Gly Ala Gly Val Ile Gly Val Gly
1               5                   10                  15

Trp Ala Thr Leu Phe Ala Ser Lys Gly Tyr Ser Val Ser Leu Tyr Thr
            20                  25                  30

Glu Lys Lys Glu Thr Leu Asp Lys Gly Ile Glu Lys Leu Arg Asn Tyr
        35                  40                  45

Val Gln Val Met Lys Asn Asn Ser Gln Ile Thr Glu Asp Val Asn Thr
    50                  55                  60

Val Ile Ser Arg Val Ser Pro Thr Thr Asn Leu Asp Glu Ala Val Arg
65                  70                  75                  80

Gly Ala Asn Phe Val Ile Glu Ala Val Ile Glu Asp Tyr Asp Ala Lys
                85                  90                  95

Lys Lys Ile Phe Gly Tyr Leu Asp Ser Val Leu Asp Lys Glu Val Ile
            100                 105                 110
```

Leu Ala Ser Ser Thr Ser Gly Leu Leu Ile Thr Glu Val Gln Lys Ala
        115                 120                 125

Met Ser Lys His Pro Glu Arg Ala Val Ile Ala His Pro Trp Asn Pro
    130                 135                 140

Pro His Leu Leu Pro Leu Val Glu Ile Val Pro Gly Glu Lys Thr Ser
145                 150                 155                 160

Met Glu Val Val Glu Arg Thr Lys Ser Leu Met Glu Lys Leu Asp Arg
                165                 170                 175

Ile Val Val Leu Lys Lys Glu Ile Pro Gly Phe Ile Gly Asn Arg
            180                 185                 190

Leu Ala Phe Ala Leu Phe Arg Glu Ala Val Tyr Leu Val Asp Glu Gly
        195                 200                 205

Val Ala Thr Val Glu Asp Ile Asp Lys Val Met Thr Ala Ala Ile Gly
    210                 215                 220

Leu Arg Trp Ala Phe Met Gly Pro Phe Leu Thr Tyr His Leu Gly Gly
225                 230                 235                 240

Gly Glu Gly Gly Leu Glu Tyr Phe Phe Asn Arg Gly Phe Gly Tyr Gly
                245                 250                 255

Ala Asn Glu Trp Met His Thr Leu Ala Lys Tyr Asp Lys Phe Pro Tyr
            260                 265                 270

Thr Gly Val Thr Lys Ala Ile Gln Gln Met Lys Glu Tyr Ser Phe Ile
        275                 280                 285

Lys Gly Lys Thr Phe Gln Glu Ile Ser Lys Trp Arg Asp Glu Lys Leu
        290                 295                 300

Leu Lys Val Tyr Lys Leu Val Trp Glu Lys
305                 310

<210> SEQ ID NO 17
<211> LENGTH: 966
<212> TYPE: DNA
<213> ORGANISM: Bacillus subtilis

<400> SEQUENCE: 17
atgatgaaca acatgtaaa taaagtagct ttaatcggag cgggttttgt tggaagcagt      60
tatgcatttg cgttaattaa ccaaggaatc acagatgagc ttgtggtcat tgatgtaaat     120
aaagaaaaag caatgggcga tgtgatggat ttaaaccacg aaaggcgtt tgcgccacaa     180
ccggtcaaaa catcttacgg aacatatgaa gactgcaagg atgctgatat tgtctgcatt     240
tgcgccggag caaccaaaa acctggtgag cacacgcctg aattagtaga aaagaacttg     300
aagattttca aaggcatcgt tagtgaagtc atggcgagcg gatttgacgg cattttctta     360
gtcgcgacaa atccggttga tatcctgact tacgcaacat ggaaattcag cggcctgcca     420
aaagagcggg tgattggaag cggcacaaca cttgattctg cgagattccg tttcatgctg     480
agcgaatact ttggcgcagc gcctcaaaac gtacacgcgc atattatcgg agagcacggc     540
gacacagagc ttcctgtttg gagccacgcg aatgtcggcg gtgtgccggt cagtgaactc     600
gttgagaaaa acgatgcgta caaacaagag gagctggacc aaattgtaga tgatgtgaaa     660
aacgcagctt accatatcat tgagaaaaaa ggcgcgactt attatggggt tgcgatgagt     720
cttgctcgca ttacaaaagc cattcttcat aatgaaaaca gcatattaac tgtcagcaca     780
tatttggacg gcaatacgg tgcagatgac gtgtacatcg gtgtgccggc tgtcgtgaat     840
cgcggaggga tcgcaggtat cactgagctg aacttaaatg agaaagaaaa agaacagttc     900
cttcacagcg ccggcgtcct taaaaacatt ttaaaacctc attttgcaga acaaaaagtc     960
aactaa 966

<210> SEQ ID NO 18
<211> LENGTH: 321
<212> TYPE: PRT
<213> ORGANISM: Bacillus subtilis

<400> SEQUENCE: 18

Met Met Asn Lys His Val Asn Lys Val Ala Leu Ile Gly Ala Gly Phe
1               5                   10                  15

Val Gly Ser Ser Tyr Ala Phe Ala Leu Ile Asn Gln Gly Ile Thr Asp
            20                  25                  30

Glu Leu Val Val Ile Asp Val Asn Lys Glu Lys Ala Met Gly Asp Val
        35                  40                  45

Met Asp Leu Asn His Gly Lys Ala Phe Ala Pro Gln Pro Val Lys Thr
    50                  55                  60

Ser Tyr Gly Thr Tyr Glu Asp Cys Lys Asp Ala Asp Ile Val Cys Ile
65                  70                  75                  80

Cys Ala Gly Ala Asn Gln Lys Pro Gly Glu Thr Arg Leu Glu Leu Val
                85                  90                  95

Glu Lys Asn Leu Lys Ile Phe Lys Gly Ile Val Ser Glu Val Met Ala
            100                 105                 110

Ser Gly Phe Asp Gly Ile Phe Leu Val Ala Thr Asn Pro Val Asp Ile
        115                 120                 125

Leu Thr Tyr Ala Thr Trp Lys Phe Ser Gly Leu Pro Lys Glu Arg Val
    130                 135                 140

Ile Gly Ser Gly Thr Thr Leu Asp Ser Ala Arg Phe Arg Phe Met Leu
145                 150                 155                 160

Ser Glu Tyr Phe Gly Ala Ala Pro Gln Asn Val His Ala His Ile Ile
                165                 170                 175

Gly Glu His Gly Asp Thr Glu Leu Pro Val Trp Ser His Ala Asn Val
            180                 185                 190

Gly Gly Val Pro Val Ser Glu Leu Val Glu Lys Asn Asp Ala Tyr Lys
        195                 200                 205

Gln Glu Glu Leu Asp Gln Ile Val Asp Asp Val Lys Asn Ala Ala Tyr
    210                 215                 220

His Ile Ile Glu Lys Lys Gly Ala Thr Tyr Tyr Gly Val Ala Met Ser
225                 230                 235                 240

Leu Ala Arg Ile Thr Lys Ala Ile Leu His Asn Glu Asn Ser Ile Leu
                245                 250                 255

Thr Val Ser Thr Tyr Leu Asp Gly Gln Tyr Gly Ala Asp Asp Val Tyr
            260                 265                 270

Ile Gly Val Pro Ala Val Val Asn Arg Gly Gly Ile Ala Gly Ile Thr
        275                 280                 285

Glu Leu Asn Leu Asn Glu Lys Glu Lys Glu Gln Phe Leu His Ser Ala
    290                 295                 300

Gly Val Leu Lys Asn Ile Leu Lys Pro His Phe Ala Glu Gln Lys Val
305                 310                 315                 320

Asn

<210> SEQ ID NO 19
<211> LENGTH: 1401
<212> TYPE: DNA
<213> ORGANISM: Escherichia coli

<400> SEQUENCE: 19

```
atgccacatt cctacgatta cgatgccata gtaataggtt ccggccccgg cggcgaaggc    60
gctgcaatgg gcctggttaa gcaaggtgcg cgcgtcgcag ttatcgagcg ttatcaaaat   120
gttggcggcg gttgcaccca ctggggcacc atcccgtcga agctctccg tcacgccgtc   180
agccgcatta tagaattcaa tcaaaaccca ctttacagcg accattcccg actgctccgc   240
tcttcttttg ccgatatcct taaccatgcc gataacgtga ttaatcaaca aacgcgcatg   300
cgtcaggat tttacgaacg taatcactgt gaaatattgc agggaaacgc tcgctttgtt   360
gacgagcata cgttggcgct ggattgcccg gacggcagcg ttgaaacact aaccgctgaa   420
aaatttgtta ttgcctgcgg ctctcgtcca tatcatccaa cagatgttga tttcacccat   480
ccacgcattt acgacagcga ctcaattctc agcatgcacc acgaaccgcg ccatgtactt   540
atctatggtg ctggagtgat cggctgtgaa atgcgtcga tcttccgcgg tatggatgta   600
aaagtggatc tgatcaacac ccgcgatcgc ctgctggcat ttctcgatca agagatgtca   660
gattctctct cctatcactt ctggaacagt ggcgtagtga ttcgtcacaa cgaagagtac   720
gagaagatcg aaggctgtga cgatggtgtg atcatgcatc tgaagtcggg taaaaaactg   780
aaagctgact gcctgctcta tgccaacggt cgcaccggta taccgattc gctggcgtta   840
cagaacattg ggctagaaac tgacagccgc ggacagctga aggtcaacag catgtatcag   900
accgcacagc cacacgtttta cgcggtgggc gacgtgattg ttatccgag cctggcgtcg   960
gcggcctatg accaggggcg cattgccgcg caggcgctgg taaaaggcga agccaccgca  1020
catctgattg aagatatccc taccggtatt tacaccatcc cggaaatcag ctctgtgggc  1080
aaaaccgaac agcagctgac cgcaatgaaa gtgccatatg aagtgggccg cgcccagttt  1140
aaacatctgg cacgcgcaca atcgtcggc atgaacgtgg gcacgctgaa aatttttgttc  1200
catcgggaaa caaaagagat tctgggtatt cactgctttg gcgagcgcgc tgccgaaatt  1260
attcatatcg gtcaggcgat tatggaacag aaaggtggcg gcaacactat tgagtacttc  1320
gtcaacacca cctttaacta cccgacgatg gcggaagcct atcgggtagc tgcgttaaac  1380
ggtttaaacc gcctgttcta a                                             1401
```

<210> SEQ ID NO 20
<211> LENGTH: 466
<212> TYPE: PRT
<213> ORGANISM: Escherichia coli

<400> SEQUENCE: 20

```
Met Pro His Ser Tyr Asp Tyr Asp Ala Ile Val Ile Gly Ser Gly Pro
1               5                   10                  15

Gly Gly Glu Gly Ala Ala Met Gly Leu Val Lys Gln Gly Ala Arg Val
            20                  25                  30

Ala Val Ile Glu Arg Tyr Gln Asn Val Gly Gly Gly Cys Thr His Trp
        35                  40                  45

Gly Thr Ile Pro Ser Lys Ala Leu Arg His Ala Val Ser Arg Ile Ile
    50                  55                  60

Glu Phe Asn Gln Asn Pro Leu Tyr Ser Asp His Ser Arg Leu Leu Arg
65                  70                  75                  80

Ser Ser Phe Ala Asp Ile Leu Asn His Ala Asp Asn Val Ile Asn Gln
                85                  90                  95

Gln Thr Arg Met Arg Gln Gly Phe Tyr Glu Arg Asn His Cys Glu Ile
            100                 105                 110
```

```
Leu Gln Gly Asn Ala Arg Phe Val Asp Glu His Thr Leu Ala Leu Asp
            115                 120                 125

Cys Pro Asp Gly Ser Val Glu Thr Leu Thr Ala Glu Lys Phe Val Ile
130                 135                 140

Ala Cys Gly Ser Arg Pro Tyr His Pro Thr Asp Val Asp Phe Thr His
145                 150                 155                 160

Pro Arg Ile Tyr Asp Ser Asp Ser Ile Leu Ser Met His His Glu Pro
                165                 170                 175

Arg His Val Leu Ile Tyr Gly Ala Gly Val Ile Gly Cys Glu Tyr Ala
            180                 185                 190

Ser Ile Phe Arg Gly Met Asp Val Lys Val Asp Leu Ile Asn Thr Arg
            195                 200                 205

Asp Arg Leu Leu Ala Phe Leu Asp Gln Glu Met Ser Asp Ser Leu Ser
210                 215                 220

Tyr His Phe Trp Asn Ser Gly Val Val Ile Arg His Asn Glu Glu Tyr
225                 230                 235                 240

Glu Lys Ile Glu Gly Cys Asp Asp Gly Val Ile Met His Leu Lys Ser
                245                 250                 255

Gly Lys Lys Leu Lys Ala Asp Cys Leu Leu Tyr Ala Asn Gly Arg Thr
            260                 265                 270

Gly Asn Thr Asp Ser Leu Ala Leu Gln Asn Ile Gly Leu Glu Thr Asp
            275                 280                 285

Ser Arg Gly Gln Leu Lys Val Asn Ser Met Tyr Gln Thr Ala Gln Pro
290                 295                 300

His Val Tyr Ala Val Gly Asp Val Ile Gly Tyr Pro Ser Leu Ala Ser
305                 310                 315                 320

Ala Ala Tyr Asp Gln Gly Arg Ile Ala Ala Gln Ala Leu Val Lys Gly
                325                 330                 335

Glu Ala Thr Ala His Leu Ile Glu Asp Ile Pro Thr Gly Ile Tyr Thr
            340                 345                 350

Ile Pro Glu Ile Ser Ser Val Gly Lys Thr Gln Gln Leu Thr Ala
            355                 360                 365

Met Lys Val Pro Tyr Glu Val Gly Arg Ala Gln Phe Lys His Leu Ala
370                 375                 380

Arg Ala Gln Ile Val Gly Met Asn Val Gly Thr Leu Lys Ile Leu Phe
385                 390                 395                 400

His Arg Glu Thr Lys Glu Ile Leu Gly Ile His Cys Phe Gly Glu Arg
                405                 410                 415

Ala Ala Glu Ile Ile His Ile Gly Gln Ala Ile Met Glu Gln Lys Gly
            420                 425                 430

Gly Gly Asn Thr Ile Glu Tyr Phe Val Asn Thr Thr Phe Asn Tyr Pro
            435                 440                 445

Thr Met Ala Glu Ala Tyr Arg Val Ala Ala Leu Asn Gly Leu Asn Arg
450                 455                 460

Leu Phe
465

<210> SEQ ID NO 21
<211> LENGTH: 978
<212> TYPE: DNA
<213> ORGANISM: Lactococcus lactis

<400> SEQUENCE: 21
atggcggata agcaacgcaa aaaagtgatt ttggttggtg acggggcagt tggttcgtcg      60
```

```
tatgcgtttg ccctggtaaa ccaaggtatc gcccaagaat taggcatcgt tgacttgttc    120
aaagaaaaaa cccagggaga tgccgaagac ctctctcacg ccttagcctt caccagccct    180
aaaaaatttt atagtgctga ttatagtgat gcgtccgacg ccgatctcgt ggttcttacc    240
agcggtgccc cccagaagcc cggtgaaacc cggttagatc tcgttgaaaa gaatctgcga    300
attaccaaag atgttgttac taagatcgtg gcgtctggct ttaagggat ttttctcgtc     360 gcggctaacc cagtggacat cctcacgtat gctacgtgga agtttagtgg ttttcccaag    420
aaccgagtgg tcggctctgg caccagcctc gataccgccc gtttccggca ggccttggct    480
gagaaggtcg atgtcgacgc ccggtcgatt cacgcgtaca ttatgggtga acatggtgac    540
agtgaatttg cagtctggag tcacgccaat gtggccggcg tgaaactgga acaatggttc    600
caagaaaatg attacctgaa tgaagccgaa attgtggagt tatttgaaag cgtgcgggat    660
gccgcctatt ctattatcgc caaaaagggg gccacgtttt atggagtcgc agtcgcactt    720
gcgcgcatta ccaaggccat tctggacgat gaacacgccg ttctcccggt gagtgtgttt    780
caagatggtc aatacggcgt gtctgattgt tatctcgggc aacccgccgt tgtgggtgca    840
gaaggagtgg taaatcctat ccatatcccc ttgaacgatg ccgagatgca aagatggaa     900 gcctcgggcg cgcaattgaa agctattatt gatgaggcat tgctaagga ggaatttgcg     960 agcgcggtga aaattaa                                                   978
```

```
<210> SEQ ID NO 22
<211> LENGTH: 325
<212> TYPE: PRT
<213> ORGANISM: Lactococcus lactis

<400> SEQUENCE: 22

Met Ala Asp Lys Gln Arg Lys Val Ile Leu Val Gly Asp Gly Ala
1               5                   10                  15

Val Gly Ser Ser Tyr Ala Phe Ala Leu Val Asn Gln Gly Ile Ala Gln
                20                  25                  30

Glu Leu Gly Ile Val Asp Leu Phe Lys Glu Lys Thr Gln Gly Asp Ala
            35                  40                  45

Glu Asp Leu Ser His Ala Leu Ala Phe Thr Ser Pro Lys Lys Ile Tyr
        50                  55                  60

Ser Ala Asp Tyr Ser Asp Ala Ser Asp Ala Asp Leu Val Val Leu Thr
65                  70                  75                  80

Ser Gly Ala Pro Gln Lys Pro Gly Glu Thr Arg Leu Asp Leu Val Glu
                85                  90                  95

Lys Asn Leu Arg Ile Thr Lys Asp Val Val Thr Lys Ile Val Ala Ser
            100                 105                 110

Gly Phe Lys Gly Ile Phe Leu Val Ala Ala Asn Pro Val Asp Ile Leu
        115                 120                 125

Thr Tyr Ala Thr Trp Lys Phe Ser Gly Phe Pro Lys Asn Arg Val Val
130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
            180                 185                 190

Gly Val Lys Leu Glu Gln Trp Phe Gln Glu Asn Asp Tyr Leu Asn Glu
        195                 200                 205
```

-continued

```
Ala Glu Ile Val Glu Leu Phe Glu Ser Val Arg Asp Ala Ala Tyr Ser
    210                 215                 220

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
            245                 250                 255

Val Ser Val Phe Gln Asp Gly Gln Tyr Gly Val Ser Asp Cys Tyr Leu
            260                 265                 270

Gly Gln Pro Ala Val Val Gly Ala Glu Gly Val Val Asn Pro Ile His
        275                 280                 285

Ile Pro Leu Asn Asp Ala Glu Met Gln Lys Met Glu Ala Ser Gly Ala
    290                 295                 300

Gln Leu Lys Ala Ile Ile Asp Glu Ala Phe Ala Lys Glu Glu Phe Ala
305                 310                 315                 320

Ser Ala Val Lys Asn
            325
```

US 8,846,354 B1

MICROORGANISMS FOR PRODUCING ORGANIC ACIDS

CROSS-REFERENCE TO RELATED APPLICATIONS

This application is a continuation-in-part of U.S. patent application Ser. No. 13/798,835, filed Mar. 13, 2013, and claims priority under 35 USC §119(e) to U.S. Provisional Patent Application 61/647,001 filed May 15, 2012, the entireties of which are incorporated herein by reference. This application incorporates by reference co-filed U.S. patent application Ser. No. 14/200,686, which is also a continuation-in-part of U.S. patent application Ser. No. 13/798,835, filed Mar. 13, 2013, and claims priority under 35 USC §119(e) to U.S. Provisional Patent Application 61/647,001 filed May 15, 2012.

STATEMENT REGARDING FEDERALLY SPONSORED RESEARCH

This invention was made with government support under FA9550-11-1-0038 awarded by the USAF/AFOSR, DE-FC02-07ER64494 awarded by the US Department of Energy, and 1240268 awarded by the National Science Foundation. The government has certain rights in the invention.

FIELD OF THE INVENTION

The present invention relates to organic acid-tolerant microorganisms capable of producing organic acids and uses thereof for producing organic acids.

BACKGROUND

Production of industrially useful chemicals has conventionally focused on the use of petroleum-like compounds as starting materials. However, various factors have increased interest in the production of such chemicals through microorganism-mediated bioconversion of biomass and other renewable resources.

Accordingly, the U.S. Department of Energy (DOE) recently identified several "building block" chemicals to be produced via microorganism consumption of biomass. The identified chemicals include 1,4 succinic acid, fumaric and malic acids, 2,5 furan dicarboxylic acid, 3-hydroxypropionic acid (3HP), aspartic acid, glucaric acid, glutamic acid, itaconic acid, levulinic acid, 3-hydroxybutyrolactone, glycerol, sorbitol, and xylitol/arabinitol. These chemicals can be converted to high-value, bio-based chemicals or materials.

As an example, 3HP can be readily transformed into a variety of commodity chemicals such as acrylic acid, methyl acrylate, and 1,3-propanediol. These commodity chemicals represent a multi-billion dollar a year industry and are used in the production of plastics, coatings, and fibers. U.S. demand for acrylic acid in particular is growing, exceeding $1 \times 10^9$ kg/year. The current means of synthesizing acrylic acid include oxidation of propylene. A thermodynamically favorable pathway for microbial production of acrylic acid has not been identified.

One hurdle facing the microbial production of industrially useful chemicals is that many, including 3HP, are toxic to the microbes capable of producing them. Recently, efforts have been made not only to increase microbial output of the chemicals but also to increase microbial tolerance to the chemicals. Some of these efforts have focused on the production of 3HP in the heterotrophic microbe *Escherichia coli*. See, e.g., U.S. Pat. No. 8,048,624 to Lynch, U.S. Pub. 2011/0125118 to Lynch, U.S. Pub. 2010/0210017 to Gill et al., and Warnecke et al. *Metabolic Engineering* (2010) 12:241-250.

While focusing on chemical production in heterotrophic microorganisms is a valuable strategy, a potential problem is the availability of carbon and energy sources such as food-based commodities and/or sugars derived from lignocellulosic biomass. An attractive alternative is to use phototrophic microorganisms, such as cyanobacteria. These microorganisms can produce chemical products from $CO_2$ and light energy without relying on consumption of higher-value carbon sources that can be used for other purposes, such as producing food, fuel, or other certain chemicals.

There is a need for microorganisms capable of producing high yields of industrially useful chemicals and having increased tolerance against those chemicals. There is also a need for microorganisms that use non-food-based feedstock in such production.

SUMMARY OF THE INVENTION

The present invention addresses the aforementioned needs by providing microorganisms with increased tolerance to organic acids. The present invention also provides microorganisms modified to produce organic acids. Methods of producing organic acids with the microorganisms described herein are also provided.

A preferred version of the invention comprises an organic acid-tolerant microorganism that includes a modification that reduces or ablates AcsA activity or AcsA homolog activity in the microorganism. The modification confers an increased tolerance to organic acids compared to a corresponding microorganism not comprising the modification.

The modification is preferably a genetic modification. The genetic modification is preferably a genetic modification other than or in addition to one resulting in a W49L substitution in AcsA or a corresponding substitution in an AcsA homolog.

The microorganism is preferably a bacterium, more preferably a cyanobacterium, and most preferably a cyanobacterium selected from the group consisting of *Synechococcus* sp., *Prochlorococcus* sp., *Synechocystis* sp., and *Nostoc* sp.

The tolerance to the organic acid is preferably increased at least about 25-fold in the microorganism of the invention compared to a corresponding microorganism.

In preferred versions of the invention, the microorganism is further modified to increase production of an organic acid. The microorganism may be modified to increase production of 3-hydroxypropionic acid, lactic acid, and/or others.

A microorganism of the invention modified to increase production of 3-hydroxyprionic acid preferably comprises one or more recombinant nucleic acids configured to express an enzyme selected from the group consisting of a malonyl-CoA reductase and a malonate semialdehyde reductase, wherein the microorganism produces an increased amount of 3-hydroxypropionic acid compared to a corresponding microorganism not comprising the one or more recombinant nucleic acids.

The malonyl-CoA reductase is preferably a malonyl-CoA reductase from *Sulfolobus tokodaii* or a homolog thereof. The malonyl-CoA reductase from *Sulfolobus tokodaii* or the homolog thereof preferably comprises an amino acid sequence at least about 80% identical, more preferably at least about 90% identical, and most preferably at least about 95% identical to SEQ ID NO:13.

The malonate semialdehyde reductase is preferably a malonate semialdehyde reductase from *Metallosphaera sedula* or a homolog thereof. The malonate semialdehyde reductase from *Metallosphaera sedula* or the homolog thereof preferably comprises an amino acid sequence at least about 80% identical, more preferably at least about 90% identical, and most preferably at least about 95% identical to SEQ ID NO:16.

A microorganism of the invention modified to increase production of lactic acid preferably comprises one or more recombinant nucleic acids configured to express an enzyme selected from the group consisting of a lactate dehydrogenase and a pyridine nucleotide transhydrogenase, wherein the microorganism produces an increased amount of lactic acid compared to a corresponding microorganism not comprising the one or more recombinant nucleic acids.

The lactate dehydrogenase is may be a lactate dehydrogenase from *Bacillus subtilis* or a homolog thereof. The lactate dehydrogenase from *Bacillus subtilis* or the homolog thereof preferably comprises an amino acid sequence at least about 80% identical, more preferably at least about 90% identical, and most preferably at least about 95% identical to SEQ ID NO:18.

The lactate dehydrogenase is may also or alternatively be a lactate dehydrogenase from *Lactococcus lactis* or a homolog thereof. The lactate dehydrogenase from *Lactococcus lactis* or the homolog thereof preferably comprises an amino acid sequence at least about 80% identical, more preferably at least about 90% identical, and most preferably at least about 95% identical to SEQ ID NO:22.

The pyridine nucleotide transhydrogenase is preferably a soluble pyridine nucleotide transhydrogenase from *Escherichia coli* or a homolog thereof. The soluble pyridine nucleotide transhydrogenase from *Escherichia coli* or the homolog thereof preferably comprises an amino acid sequence at least about 80% identical, more preferably at least about 90% identical, and most preferably at least about 95% identical to SEQ ID NO:20.

The invention further provides methods of producing an organic acid. The methods comprise culturing one of the microorganisms as described herein.

The objects and advantages of the invention will appear more fully from the following detailed description of the preferred embodiment of the invention made in conjunction with the accompanying drawings.

BRIEF DESCRIPTION OF THE DRAWINGS

FIG. 2A depicts growth of *Synechococcus* sp. PCC 7002 at OD730 as a function of time in the presence of 5 mM dimethylsulfoniopropionate (DMSP).

FIG. 2B depicts growth of *Synechococcus* sp. PCC 7002 at OD730 as a function of time in the presence of 5 mM acrylic acid.

FIG. 2C depicts growth of a mutant pool of *Synechococcus* sp. PCC 7002 at OD730 as a function of time in the presence of 5 mM dimethylsulfoniopropionate (DMSP) and 5 mM acrylic acid.

DETAILED DESCRIPTION OF THE INVENTION

Figure 1A:
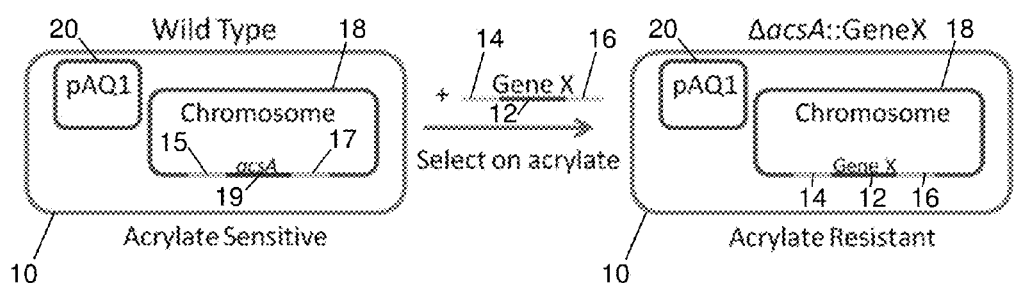
FIG. 1A depicts a schema for using acsA or a homolog thereof as a selection marker for introducing a DNA fragment of interest into the acsA or homolog chromosomal locus.

One version of the invention includes a microorganism wherein an acsA gene product or homolog thereof is functionally deleted. The acsA gene product (AcsA) and homologs thereof are acetyl-CoA synthetases classified under Enzyme Commission (EC) number 6.2.1.1. Other names for these acetyl-CoA synthetases include "acetate-CoA ligases," "acetyl-CoA ligases," and "acyl-activating enzymes."

"Functional deletion" or its grammatical equivalents refers to any modification to a microorganism that ablates, reduces, inhibits, or otherwise disrupts production of a gene product, renders the gene product non-functional, or otherwise reduces or ablates the gene product's activity. "Gene product" refers to a protein or polypeptide encoded and produced by a particular gene. "Gene" as used herein refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others. In some versions of the invention, "functionally deleted acsA gene product or homolog thereof" means that the acsA gene is mutated to an extent that an acsA gene product or homolog thereof is not produced at all.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations, partial or complete deletions, insertions, or other variations to a coding sequence or a sequence controlling the transcription or translation of a coding sequence; placing a coding sequence under the control of a less active promoter; blocking transcription of the gene with a trans-acting DNA binding protein such as a TAL effector or CRISPR guided Cas9; and expressing ribozymes or antisense sequences that target the mRNA of the gene of interest, etc. In some versions, a gene or coding sequence can be replaced with a selection marker or screenable marker. Various methods for introducing the genetic modifications described above are well known in the art and include homologous recombination, among other mechanisms. See, e.g., Green et al., *Molecular Cloning: A laboratory manual*, 4th ed., Cold Spring Harbor Laboratory Press (2012) and Sambrook et al., *Molecular Cloning: A Laboratory Manual*, 3rd ed., Cold Spring Harbor Laboratory Press (2001). Various other genetic modifications that functionally delete a gene product are described in the examples below. Functional deletion can also be accomplished by inhibiting the activity of the gene product, for example, by chemically inhibiting a gene product with a small molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding microorganism. In certain versions, the genetic modifications giving rise to a functionally deleted gene product are determined with respect to the gene or coding sequence in its unaltered state as found in nature. In certain versions, the genetic modifications giving rise to a functionally deleted gene product are determined with respect to the gene or coding sequence in its form in a corresponding microorganism.

Some versions of the invention include a plurality of microorganisms, wherein greater than about 1%, about 5%, about 10%, about 15%, about 20%, about 25%, about 30%, about 35%, about 40%, about 50%, about 55%, about 60%, about 65%, about 70%, about 75%, about 80%, about 85%, about 90%, about 95%, or more of the plurality of microorganisms comprise a functionally deleted acsA gene product or homolog thereof. In some versions, the plurality of microorganisms is a microbial culture.

Genetic modifications that can be introduced into the acsA gene or homologs thereof to functionally delete the acsA gene product or homologs thereof, such as generating acsA knockouts, are described in the examples below.

The acsA gene is an acetyl-CoA synthetase gene in the exemplary cyanobacterium *Synechococcus* sp. PCC 7002, the coding sequence of which can be found in GenBank under accession number NC_010475.1 and is as follows:

```
                                          (SEQ ID NO: 1)
atgtccgaac aaaacattga atccatcctc caggagcagc gccttttttc gcctgcacca gactttgctg ccgaggccca gatcaagagc ttagaccagt accaagccct ctacgaccgg gcgaaaaatg accccgaagg cttttggggg gaactcgccg aacaggaatt ggaatggttt gagaaatggg acaaggtgct cgattggcaa ccgcccttcg ccaaatggtt tgtcaacggg aaaattaaca tttcctacaa ttgcctcgac cgtcatctca aaacctggcg caaaaataaa gccgccctca tctgggaagg ggaacccggt gactcccgta ccctcaccta tgcccagcta caccacgagg tctgccagtt tgccaatgcg atgaaaaagt tgggcgtcaa aaaaggcgat cgcgtcggga tttatatgcc aatgatcccg gaagccgtcg ttgccctcct cgcctgtgcc cgcattggtg cgccccatac ggtgatattt ggtggcttta gtgccgaagc cctccgcagt cgcctcgaag acgctgaagc caaactggtg atcaccgccg acggggggctt ccgcaaagat aaagcggtac ccctcaagga tcaagtagat gcggcgatcg ccgatcacca tgcccccagc gttgagaatg ttttggtcgt tcaacgcacc aaagagcctg tccacatgga agccgggcgg gatcactggt ggcatgattt gcaaaaagaa gtctccgctg actgtcccgc cgagccgatg gatgccgaag atatgctctt catcctctat accagcggca ccacgggtaa acccaagggc gttgtccaca ctacgggcgg ttataatctc tacacccata taacgaccaa gtggatcttt gatctcaaag atgatgacgt gtattggtgt ggtgctgatg tgggttggat caccggccac agttacatta cctatggccc tctatctaac ggggcaacgg tcttaatgta tgaaggcgca cccgtccgt ctaatccgg ttgctattgg gaaattattc aaaaatatgg tgtcaccatt ttctatacgg cacccacagc gattcgggcc tttatcaaaa tgggtgaagg catccccaat aaatatgaca tgagttccct gcgcctctta ggaaccgtgg gtgaaccgat taacccagaa gcttggatgt ggtaccaccg ggtcattggt ggcgaacgtt gtcccattgt tgatacatgg tggcaaacgg aaaccggtgg tgtgatgatt acgcctttac ccggtgcaac tcccacaaaa cccggctcgg caactcgtcc ttttccgggg attgtggcgg atgtcgttga ccttgatgga aattccgttg gtgacaacga aggcggctac ctggtagtga aacaaccctg gcctgggatg atgcgtactg tttacggcaa tcccgaacgc ttccggtcta cctattggga gcacatcgcc ccgaaagatg gacaatacct ttatttcgca ggtgacgggg cacgccgtga ccaagatggc tattttgga ttatgggtcg cgtcgatgat gtcttaaatg tttcgggcca tcgcctcggc accatggaag tggaatcggc cctcgttttcc cacccctgccg tcgccgaagc agccgtggtt ggaaagccag atccggttaa gggggaagag gtgttttgcct ttgtcaccct tgagggcacc tacagtccga gcgacgatct cgtaacggaa ctcaaggccc atgtggtgaa agaaattggg gcgatcgccc gtccgggaga aatccgtttt gccgatgtaa
```

```
tgcccaaaac  ccgttctggg  aagatcatgc  ggcgtttgtt gcgaaaccta  gccgcaggtc  aggaaattgt  gggcgacacc tccaccctcg  aagaccgcag  cgtcctcgat  caactccggg gctaa
```

The acsA coding sequence in the exemplary organism *Synechococcus* sp. PCC 7002 encodes a protein included in GenBank under accession number YP_001735082.1, having the following amino acid sequence:

```
                                             (SEQ ID NO: 2)
MSEQNIESIL  QEQRLFSPAP  DFAAEAQIKS  LDQYQALYDR

AKNDPEGFWG  ELAEQELEWF  EKWDKVLDWQ  PPFAKWFVNG

KINISYNCLD  RHLKTWRKNK  AALIWEGEPG  DSRTLTYAQL

HHEVCQFANA  MKKLGVKKGD  RVGIYMPMIP  EAVVALLACA

RIGAPHTVIF  GGFSAEALRS  RLEDAEAKLV  ITADGGFRKD

KAVPLKDQVD  AAIADHHAPS  VENVLVVQRT  KEPVHMEAGR

DHWWHDLQKE  VSADCPAEPM  DAEDMLFILY  TSGTTGKPKG

VVHTTGGYNL  YTHITTKWIF  DLKDDDVYWC  GADVGWITGH

SYITYGPLSN  GATVLMYEGA  PRPSNPGCYW  EIIQKYGVTI

FYTAPTAIRA  FIKMGEGIPN  KYDMSSLRLL  GTVGEPINPE

AWMWYHRVIG  GERCPIVDTW  WQTETGGVMI  TPLPGATPTK

PGSATRPFPG  IVADVVDLDG  NSVGDNEGGY  LVVKQPWPGM

MRTVYGNPER  FRSTYWEHIA  PKDGQYLYFA  GDGARRDQDG

YFWIMGRVDD  VLNVSGHRLG  TMEVESALVS  HPAVAEAAVV

GKPDPVKGEE  VFAFVTLEGT  YSPSDDLVTE  LKAHVVKEIG

AIARPGEIRF  ADVMPKTRSG  KIMRRLLRNL  AAGQEIVGDT

STLEDRSVLD  QLRG
```

Homologs of acsA include coding sequences, genes, or gene products that are homologous to the acsA coding sequence, acsA gene, or the acsA gene product, respectively. Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the coding sequences, genes, or gene products described herein include coding sequences, genes, or gene products, respectively, having at least about 30%, 35%, 40%, 45%, 50%, 55%, 60%, 65%, 70%, 75%, 80%, 85%, 90%, 95%, or 99% identity to the coding sequences, genes, or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes or coding sequences thereof in different species that evolved from a common ancestral gene by speciation. Normally, orthologs retain the same or similar function in the course of evolution. As used herein "orthologs" are included in the term "homologs".

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to acsA or other coding sequences, genes, or gene products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., *J. Mol. Biol.* 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous" without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Homologs of the acsA gene product include enzymes falling under Enzyme Commission (EC) number 6.2.1.1. Non-limiting examples of homologs of the acsA gene product in various microorganisms include the acetyl-coenzyme A synthetase from *Fischerella* sp. JSC-11 represented by GenBank Accession No. ZP_08986431.1, the acetyl-coenzyme A from *Moorea producta* 3 L synthetase represented by GenBank Accession No. ZP_08425677.1, the acetate/CoA from *Cyanothece* sp. PCC 7822 ligase represented by GenBank Accession No. YP_003886065.1, the acetyl-CoA from *Cyanothece* sp. PCC 7424 synthetase represented by GenBank Accession No. YP_002378472.1, the unnamed protein product from *Thermosynechococcus elongatus* BP-1 represented by GenBank Accession No. NP_681677.1, the unnamed protein product from *Anabaena variabilis* ATCC 29413 represented by GenBank Accession No. YP_321725.1, the acetate-CoA ligase from *Cylindrospermopsis raciborskii* CS-505 represented by GenBank Accession No. ZP_06308209.1, the acetyl-CoA synthetase from *Nostoc punctiforme* PCC 73102 represented by GenBank Accession No. YP_001869493.1, the acetate-CoA ligase from *Microcoleus chthonoplastes* PCC 7420 represented by GenBank Accession No. ZP_05030125.1, the acetyl-coenzyme A synthetase from *Nodularia spumigena* CCY9414 represented by GenBank Accession No. ZP_01629204.1, the acetyl-CoA synthetase from *Microcystis aeruginosa* NIES-843 represented by GenBank Accession No. YP_001660936.1, the acetate/CoA ligase from '*Nostoc azollae*' 0708 represented by GenBank Accession No. YP_003723268.1, the acsA gene product from *Microcystis aeruginosa* PCC 7806 represented by GenBank Accession No. CAO86486.1, the acetyl-coenzyme A synthetase from *Microcoleus vaginatus* FGP-2 represented by GenBank Accession No. ZP_08490634.1, the Acetate-CoA ligase from *Raphidiopsis brookii* D9 represented by GenBank Accession No. ZP_06304063.1, the acsA gene product from *Acaryochloris marina* MBIC11017 represented by GenBank Accession No. YP_001517064.1, the acetyl-CoA synthetase from *Acaryochloris* sp. CCMEE 5410 represented by GenBank Accession No. ZP_09248274.1, the acetyl-CoA synthetase from *Oscillatoria* sp. PCC 6506 represented by GenBank Accession No. ZP_07113076.1, the acetyl-CoA synthetase from *Cyanothece* sp. PCC 7425 represented by GenBank Accession No. YP_002484565.1, the Acetate-CoA ligase from *Lyngbya* sp. PCC 8106 represented by GenBank Accession No. ZP_01623739.1, the unnamed protein product from *Trichodesmium erythraeum* IMS101 represented by GenBank Accession No. YP_722064.1, the acetyl-CoA synthetase from *Arthrospira platensis* str. *Paraca* represented by GenBank Accession No. ZP_06383883.1, the acetate/CoA ligase from *Arthrospira maxima* CS-328 represented by GenBank Accession No. ZP_03274675.1, the acetyl-coenzyme A synthetase from *Arthrospira* sp. PCC 8005 represented by GenBank Accession No. ZP_09782650.1, the acetate/CoA ligase from *Arthrospira maxima* CS-328 represented by GenBank Accession No. EDZ93724.1, the acetyl-coenzyme A synthetase from *Arthrospira* sp. PCC 8005 represented by GenBank Accession No. CCE18403.1, the unnamed protein product from *Cyanothece* sp. PCC 8802 represented by GenBank Accession No. YP_003138301.1, the acetate/CoA ligase from *Cyanothece* sp. PCC 8802 represented by GenBank Accession No. ACV01466.1, the acetyl-CoA synthetase from *Cyanothece* sp. PCC 8801 represented by GenBank Accession No. YP_002373634.1, the acetyl-coenzyme A synthetase from *Cyanothece* sp. ATCC 51472 represented by GenBank Accession No. ZP_08974038.1, the unnamed protein product from *Synechococcus elongatus* PCC 6301 represented by GenBank Accession No. ZP_08974038.1, the acetyl-CoA synthetase from *Cyanothece* sp. ATCC 51142 represented by GenBank Accession No. YP_001803432.1, the acetyl-coenzyme A synthetase from *Cyanothece* sp. CCY0110 represented by GenBank Accession No. ZP_01730332.1, the AMP-dependent synthetase and ligase from *Crocosphaera watsonii* WH 8501 represented by GenBank Accession No. ZP_00514814.1, the acetate-CoA ligase from *Synechococcus* sp. PCC 7335 represented by GenBank Accession No. ZP_05036109.1, the acetyl-coenzyme A synthetase from *Synechococcus* sp. WH 8102 represented by GenBank Accession No. NP_897106.1, the acetate-CoA ligase from *Synechococcus* sp. WH 7805 represented by GenBank Accession No. ZP_01123920.1, the acetate-CoA ligase from *Synechococcus* sp. WH 8109 represented by GenBank Accession No. ZP_05788236.1, the acetyl-coenzyme A synthetase from *Prochlorococcus marinus* str. MIT 9313 represented by GenBank Accession No. NP_894222.1, the acetyl-coenzyme A synthetase from *Prochlorococcus marinus* str. MIT 9303 represented by Gen- Bank Accession No. YP_001017906.1, the acetyl-CoA synthetase from *Synechococcus* sp. WH 7803 represented by GenBank Accession No. YP_001224763.1, the acetyl-coenzyme A synthetase from *Synechococcus* sp. RS9917 represented by GenBank Accession No. ZP_01080065.1, the acetyl-coenzyme A synthetase from *Synechococcus* sp. WH 8016 represented by GenBank Accession No. ZP_08955323.1, the acetate-CoA ligase from *Synechococcus* sp. CC9311 represented by GenBank Accession No. YP_730758.1, the acetyl-coenzyme A synthetase from *Prochlorococcus marinus* str. MIT 9211 represented by GenBank Accession No. YP_001550915.1, the acetate-CoA ligase from *Synechococcus* sp. CC9902 represented by GenBank Accession No. YP_377326.1, the acetate-CoA ligase from *Synechococcus* sp. BL107 represented by GenBank Accession No. ZP_01467683.1, the acetyl-coenzyme A synthetase from *Synechococcus* sp. RS9916 represented by GenBank Accession No. ZP_01471857.1, the acetyl-coenzyme A synthetase from *Synechococcus* sp. CC9605 represented by GenBank Accession No. YP_381449.1, the acetyl-coenzyme A synthetase from *Synechococcus* sp. CB0205 represented by GenBank Accession No. ZP_07971118.1, the acetyl-CoA synthetase from *Synechococcus* sp. RCC307 represented by GenBank Accession No. YP_001227601.1, the acetyl-coenzyme A synthetase from *Synechococcus* sp. CB0101 represented by GenBank Accession No. ZP_07973216.1, the acetate-CoA ligase from *Cyanobium* sp. PCC 7001 represented by GenBank Accession No. ZP_05043915.1, the acetate-CoA ligase from *Synechococcus* sp. WH 5701 represented by GenBank Accession No. ZP_01085120.1, the acs gene product from *Prochlorococcus marinus* subsp. *marinus* str. CCMP1375 represented by GenBank Accession No. NP_875433.1, the acetyl-coenzyme A synthetase from *Prochlorococcus marinus* str. NATL2A represented by GenBank Accession No. YP_291252.1, the acetyl-coenzyme A synthetase from *Gloeobacter violaceus* PCC 7421 represented by GenBank Accession No. NP_923105.1, the acetyl-coenzyme A synthetase from *cyanobacterium* UCYN-A represented by GenBank Accession No. YP_003421821.1, the acetyl-coenzyme A synthetase from *Prochlorococcus marinus* str. NATL1A represented by GenBank Accession No. YP_001014503.1, the acetyl-coenzyme A synthetase from *Singulisphaera acidiphila* DSM 18658 represented by GenBank Accession No. ZP_09573232.1, the acetyl-coenzyme A synthetase from *Prochlorococcus marinus* subsp. *pastoris* str. CCMP1986 represented by GenBank Accession No. NP_892737.1, the acetyl-coenzyme A synthetase from *Prochlorococcus marinus* str. MIT 9312 represented by GenBank Accession No. YP_397116.1, the acetate/CoA ligase from *Meiothermus ruber* DSM 1279 represented by GenBank Accession No. YP_003507084.1, the acetyl-coenzyme A synthetase from *Prochlorococcus marinus* str. MIT 9215 represented by GenBank Accession No. YP_001483902.1, the acs gene product from *Prochlorococcus marinus* str. AS9601 represented by GenBank Accession No. YP_001009068.1, the acetyl-coenzyme A synthetase from *Prochlorococcus marinus* str. MIT 9515 represented by GenBank Accession No. YP_001011000.1, the acetate-CoA ligase from *Prochlorococcus marinus* str. MIT 9202 represented by GenBank Accession No. ZP_05137406.1, the acetyl-coenzyme A synthetase from *Marinithermus hydrothermalis* DSM 14884 represented by GenBank Accession No. YP_004368660.1, the acetyl-coenzyme A synthetase from *Prochlorococcus marinus* str. MIT 9301 represented by GenBank Accession No. YP_001090869.1, the unnamed protein product from *Nostoc* sp. PCC 7120 represented by GenBank Accession No. NP_488297.1, the acetate/CoA ligase from *Truepera radiovictrix* DSM 17093 represented by GenBank Accession No. YP_003703935.1, the acetate/CoA ligase from *Haliangium ochraceum* DSM 14365 represented by GenBank Accession No. YP_003269915.1, the acetyl-coenzyme A synthetase from *Gemmata obscuriglobus* UQM 2246 represented by GenBank Accession No. ZP_02733777.1, the acetyl-coenzyme A synthetase from *Isosphaera pallida* ATCC 43644 represented by GenBank Accession No. YP_004179760.1, the acetyl-CoA synthetase from *Chloroherpeton thalassium* ATCC 35110 represented by GenBank Accession No. YP_001995147.1, the acetate-CoA ligase from *Planctomyces maris* DSM 8797 represented by GenBank Accession No. ZP_01856978.1, the acetyl-CoA synthetase from *Thermus thermophilus* HB8 represented by GenBank Accession No. YP_144514.1, the acetate/CoA ligase from *Planctomyces limnophilus* DSM 3776 represented by GenBank Accession No. YP_003632128.1, the acetyl-CoA synthetase from *Thermus thermophilus* HB27 represented by GenBank Accession No. YP_004855.1, the acetyl-coenzyme a synthetase from *Oceanithermus profundus* DSM 14977 represented by GenBank Accession No. YP_004057553.1, the acetyl-coenzyme A synthetase from *Candidatus Koribacter versatilis* Ellin345 represented by GenBank Accession No. YP_592595.1, the acetate/CoA ligase from *Meiothermus silvanus* DSM 9946 represented by GenBank Accession No. YP_003684983.1, the acetate-CoA ligase from *Verrucomicrobium spinosum* DSM 4136 represented by GenBank Accession No. ZP_02931268.1, the acetate/CoA ligase from *Thermus aquaticus* Y51MC23 represented by GenBank Accession No. ZP_03496427.1, the acetyl-coenzyme A synthetase from *Symbiobacterium thermophilum* IAM 14863 represented by GenBank Accession No. YP_074710.1, the acetate/CoA ligase from *bacterium* Ellin 514 represented by GenBank Accession No. ZP_03630513.1, the acetyl-CoA synthetase from uncultured candidate division OP1 bacterium represented by GenBank Accession No. BAL56248.1, the acetyl-coenzyme A synthetase from *Blastopirellula marina* DSM 3645 represented by GenBank Accession No. ZP_01092728.1, the acs2 gene product from *Thermus scotoductus* SA-01 represented by GenBank Accession No. YP_004201921.1, the acetyl-coenzyme A synthetase from *Archaeoglobus veneficus* SNP6 represented by GenBank Accession No. YP_004341076.1, the Acetyl-coenzyme A synthetase from *Desulfitobacterium dehalogenans* ATCC 51507 represented by GenBank Accession No. ZP_09634500.1, the unnamed protein product from *Candidatus Chloracidobacterium thermophilum* B represented by GenBank Accession No. YP_004864177.1, the acetate-CoA ligase from *Acidobacterium capsulatum* ATCC 51196 represented by GenBank Accession No. YP_002755829.1, the acetate/CoA ligase from *Pirellula staleyi* DSM 6068 represented by GenBank Accession No. YP_003369860.1, the acetyl-CoA synthetase from *Chlorobium chlorochromatii* CaD3 represented by GenBank Accession No. YP_379980.1, the acetate-CoA ligase from *Myxococcus xanthus* DK 1622 represented by GenBank Accession No. YP_630789.1, the acetate-CoA ligase from *Myxococcus fulvus* HW-1 represented by GenBank Accession No. YP_004667083.1, the unnamed protein product from *Candidatus Solibacter usitatus* Ellin 6076 represented by GenBank Accession No. YP_829106.1, the acetyl-coenzyme A synthetase from *Planctomyces brasiliensis* DSM 5305 represented by GenBank Accession No. YP_004268501.1, the acetyl-CoA synthetase from *Escherichia coli* UMN026 represented by GenBank Accession No. YP_002415210.1, the acetyl-CoA synthetase from *Escherichia coli* FVEC1412 represented by GenBank Accession No. ZP_06646805.1, the acetyl-coenzyme A synthetase from *Escherichia coli* FVEC1302 represented by GenBank Accession No. ZP_06988121.1, the acetate-CoA ligase from *Escherichia coli* MS198-1 represented by GenBank Accession No. ZP_07115900.1, the acetyl-CoA synthetase from *Escherichia coli* UMN026 represented by GenBank Accession No. CAR15720.1, the Acs2p from *Saccharomyces cerevisiae* S288c represented by GenBank Accession No. NP_013254.1, the acetyl CoA synthetase from *Saccharomyces cerevisiae* YJM789 represented by GenBank Accession No. EDN59693.1, the K7_Acs2p from *Saccharomyces cerevisiae* Kyokai no. 7 represented by GenBank Accession No. GAA25035.1, the acetyl CoA synthetase from *Saccharomyces cerevisiae* RM11-1a represented by GenBank Accession No. EDV09449.1, the bifunctional acetyl-CoA synthetase and propionyl-CoA synthetase from *Escherichia coli* str. K12 substr. W3110 represented by GenBank Accession No. BAE78071.1, and the acetyl-coenzyme A synthetase from *Pseudomonas fulva* 12-X represented by GenBank Accession No. YP_004473024.1, among others. The coding sequences encoding these gene products can be found in GenBank (http://www.ncbi.nlm.nih.gov/GenBank/).

Homologs of acsA and AcsA discussed in the examples include the acetyl-CoA synthetase from *Synechocystis* sp. PCC 6803 (sll0542; GenBank Accession No. NP_442428.1; SEQ ID NOS:3 and 4) and the unnamed protein product from *Synechococcus* sp. PCC 7942 (SYNPCC7942_1342; GenBank Accession No. YP_400369.1; SEQ ID NOS:5 and 6).

The microorganism of the present invention preferably includes any microorganism that harbors an acsA gene or homolog thereof or expresses an acsA gene product or homolog thereof that is capable of being functionally deleted to render the microorganism more tolerant of organic acids. The microorganism may be eukaryotic, such as yeast, or prokaryotic, such as bacteria or archaea. Among bacteria, gram-positive, gram-negative, and ungrouped bacteria are suitable. Phototrophs, lithotrophs, and organotrophs are also suitable. In preferred versions of the invention, the microorganism is a phototroph, such as a cyanobacterium. Suitable cyanobacteria include those from the genuses *Agmenellum, Anabaena, Aphanocapsa, Arthrosprira, Gloeocapsa, Haplosiphon, Mastigocladus, Nostoc, Oscillatoria, Prochlorococcus, Scytonema, Synechococcus,* and *Synechocystis*. Preferred cyanobacteria include those selected from the group consisting of *Synechococcus* spp., spp., *Synechocystis* spp., and *Nostoc* spp. Particularly suitable examples of *Synechococcus* spp. include *Synechococcus* sp. PCC 7942 and *Synechococcus* sp. PCC 7002. A particularly suitable example of *Synechocystis* spp. includes *Synechocystis* sp. PCC 6803. A benefit of phototrophs is that they require only $CO_2$ as a carbon source and are not dependent on food-based commodities or other types of biomass for which there is a growing high demand.

Functional deletion of the acsA gene product or homolog thereof in the microorganism results in increased tolerance of the microorganism to organic acids compared to a corresponding microorganism. As used herein, "corresponding microorganism" refers to a microorganism of the same species having the same or substantially same genetic and proteomic composition as a microorganism of the invention, with the exception of genetic and proteomic differences resulting from the modifications described herein for the microorganisms of the invention. Such tolerance is with respect to any organic acid present within the organism or its growth medium, particularly those that may be present in high abundance. Non-limiting examples of organic acids to which the microorganisms of the present invention have increased tolerance include acetic acid, acrylic acid, aspartic acid, benzoic acid, butyric acid, citric acid, formic acid, fumaric acid, furan dicarboxylic acid (2,5-furandicarboxylic acid), glucaric acid, glutamic acid, heptanoic acid, hexanoic acid, 3-hydroxypropionic acid (3HP), isophthalic acid, itaconic acid, lactic acid, levoascorbic acid, levulinic acid, malic acid, octanoic acid, oxalic acid, pentanoic acid, phosphoric acid, propionic acid, pyruvic acid, succinic acid (1,4 succinic acid), and terephthalic acid, among others. The examples show various aspects of increased tolerance to exemplary organic acids 3-hydroxypropionic acid (3HP), acrylic acid, and propionic acid.

One aspect of the increased tolerance to organic acids is an increase in the minimal inhibitory concentration (MIC) of a particular organic acid compared to a corresponding microorganism. MIC is the lowest concentration of an agent that will inhibit growth of a microorganism. An MIC can be determined by titrating the agent in the growth medium of the microorganism. The lowest concentration of the agent in which the microorganism is no longer able to grow is the MIC. Methods of culturing microorganisms and of detecting their growth are well known in the art and are not discussed in detail herein. A relative increase in MIC indicates a higher tolerance to an agent and indicates that the microorganism can grow in the presence of a higher concentration of the agent. Conversely, a relative decrease in MIC indicates a lower tolerance to an agent and indicates that the microorganism can grow only in the presence of a lower concentration of the agent.

Functional deletion of the acsA gene product or homolog thereof in the microorganism confers an MIC of at least about 10 µM, 25 µM, 50 µM, 75 µM, 100 µM, 250 µM, 500 µM, 1 mM, 25 mM, 50 mM, 70 mM, 100 mM, 125 mM, or 150 mM to acrylic acid; an MIC of at least about 10 mM, 15 mM, 20 mM, 25 mM, 50 mM, 75 mM, 100 mM, 125 mM, 150 mM, 175 mM, 200 mM, 225 mM, 250 mM, 260 mM, 300 mM, 350 mM, or more to 3HP; and/or an MIC of at least about 250 µM, 500 µM, 1 mM, 50 mM, 100 mM, 200 mM, 300 mM, 350 mM, 400 mM, 450 mM, 500 mM, or more to propionic acid. Such MICs occur in at least *Synechococcus* sp. cyanobacteria, such as *Synechococcus* sp. PCC 7002 and *Synechococcus* sp. PCC 7942, when assayed at a pH of about 8. Such MICs also occur in *Synechocystis* sp., such as *Synechocystis* sp. PCC 6803, when assayed at a pH of about 8. Such MICs also occur in any other microorganism described herein, such as *Prochlorococcus* sp., *Nostoc* sp., or others.

Another aspect of increased tolerance is increased growth rate in the presence of a certain concentration of an organic acid or an equal growth rate in the presence of an increased concentration of an organic acid compared to a corresponding microorganism.

In various aspects of the invention, functional deletion of the acsA gene product or homolog thereof in the microorganism confers at least about a 1.5-fold, a 5-fold, a 10-fold, a 15-fold, a 25-fold, a 50-fold, a 75-fold, a 100-fold, a 500-fold, a 750-fold, a 1.000-fold, 1.250-fold, a 1.500-fold, a 1.750-fold, a 2.000-fold, a 2.250-fold, a 2.500-fold, a 2.750-fold, a 3.000-fold, a 3.250-fold, or a 3.500-fold increase in tolerance against an organic acid. The organic acid to which functional deletion of the acsA gene product confers such MICs may include acrylic acid, 3HP, propionic acid, or lactic acid, among others. In some versions of the invention, for example, functional deletion of the acsA gene product in *Synechococcus* sp. PCC 7002 confers at least about a 2.800-fold increase in MIC for acrylic acid, at least about a 26-fold increase in MIC for 3HP, and at least about a 100-fold increase in MIC for propionic acid at pH of about 8 (see examples below).

The increased tolerance to organic acids conferred by functional deletion of the acsA gene product or homolog thereof renders the microorganism particularly suited for producing high amounts of organic acids, many of which have industrial utility. Accordingly, the microorganism in some versions of the invention is capable of producing an organic acid that can be isolated for industrial purposes. The microorganism may be able to naturally make the organic acid, may be genetically modified to make the organic acid, or may be genetically modified to make increased amounts of the organic acid that it already makes. Non-limiting examples of organic acids that the microorganisms of the present invention can produce include acetic acid, aspartic acid, benzoic acid, citric acid, formic acid, fumaric acid, furan dicarboxylic acid (2,5-furandicarboxylic acid), glucaric acid, glutamic acid, 3-hydroxypropionic acid (3HP), isophthalic acid, itaconic acid, lactic acid, levoascorbic acid, levulinic acid, malic acid, oxalic acid, phosphoric acid, propionic acid, pyruvic acid, succinic acid (1,4 succinic acid), and terephthalic acid, among others. In preferred versions of the invention, the microorganism is capable of making at least 3HP and or lactic acid.

The microorganism may be modified to express or increase expression of one or more genes involved in the production of the organic acid. Modifying the microorganism to express or increase expression of a gene can be performed using any methods currently known in the art or discovered in the future. Examples include genetically modifying the microorganism and culturing the microorganism in the presence of factors that increase expression of the gene. Suitable methods for genetic modification include but are not limited to placing the coding sequence under the control of a more active promoter, increasing the copy number of the gene, and/or introducing a translational enhancer on the gene (see, e.g., Olins et al. *Journal of Biological Chemistry*, 1989, 264(29):16973-16976). Increasing the copy number of the gene can be performed by introducing additional copies of the gene to the microorganism, i.e., by incorporating one or more exogenous copies of the native gene or a heterologous homolog thereof into the microbial genome, by introducing such copies to the microorganism on a plasmid or other vector, or by other means. "Exogenous" used in reference to a genetic element means the genetic element is introduced to a microorganism by genetic modification. "Heterologous" used in reference to a genetic element means that the genetic element is derived from a different species. A promoter that controls a particular coding sequence is herein described as being "operationally connected" to the coding sequence.

The microorganisms of the invention may include at least one recombinant nucleic acid configured to express or overexpress a particular enzyme. "Recombinant" as used herein with reference to a nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially modified but contain the same regulatory sequences and coding regions that are found in the organism from which the nucleic acid was isolated. A recombinant cell or microorganism is one that contains a recombinant nucleic acid molecule or polypeptide. "Overexpress" as used herein means that a particular gene product is produced at a higher level in one cell, such as a recombinant cell, than in a corresponding cell. For example, a microorganism that includes a recombinant nucleic acid configured to overexpress an enzyme produces the enzyme at a greater amount than a microorganism that does not include the recombinant nucleic acid.

In some versions of the invention, the microorganism is genetically modified to produce or enhance production of 3HP. Such a microorganism can be obtained by expressing or increasing expression of a gene for any one or more of the enzymes catalyzing the various steps in a 3HP-production pathway. Non-limiting examples of suitable enzymes include pyruvate kinase, pyruvate dehydrogenase, acetyl-CoA carboxylase, malonyl-CoA reductase, malonate semialdehyde reductase, phosphoenolpyruvate carboxylase, aspartate aminotransferase, aspartate decarboxylase, and β-alanine/α-ketoglutarate aminotransferase. See FIGS. 7, 9A, and 9B. See also U.S. Pat. No. 8,048,624 to Lynch, U.S. Pub. 2011/0125118 to Lynch, U.S. Pub. 2010/0210017 to Gill et al., and Warnecke et al. *Metabolic Engineering* (2010) 12:241-250 for additional enzymes.

Accordingly, some microorganisms of the invention include at least one recombinant nucleic acid configured to express or overexpress a malonyl-CoA reductase. Malonyl-CoA reductases include the enzymes classified under EC 1.2.1.75. In some versions, the microorganism is modified to harbor a nucleic acid encoding the malonyl-CoA reductase from *Chloroflexus aurantiacus* or a homolog thereof. The coding sequence for the malonyl-CoA reductase from *Chloroflexus aurantiacus* is included in GenBank under accession number AY530019 and is represented by SEQ ID NO:7. The *Chloroflexus aurantiacus* malonyl-CoA reductase gene product is included in GenBank under accession number AAS20429 and has an amino acid sequence represented by SEQ ID NO:8. The malonyl-CoA reductase from *Chloroflexus aurantiacus* has been shown to be a bi-functional enzyme, having activity that converts malonyl-CoA to malonate semialdehyde in addition to activity that converts malonate semialdehyde to 3HP.

Exemplary homologs of the *Chloroflexus aurantiacus* malonyl-CoA reductase gene product include but are not limited to the short-chain dehydrogenase/reductase SDR from *Chloroflexus aggregans* DSM 9485 represented by GenBank Accession No. YP_002462600.1, the short-chain dehydrogenase/reductase SDR from *Oscillochloris trichoides* DG6 represented by GenBank Accession No. ZP_07684596.1, the short-chain dehydrogenase/reductase SDR from *Roseiflexus castenholzii* DSM 13941 represented by GenBank Accession No. YP_001433009.1, the short-chain dehydrogenase/reductase SDR from *Roseiflexus* sp. RS-1 represented by GenBank Accession No. YP_001277512.1, among others. The coding sequences encoding these gene products can be found in GenBank.

Homologs of the *Chloroflexus aurantiacus* malonyl-CoA reductase also include enzymes having an amino acid sequence at least about 80%, 85%, 90%, 95%, 97%, 98%, 99% or more identical to SEQ ID NO:8. Sequences having these percent identities can be obtained by aligning SEQ ID NO:8 to the sequences of the *Chloroflexus aurantiacus* malonyl-CoA reductase homologs listed above or otherwise known in the art to determine which residues are amenable to variation (i.e., substitution, deletion, addition, etc.) and the identities of the suitably substituted or added residues.

In some versions of the invention, the microorganism is modified to harbor a nucleic acid encoding the malonyl-CoA reductase from *Sulfolobus tokodaii* or a homolog thereof. The coding sequence for the malonyl-CoA reductase from *Sulfolobus tokodaii* is included in GenBank under accession number NC_003106.2 (positions 2170729-2171808; Gene ID 1460244) and is represented by SEQ ID NO:11. A truncated, codon-optimized version of the coding sequence preferred for expression in cyanobacteria is represented by SEQ ID NO:12. The gene product of the malonyl-CoA reductase from *Sulfolobus tokodaii* is included in GenBank under accession number NP_378167. A truncated gene product encoded by SEQ ID NO:12 and suitable for use in the present invention has an amino acid sequence represented by SEQ ID NO:13. The malonyl-CoA reductase from *Sulfolobus tokodaii* has been shown to have activity that converts malonyl-CoA to malonate semialdehyde. It does not appear to have activity that converts malonate semialdehyde to 3HP.

Exemplary homologs of the malonyl-CoA reductase from *Sulfolobus tokodaii* include but are not limited to the aspartate-semialdehyde dehydrogenase from *Acidianus hospitalis* W1 represented by GenBank Accession No. YP_004459517.1, the aspartate-semialdehyde dehydrogenase from *Metallosphaera sedula* DSM 5348 represented by GenBank Accession No. YP_001190808.1, the malonyl-/succinyl-CoA reductase from *Metallosphaera cuprina* Ar-4 represented by GenBank Accession No. YP_004410014.1, the aspartate-semialdehyde dehydrogenase from *Sulfolobales archaeon* AZ1 represented by GenBank Accession No. EWG07552.1, the aspartate-semialdehyde dehydrogenase from *Sulfolobus solfataricus* P2 represented by GenBank Accession No. NP_343563.1, the aspartate-semialdehyde dehydrogenase from *Metallosphaera yellowstonensis* represented by GenBank Accession No. WP_009071519.1, the aspartate-semialdehyde dehydrogenase from *Sulfolobus islandicus* M.16.27 represented by GenBank Accession No. YP_002844727.1, the aspartate-semialdehyde dehydrogenase from *Sulfolobus islandicus* L.S.2.15 represented by GenBank Accession No. YP_002833533.1, the aspartate-semialdehyde dehydrogenase from *Sulfolobus islandicus* HVE10/4 represented by GenBank Accession No. YP_005647305.1, the aspartate-semialdehyde dehydrogenase from *Sulfolobus islandicus* Y.N.15.51 represented by GenBank Accession No. YP_002841967.1, the aspartate-semialdehyde dehydrogenase from *Sulfolobus acidocaldarius* DSM 639 represented by GenBank Accession No. YP_256941.1, the aspartate-semialdehyde dehydrogenase from *Sulfolobus islandicus* M.14.25 represented by GenBank Accession No. YP_002830795.1, the aspartate-semialdehyde dehydrogenase from *Sulfolobus acidocaldarius* SUSAZ represented by GenBank Accession No. YP_008948306.1, the aspartate-semialdehyde dehydrogenase from *Sulfolobales archaeon* Acd1 represented by GenBank Accession No. WP_020198954.1, the aspartate-semialdehyde dehydrogenase from *Sulfolobus acidocaldarius* DSM 639 represented by GenBank Accession No. YP_256733.1, the aspartate-semialdehyde dehydrogenase from *Sulfolobus acidocaldarius* SUSAZ represented by GenBank Accession No. YP_008948046.1, the aspartate-semialdehyde dehydrogenase from *Archaeoglobus profundus* DSM 5631 represented by GenBank Accession No. YP_003401535.1, the aspartate-semialdehyde dehydrogenase from *Candidatus Caldiarchaeum subterraneum* represented by GenBank Accession No. YP_008797381.1, the aspartate-semialdehyde dehydrogenase from *Ferroglobus placidus* DSM 10642 represented by GenBank Accession No. YP_003435562.1, the aspartate-semialdehyde dehydrogenase from *Methanothermobacter marburgensis* str. Marburg represented by GenBank Accession No. YP_003850098.1, the aspartate-semialdehyde dehydrogenase from *Methanothermobacter thermautotrophicus* CaT2 represented by GenBank Accession No. BAM69964.1, the aspartate-semialdehyde dehydrogenase from *Methanothermobacter thermautotrophicus* str. Delta H represented by GenBank Accession No. NP_275938.1, the aspartate semialdehyde dehydrogenase from *Archaeoglobus sulfaticallidus* PM70-1 represented by GenBank Accession No. YP_007906903.1, the aspartate-semialdehyde dehydrogenase from *Pyrobaculum arsenaticum* DSM 13514 represented by GenBank Accession No. YP_001153189.1, the aspartate semialdehyde dehydrogenase from *Methanothermus fervidus* DSM 2088 represented by GenBank Accession No. YP_004004235.1, and the aspartate-semialdehyde dehydrogenase from *Methanopyrus kandleri* AV19 represented by GenBank Accession No. NP_614672.1, among others. The coding sequences encoding these gene products can be found in GenBank.

Homologs of the *Sulfolobus tokodaii* malonyl-CoA reductase also include enzymes having an amino acid sequence at least about 80%, 85%, 90%, 95%, 97%, 98%, 99% or more identical to SEQ ID NO:13. Sequences having these percent identities can be obtained by aligning SEQ ID NO:13 to the sequences of the *Sulfolobus tokodaii* malonyl-CoA reductase homologs listed above or otherwise known in the art to determine which residues are amenable to variation (i.e., substitution, deletion, addition, etc.) and the identities of the suitably substituted or added residues.

In some versions of the invention, the microorganism is modified to express or increase expression of a malonate semialdehyde reductase. Malonate semialdehyde reductase converts malonate semialdehyde to 3HP. Such a modification is preferred in microorganisms modified to express or increase expression of a malonyl-CoA reductase that does not convert malonate semialdehyde to 3HP, such as the malonyl-CoA reductase from *Sulfolobus tokodaii*. Suitable malonate semialdehyde reductases can use either NADH (EC 1.1.1.59) or NADPH (EC 1.1.1.298) as cofactors. Malonate semialdehyde reductases that use NADPH are preferred. In some versions, the microorganism is modified to harbor a nucleic acid encoding the malonate semialdehyde reductase from *Metallosphaera sedula* or a homolog thereof. The coding sequence of the malonate semialdehyde reductase from *Metallosphaera sedula* is included in GenBank under accession number NC_009440.1 (Gene ID 5103380; positions 1929295-1930239) and is represented by SEQ ID NO:14. A codon-optimized version of the coding sequence preferred for expression in cyanobacteria is represented by SEQ ID NO:15. The gene product of the malonate semialdehyde reductase from *Metallosphaera sedula* is included in GenBank under accession number YP_001192057 and has an amino acid sequence represented by SEQ ID NO:16.

Exemplary homologs of the malonate semialdehyde reductase from *Metallosphaera sedula* include but are not limited to the 3-hydroxyacyl-CoA dehydrogenase from *Metallosphaera sedula* DSM 5348 represented by GenBank Accession No. YP_001192057.1, the malonate semialdehyde reductase from *Metallosphaera cuprina* Ar-4 represented by GenBank Accession No. YP_004408885.1, the 3-hydroxyacyl-CoA dehydrogenase NAD-binding protein from *Acidianus hospitalis* W1 represented by GenBank Accession No. YP_004458285.1, the 3-hydroxyacyl-CoA dehydrogenase from *Sulfolobales archaeon* AZ1 represented by GenBank Accession No. EWG08084.1, the 3-hydroxyacyl-CoA dehydrogenase from *Metallosphaera yellowstonensis* represented by GenBank Accession No. WP_009075415.1, the 3-hydroxyacyl-CoA dehydrogenase from *Sulfolobus solfataricus* P2 represented by GenBank Accession No. NP_342162.1, the 3-hydroxyacyl-CoA dehydrogenase NAD-binding protein from *Sulfolobus islandicus* HVE10/4 represented by GenBank Accession No. YP_005646018.1, the 3-hydroxyacyl-CoA dehydrogenase NAD-binding protein from *Sulfolobus islandicus REY15A represented by GenBank Accession No. YP_005648646.1, the 3-hydroxyacyl-CoA dehydrogenase from Sulfolobus islandicus LAL14/1 represented by GenBank Accession No. YP_007865821.1, the 3-hydroxyacyl-CoA dehydrogenase from Sulfolobus islandicus M.14.25 represented by GenBank Accession No. YP_002829538.1, the 3-hydroxyacyl-CoA dehydrogenase from Sulfolobus islandicus represented by GenBank Accession No. WP_016732252.1, the 3-hydroxyacyl-CoA dehydrogenase from Sulfolobales archaeon Acd1 represented by GenBank Accession No. WP_020199213.1, the 3-hydroxybutyryl-CoA dehydrogenase from Sulfolobus tokodaii str. 7 represented by GenBank Accession No. NP_377470.1, the 3-hydroxyacyl-CoA dehydrogenase from Sulfolobus acidocaldarius SUSAZ represented by GenBank Accession No. YP_008947634.1, the 3-hydroxybutyryl-CoA dehydrogenase from Sulfolobus acidocaldarius DSM 639 represented by GenBank Accession No. YP_256228.1, the 3-hydroxyacyl-CoA dehydrogenase from Archaeoglobus fulgidus DSM 4304 represented by GenBank Accession No. NP_070034.1, the 3-hydroxyacyl-CoA dehydrogenase from Burkholderia sp. H160 represented by GenBank Accession No. WP_008917830.1, the 3-hydroxyacyl-CoA dehydrogenase represented by hbd-8 from Planctomyces maris represented by GenBank Accession No. WP_002645585.1, the 3-hydroxybutyryl-CoA dehydrogenase from Megasphaera sp. UPII 199-6 represented by GenBank Accession No. WP_007391670.1, the 3-hydroxyacyl-CoA dehydrogenase from Burkholderia pseudomallei 1026b represented by GenBank Accession No. YP_006275221.1, the 3-hydroxyacyl-CoA dehydrogenase from Burkholderia oklahomensis represented by GenBank Accession No. WP_010114811.1, and the 3-hydroxyacyl-CoA dehydrogenase from Burkholderia pseudomallei MSHR305 represented by GenBank Accession No. YP_008340862.1, among others. The coding sequences encoding these gene products can be found in GenBank.

Homologs of the Metallosphaera sedula malonate semialdehyde reductase also include enzymes having an amino acid sequence at least about 80%, 85%, 90%, 95%, 97%, 98%, 99% or more identical to SEQ ID NO:16. Sequences having these percent identities can be obtained by aligning SEQ ID NO:16 to the sequences of the Metallosphaera sedula malonate semialdehyde reductase homologs listed above or otherwise known in the art to determine which residues are amenable to variation (i.e., substitution, deletion, addition, etc.) and the identities of the suitably substituted or added residues.

In some versions of the invention, the microorganism is modified to express or increase expression of acetyl-CoA carboxylase, either alone, with a malonyl-CoA reductase, with a malonate semialdehyde reductase, or with other enzymes. Such a microorganism can be obtained by introducing exogenous nucleic acids expressing the acetyl-CoA carboxylase subunits into the microorganism, by introducing highly expressed promoters in front of the endogenous acetyl-CoA carboxylase subunit coding sequences, by increasing translational efficiency, or by other means. In bacteria, acetyl-CoA carboxylase is a multisubunit enzyme that is encoded by four genes, accA, accB, accC, and accD. Exemplary acetyl-coA carboxylase subunit genes for use in the present invention can be those found in Synechococcus sp. PCC 7002 or homologs thereof. The complete genome of Synechococcus sp. PCC 7002 can be found in GenBank under Accession No. NC_010475. The coding sequence for accA can be found at positions 2536162-2537139 of NC_010475, the gene product of which has a sequence represented by GenBank Accession No. YP_001735676.1. The coding sequence for accB can be found at positions 60707-61204 of NC_010475, the gene product of which has a sequence represented by GenBank Accession No. YP_001733325.1. The coding sequence for accC can be found at positions 2210473-2211819 of NC_010475, the gene product of which has a sequence represented by GenBank Accession No. YP_001735364.1". The coding sequence for accD can be found at positions 64484-65443 of NC_010475, the gene product of which has a sequence represented by GenBank Accession No. YP_001733331.1. Suitable promoters for increasing expression of these genes are known in the art. In some versions of the invention, an artificial operon comprising the accD, accA, accB, and accC coding sequences from E. coli can be introduced into the microorganism for expression or overexpression of acetyl-CoA carboxylase. See, e.g., US 2011/0165637 to Pfleger et al., which is incorporated herein by reference.

Figure 12A:
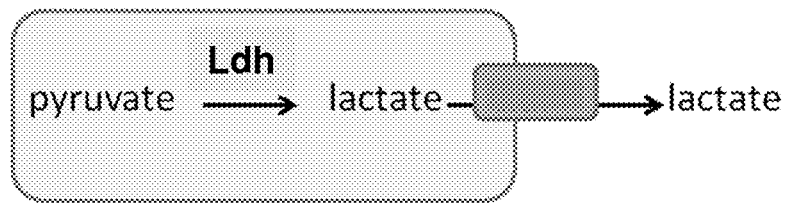
FIG. 12A depicts a schema for the production of lactate from pyruvate as catalyzed by lactate dehydrogenase (Ldh).

In some versions of the invention, the microorganism is genetically modified to produce or enhance production of lactate. Such a microorganism can be obtained by expressing or increasing expression of lactate dehydrogenase. Lactate dehydrogenase catalyzes the conversion of pyruvate to lactate. See FIG. 12A. Lactate dehydrogenases include the enzymes classified under EC 1.1.1.27 (L-lactate dehydrogenases) and 1.1.1.28 (D-lactate dehydrogenases). L-Lactate dehydrogenases are preferred.

In some versions of the invention, the microorganism is modified to harbor a nucleic acid encoding a lactate dehydrogenase from Bacillus subtilis or a homolog thereof. The coding sequence of the lactate dehydrogenase from Bacillus subtilis is included in GenBank under accession number AL009126.3 (positions 329774 to 330739) and is represented by SEQ ID NO:17. The gene product of the lactate dehydrogenase from Bacillus subtilis is included in GenBank under accession number NP_388187 and has an amino acid sequence represented by SEQ ID NO:18.

Exemplary homologs of the lactate dehydrogenase from Bacillus subtilis include but are not limited to the L-lactate dehydrogenase from Bacillus subtilis subsp. subtilis str. 168 represented by GenBank Accession No. NP_388187.2, the L-lactate dehydrogenase from Bacillus subtilis subsp. natto BEST195 represented by GenBank Accession No. YP_005559471.1, the L-lactate dehydrogenase from Bacillus subtilis BSn5 represented by GenBank Accession No. YP_004206262.1, the L-lactate dehydrogenase from Bacillus subtilis subsp. spizizenii TU-B-10 represented by GenBank Accession No. YP_004875853.1, the lactate dehydrogenase from Bacillus subtilis represented by GenBank Accession No. WP_017696103.1, the lactate dehydrogenase from Bacillus subtilis represented by GenBank Accession No. WP_003224788.1, the L-lactate dehydrogenase from Bacillus subtilis subsp. subtilis str. RO-NN-1 represented by GenBank Accession No. YP_005555343.1, the L-lactate dehydrogenase from Bacillus subtilis XF-1 represented by GenBank Accession No. YP_007425489.1, the L-lactate dehydrogenase from Bacillus subtilis represented by GenBank Accession No. WP_003241205.1, the lactate dehydrogenase from Bacillus subtilis represented by GenBank Accession No. WP_019257406.1, the lactate dehydrogenase from Bacillus mojavensis represented by GenBank Accession No. WP_010332943.1, the lactate dehydrogenase from Bacillus vallismortis represented by GenBank Accession No. WP_010331365.1, the L-lactate dehydrogenase from Bacillus subtilis subsp. spizizenii str. W23 represented by GenBank Accession No. YP_003864678.1, the L-lactate dehydrogenase from Bacillus atrophaeus represented by GenBank Accession No. WP_010787568.1, the lactate dehydrogenase from *Bacillus amyloliquefaciens* LFB112 represented by GenBank Accession No. YP_008948730.1, the L-lactate dehydrogenase from *Bacillus licheniformis* 9945A represented by GenBank Accession No. YP_008076533.1, the L-lactate dehydrogenase from *Halobacillus halophilus* DSM 2266 represented by GenBank Accession No. YP_006181877.1, L-lactate dehydrogenase from *Halobacillus* sp. BAB-2008 represented by GenBank Accession No. WP_008633175.1, the L-lactate dehydrogenase from *Geobacillus* sp. WCH70 represented by GenBank Accession No. YP_002948666.1, the lactate dehydrogenase from *Geobacillus caldoxylosilyticus* represented by GenBank Accession No. WP_017436539.1, the L-lactate dehydrogenase from *Anoxybacillus flavithermus* represented by GenBank Accession No. WP_003394005.1, the lactate dehydrogenase from *Anoxybacillus kamchatkensis* represented by GenBank Accession No. WP_019416922.1, and the lactate dehydrogenase from *Lactococcus lactis* represented by GenBank Accession No. NP_267487, among others. The coding sequences encoding these gene products can be found in GenBank.

Homologs of the *Bacillus subtilis* lactate dehydrogenase also include enzymes having an amino acid sequence at least about 80%, 85%, 90%, 95%, 97%, 98%, 99% or more identical to SEQ ID NO:18. Sequences having these percent identities can be obtained by aligning SEQ ID NO:18 to the sequences of the *Bacillus subtilis* lactate dehydrogenase homologs listed above or otherwise known in the art to determine which residues are amenable to variation (i.e., substitution, deletion, addition, etc.) and the identities of the suitably substituted or added residues.

In some versions, the microorganism is modified to harbor a nucleic acid encoding the lactate dehydrogenase from *Lactococcus lactis* or a homolog thereof. The coding sequence of the lactate dehydrogenase from *Lactococcus lactis* is included in GenBank under accession number NC_002662.1 (Gene ID 1114981, complement of positions 1369224-1370201). A codon-optimized version of the coding sequence preferred for expression in cyanobacteria is represented by SEQ ID NO:21. The gene product of the lactate dehydrogenase from *Lactococcus lactis* is included in GenBank under accession number NP_267487 and has an amino acid sequence represented by SEQ ID NO:22.

Exemplary homologs of the lactate dehydrogenase from *Lactococcus lactis* include but are not limited to the L-lactate dehydrogenase from *Lactococcus lactis* subsp. *cremoris* UC509.9 represented by GenBank Accession No. YP_006999682.1, the lactate dehydrogenase from *Lactococcus lactis* represented by GenBank Accession No. WP_021165426.1, the L-lactate dehydrogenase from *Lactococcus lactis* represented by GenBank Accession No. AAB51677.1, the L-lactate dehydrogenase from *Lactococcus lactis* represented by GenBank Accession No. AAB51679.1, lactate dehydrogenase from *Lactococcus lactis* represented by GenBank Accession No. AAA25172.1, the lactate dehydrogenase from *Lactococcus lactis* subsp. *cremoris* TIFN6 represented by GenBank Accession No. EQC54698.1, the L-lactate dehydrogenase from *Streptococcus anginosus* C238 represented by GenBank Accession No. YP_008500777.1, the lactate dehydrogenase from *Streptococcus anginosus* represented by GenBank Accession No. WP_003029659.1, the lactate dehydrogenase from *Lactococcus garvieae* represented by GenBank Accession No. WP_003135756.1, the lactate dehydrogenase from *Streptococcus anginosus* represented by GenBank Accession No. WP_003042963.1, the malate/lactate dehydrogenases from *Streptococcus anginosus* represented by GenBank Accession No. WP_022525868.1, the L-lactate dehydrogenase from *Streptococcus intermedius* C270 represented by GenBank Accession No. YP_008497003.1, the L-lactate dehydrogenase from *Lactococcus garvieae* ATCC 49156 represented by GenBank Accession No. YP_004779491.1, the lactate dehydrogenase from *Lactococcus garvieae* represented by GenBank Accession No. WP_019293709.1, the L-lactate dehydrogenase from *Streptococcus uberis* 0140J represented by GenBank Accession No. YP_002562208.1, the L-lactate dehydrogenase from *Streptococcus parauberis* KCTC 11537 represented by GenBank Accession No. YP_004478812.1, the L-lactate dehydrogenase from *Streptococcus intermedius* B196 represented by GenBank Accession No. YP_008512752.1, the lactate dehydrogenase from *Streptococcus pseudoporcinus* represented by GenBank Accession No. WP_007891460.1, the L-lactate dehydrogenase from *Streptococcus iniae* SF1 represented by GenBank Accession No. YP_008056778.1, the L-lactate dehydrogenase from *Streptococcus intermedius* JTH08 represented by GenBank Accession No. YP_006469731.1, the lactate dehydrogenase from *Streptococcus anginosus* represented by GenBank Accession No. WP_003069027.1, the lactate dehydrogenase from *Streptococcus porcinus* represented by GenBank Accession No. WP_003084658.1, the lactate dehydrogenase from *Streptococcus didelphis* represented by GenBank Accession No. WP_018365941.1, the L-lactate dehydrogenase from *Streptococcus pyogenes* M1 GAS represented by GenBank Accession No. NP_269302.1, the L-lactate dehydrogenase from *Streptococcus constellatus* subsp. *pharyngis* C1050 represented by GenBank Accession No. YP_008498899.1, the L-lactate dehydrogenase from *Streptococcus constellatus* subsp. *pharyngis* C232 represented by GenBank Accession No. YP_008495295.1, the L-lactate dehydrogenase from *Streptococcus equi* subsp. *zooepidemicus* MGCS10565 represented by GenBank Accession No. YP_002123389.1, the L-lactate dehydrogenase from *Streptococcus dysgalactiae* subsp. *equisimilis* GGS_124 represented by GenBank Accession No. YP_002996624.1, the L-lactate dehydrogenase from *Streptococcus equi* subsp. *equi* 4047 represented by GenBank Accession No. YP_002746472.1, the lactate dehydrogenase from *Streptococcus marimammalium* represented by GenBank Accession No. WP_018369606.1, the lactate dehydrogenase from *Streptococcus canis* represented by GenBank Accession No. WP_003048552.1, the lactate dehydrogenase from *Lactococcus raffinolactis* represented by GenBank Accession No. WP_003140351.1, the lactate dehydrogenase from *Streptococcus ictaluri* represented by GenBank Accession No. WP_008089442.1, the lactate dehydrogenase from *Streptococcus iniae* represented by GenBank Accession No. WP_017794816.1, the lactate dehydrogenase from *Streptococcus merionis* represented by GenBank Accession No. WP_018372720.1, the L-lactate dehydrogenase from *Streptococcus dysgalactiae* subsp. *equisimilis* 167 represented by GenBank Accession No. YP_008629609.1, and the lactate dehydrogenase from *Bacillus subtilis* represented by GenBank Accession No. NP_388187, among others. The coding sequences encoding these gene products can be found in GenBank.

Homologs of the *Lactococcus lactis* lactate dehydrogenase also include enzymes having an amino acid sequence at least about 80%, 85%, 90%, 95%, 97%, 98%, 99% or more identical to SEQ ID NO:22. Sequences having these percent identities can be obtained by aligning SEQ ID NO:22 to the sequences of the *Lactococcus lactis* lactate dehydrogenase homologs listed above or otherwise known in the art to determine which residues are amenable to variation (i.e., substitution, deletion, addition, etc.) and the identities of the suitably substituted or added residues.

Figure 12B:
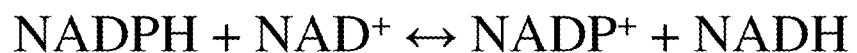
FIG. 12B depicts an equation of the reaction catalyzed by pyridine nucleotide transhydrogenase.

In some versions of the invention, the microorganism is modified to express or increase expression of a transhydrogenase. Preferred transhydrogenases are pyridine nucleotide transhydrogenases, including the enzymes classified under EC 1.6.1.1, 1.6.1.2, and 1.6.1.3. Pyridine nucleotide transhydrogenases convert NAD and NADPH to and from NADH and NADP$^+$. See FIG. 12B. Soluble (as opposed to membrane-bound) pyridine nucleotide transhydrogenases are preferred. Other transhydrogenases that produce either NADH or NADPH as a byproduct are also acceptable. Modifying a microorganism to express or increase expression of a transhydrogenase is preferred when the microorganism is modified to express or increase expression of a lactate dehydrogenase. In some versions, the microorganism is modified to harbor a nucleic acid encoding the soluble pyridine nucleotide transhydrogenase from *E. coli* (particularly *E. coli* K12 MG1655) or a homolog thereof. The coding sequence of the soluble pyridine nucleotide transhydrogenase from *E. coli* K12 MG1655 is included in GenBank under accession number U00096.3 (positions 4159390 to 4160790) and is represented by SEQ ID NO:19. The gene product of the soluble pyridine nucleotide transhydrogenase from *E. coli* K12 MG1655 is included in GenBank under accession number NP_418397 and is represented by SEQ ID NO:20.

Exemplary homologs of the soluble pyridine nucleotide transhydrogenase from *E. coli* K12 MG1655 include but are not limited to the soluble pyridine nucleotide transhydrogenase from *Escherichia coli* HS represented by GenBank Accession No. YP_001460757.1, the pyridine nucleotide-disulfide oxidoreductase family protein from *Escherichia coli* represented by GenBank Accession No. WP_001705589.1, the soluble pyridine nucleotide transhydrogenase from *Escherichia coli* represented by GenBank Accession No. WP_001120797.1, the pyridine nucleotide transhydrogenase from *Escherichia coli* represented by GenBank Accession No. WP_024228022.1, the soluble pyridine nucleotide transhydrogenase from *Escherichia coli* represented by GenBank Accession No. WP_001120803.1, the soluble pyridine nucleotide transhydrogenase from *Shigella flexneri* 2a str. 2457T represented by GenBank Accession No. NP_838918.2, the soluble pyridine nucleotide transhydrogenase from *Escherichia coli* CFT073 represented by GenBank Accession No. NP_756777.1, the soluble pyridine nucleotide transhydrogenase from *Escherichia coli* represented by GenBank Accession No. WP_023278586.1, the soluble pyridine nucleotide transhydrogenase from *Escherichia coli* represented by GenBank Accession No. WP_021576626.1, the soluble pyridine nucleotide transhydrogenase from *Escherichia coli* represented by GenBank Accession No. WP_021541750.1, the soluble pyridine nucleotide transhydrogenase from *Escherichia coli* represented by GenBank Accession No. WP_001403311.1, the soluble pyridine nucleotide transhydrogenase *Escherichia coli* represented by GenBank Accession No. WP_001120823.1, soluble pyridine nucleotide transhydrogenase from *Escherichia coli* represented by GenBank Accession No. WP_001120830.1, the soluble pyridine nucleotide transhydrogenase from *Escherichia coli* represented by GenBank Accession No. WP_021549795.1, the pyridine nucleotide-disulfide oxidoreductase family protein from *Escherichia coli* represented by GenBank Accession No. WP_001385008.1, soluble pyridine nucleotide transhydrogenase from *Escherichia coli* represented by GenBank Accession No. WP_001120811.1, the soluble pyridine nucleotide transhydrogenase *Escherichia coli* 536 represented by GenBank Accession No. YP_672034.1, the soluble pyridine nucleotide transhydrogenase from *Escherichia coli* represented by GenBank Accession No. WP_001120808.1, the soluble pyridine nucleotide transhydrogenase from *Shigella boydii* Sb227 represented by GenBank Accession No. YP_410260.2, the soluble pyridine nucleotide transhydrogenase from *Escherichia coli* represented by GenBank Accession No. WP_021539635.1, the pyridine nucleotide-disulfide oxidoreductase family protein from *Escherichia coli* represented by GenBank Accession No. WP_001546140.1, the soluble pyridine nucleotide transhydrogenase from *Escherichia coli* represented by GenBank Accession No. WP_001545096.1, the soluble pyridine nucleotide transhydrogenase from *Shigella sonnei* Ss046 represented by GenBank Accession No. YP_312883.2, the pyridine nucleotide transhydrogenase from *Escherichia coli* represented by GenBank Accession No. WP_024197343.1, the pyridine nucleotide transhydrogenase from *Escherichia coli* represented by GenBank Accession No. WP_024172841.1, the pyridine nucleotide-disulfide oxidoreductase family protein from *Escherichia coli* represented by GenBank Accession No. WP_001646069.1, the pyridine nucleotide-disulfide oxidoreductase family protein from *Escherichia coli* represented by GenBank Accession No. WP_001561736.1, the pyridine nucleotide-disulfide oxidoreductase family protein from *Escherichia coli* represented by GenBank Accession No. WP_001406381.1, the soluble pyridine nucleotide transhydrogenase from *Shigella flexneri* represented by GenBank Accession No. WP_001120814.1, the soluble pyridine nucleotide transhydrogenase from *Shigella flexneri* represented by GenBank Accession No. WP_001120826.1, the soluble pyridine nucleotide transhydrogenase from *Shigella flexneri* 1235-66 represented by GenBank Accession No. EIQ63659.1, the soluble pyridine nucleotide transhydrogenase from *Escherichia albertii* represented by GenBank Accession No. WP_001120820.1, the soluble pyridine nucleotide transhydrogenase from *Shigella flexneri* represented by GenBank Accession No. WP_001120827.1, the soluble pyridine nucleotide transhydrogenase from *Shigella dysenteriae* Sd197 represented by GenBank Accession No. YP_405233.2, the soluble pyridine nucleotide transhydrogenase from *Salmonella enterica* represented by GenBank Accession No. WP_001120792.1, the soluble pyridine nucleotide transhydrogenase from *Citrobacter rodentium* ICC168 represented by GenBank Accession No. YP_003367222.1, the soluble pyridine nucleotide transhydrogenase from *Salmonella enterica* subsp. *enterica* serovar Choleraesuis str. SC-B67 represented by GenBank Accession No. YP_219002.1, the soluble pyridine nucleotide transhydrogenase from *Salmonella enterica* subsp. *enterica* serovar Heidelberg str. SL476 represented by GenBank Accession No. YP_002048124.1, the soluble pyridine nucleotide transhydrogenase from *Enterobacter cloacae* subsp. *dissolvens* SDM represented by GenBank Accession No. YP_006479868.1, the soluble pyridine nucleotide transhydrogenase from *Citrobacter* represented by GenBank Accession No. WP_016155291.1, the soluble pyridine nucleotide transhydrogenase from *Shigella flexneri* 1235-66 represented by GenBank Accession No. EIQ78768.1, and the pyridine nucleotide transhydrogenase from *Enterobacter asburiae* LF7a represented by GenBank Accession No. YP_004830801.1, among others. The coding sequences encoding these gene products can be found in GenBank.

Homologs of the *E. coli* K12 MG1655 soluble pyridine nucleotide transhydrogenase also include enzymes having an amino acid sequence at least about 80%, 85%, 90%, 95%, 97%, 98%, 99% or more identical to SEQ ID NO:20.

Sequences having these percent identities can be obtained by aligning SEQ ID NO:20 to the sequences of the *E. coli* K12 MG1655 soluble pyridine nucleotide transhydrogenase homologs listed above or otherwise known in the art to determine which residues are amenable to variation (i.e., substitution, deletion, addition, etc.) and the identities of the suitably substituted or added residues.

Other genetic modifications of the microorganism of the present invention include any of those described in U.S. Pat. No. 8,048,624 to Lynch, U.S. Pub. 2011/0125118 to Lynch, and U.S. Pub. 2010/0210017 to Gill et al., all of which are attached hereto. See also Warnecke et al. *Metabolic Engineering* (2010) 12:241-250. The genetic modifications in these references may be to enhance organic acid tolerance and/or increase organic acid production. The microorganism of the present invention may also be modified with homologs of any of the genes, constructs, or other nucleic acids discussed in the above references. Non-limiting examples of the genes that may be modified or introduced include tyrA, aroA, aroB, aroC, aroD, aroE, aroF, aroG, aroH, aroK, aroL, aspC, entA, entB, entC, entD, entE, entF, folA, folB, folC, folD, folE, folK, folP, menA, menB, menC, menD, menE, menF, pabA, pabB, pabC, pheA, purN, trpA, trpB, trpC, trpD, trpE, tyrB, ubiA, ubiB, ubiC, ubiD, ubiE, ubiF, ubiG, ubiH, ubiX, and ydiB, or homologs thereof. A non-limiting example of a pathway that may be modified includes the chorismate superpathway. These genes and pathways are primarily but not exclusively related to the production and tolerance of 3HP.

Exogenous, heterologous nucleic acids encoding enzymes to be expressed in the microorganism are preferably codon-optimized for the particular microorganism in which they are introduced. Codon optimization can be performed for any nucleic acid by a number of programs, including "GENEGPS"-brand expression optimization algorithm by DNA 2.0 (Menlo Park, Calif.), "GENEOPTIMIZER"-brand gene optimization software by Life Technologies (Grand Island, N.Y.), and "OPTIMUMGENE"-brand gene design system by GenScript (Piscataway, N.J.). Other codon optimization programs or services are well known and commercially available.

In addition to the microorganism itself, other aspects of the present invention include methods of producing organic acids with the microorganisms of the present invention. The methods involve culturing the microorganism in conditions suitable for growth of the microorganism. The microorganism either directly produces the organic acid or acids of interest or produces organic-acid precursors from which the organic acid or acids of interest are spontaneously converted. Such conditions include providing suitable carbon sources for the particular microorganism along with suitable micronutrients. For eukaryotic microorganisms and heterotrophic bacteria, suitable carbon sources include various carbohydrates. Such carbohydrates may include biomass or other suitable carbon sources known in the art. For phototrophic bacteria, suitable carbon sources include $CO_2$, which is provided together with light energy.

The microorganism of the present invention is capable of being cultured in high concentrations of the organic acid or acids that the organism is configured to produce. This enables increased production of the organic acid or acids of interest. The microorganism can be cultured in the presence of an organic acid in an amount up to the MIC for that organic acid. Various MICs for exemplary organic acids are described herein. Accordingly, the microorganisms of the invention (i.e., *Synechococcus* sp., *Prochlorococcus* sp., *Synechocystis* sp., etc.) can be cultured in the presence of at least about 10 μM, 25 μM, 50 μM, 75 μM, 100 μM, 250 μM, 500 μM, 750 μM, 1 mM, 25 mM, 50 mM, 70 mM, 75 mM, 100 mM, 125 mM, or 150 mM acrylic acid; at least about 10 mM, 25 mM, 50 mM, 75 mM, 100 mM, 150 mM, 200 mM, 250 mM, 260 mM, 300 mM, or 350 mM 3HP; at least about 250 μM, 500 μM, 750 μM, 1 mM, 25 mM, 50 mM, 75 mM, 100 mM, 150 mM, 200 mM, 250 mM, 300 mM, 350 mM, 400 mM, 450 mM, or 500 mM propionic acid; and/or at least about 10 μM, 25 μM, 50 μM, 75 μM, 100 μM, 250 μM, 500 μM, 750 μM, 1 mM, 25 mM, 50 mM, 70 mM, 75 mM, 100 mM, 125 mM, 150 mM, 200 mM, 250 mM, 300 mM, 350 mM, 400 mM, 450 mM, or 500 mM lactic acid. Such culturing preferably occurs at a pH of about 8.

The microorganisms of the invention may be modified as described herein to increase production of any of the organic acids described herein. The term "increase," whether used to refer to an increase in production of an organic acid, an increase in expression of an enzyme, etc., generally refers to an increase from a baseline amount, whether the baseline amount is a positive amount or none at all.

The microorganism of the invention may be configured to produce 3HP to a concentration of at least about 1 μM, 10 μM, 20 μM, 30 μM, 40 μM, 50 μM, 60 μM, 65 μM, 70 μM, 80 μM, 90 μM, 100 μM or more and/or up to about 10 μM, 20 μM, 30 μM, 40 μM, 50 μM, 60 μM, 65 μM, 70 μM, 80 μM, 90 μM, 100 μM, 200 μM or more. The microorganism of the invention may be configured to produce 3HP at a rate of at least about 0.01 mg/L/Day, 0.05 mg/L/Day, 0.1 mg/L/Day, 0.25 mg/L/Day, 0.5 mg/L/Day, 0.75 mg/L/Day, 1 mg/L/Day, 2.5 mg/L/Day, 5 mg/L/Day, 10 mg/L/Day or more and/or up to about 0.05 mg/L/Day, 0.1 mg/L/Day, 0.25 mg/L/Day, 0.5 mg/L/Day, 0.75 mg/L/Day, 1 mg/L/Day, 2.5 mg/L/Day, 5 mg/L/Day, 10 mg/L/Day, 15 mg/L/Day or more. The microorganism of the invention may be configured to convert at least about 0.1%, 0.5%, 1%, 1.5%, 2%, 2.5%, 3%, 4.5%, 5%, 10%, 15% or more of consumed carbon to 3HP and/or convert up to about 0.5%, 1%, 1.5%, 2%, 2.5%, 3%, 4.5%, 5%, 10%, 15%, 20%, 25%, 30% or more of consumed carbon to 3HP.

The microorganism of the invention may be configured to produce lactic acid to a concentration of at least about 0.1 mM, 0.5 mM, 1 mM, 2 mM, 3 mM, 4 mM, 5 mM, 6 mM, 7 mM, 8 mM, 9 mM, 10 mM, 12 mM, 15 mM, 20 mM, or more and/or up to about, 0.5 mM, 1 mM, 2 mM, 3 mM, 4 mM, 5 mM, 6 mM, 7 mM, 8 mM, 9 mM, 10 mM, 12 mM, 15 mM, 20 mM, 30 mM or more. The microorganism of the invention may be configured to produce lactic acid at a rate of at least about 10 mg/L/Day, 50 mg/L/Day, 100 mg/L/Day, 150 mg/L/Day, 200 mg/L/Day, 250 mg/L/Day, 260 mg/L/Day, 300 mg/L/Day, or more and/or up to about 50 mg/L/Day, 100 mg/L/Day, 150 mg/L/Day, 200 mg/L/Day, 250 mg/L/Day, 260 mg/L/Day, 300 mg/L/Day, 350 mg/L/Day, or more. The microorganism of the invention may be configured to convert at least about 1%, 5%, 10%, 15%, 20%, 25%, 30%, 45%, 50% or more of consumed carbon to lactic acid and/or convert up to about 5%, 10%, 15%, 20%, 25%, 30%, 45%, 50%, 60% or more of consumed carbon to lactic acid.

Some versions of the invention include using acsA or a homolog thereof as a counter selection marker. The acsA or homolog thereof provides sensitivity to the organic acids acrylic acid, 3HP, and propionic acid. By replacing the native copy of acsA or homolog thereof with a gene of interest through double homologous recombination, one can select for cells which have gone through the recombination event by plating on acrylic acid or another organic acid as described herein. Acrylic acid is preferred because it has the lowest MIC value and requires the lowest concentration for selection. Through this method, one can introduce a gene or operon of interest onto a chromosome without the need for antibiotics.

Additionally, one can plate on a higher organic acid concentration, i.e., one closer to the MIC value of the acsA mutant strain, to cure the strain of interest of any copies of the wild type chromosome. This is of particular interest because it can be difficult to create a homozygous strain using antibiotics as the selection agent.

One version comprises using acsA or homolog thereof as a counter selection marker for introducing DNA fragments of interest into the acsA or homolog locus. An exemplary version is shown in FIG. 1A. A host 10 is transformed with either linear DNA fragments or plasmid DNA comprising a sequence of interest 12 flanked by an upstream homologous sequence 14 and a downstream homologous sequence 16. For introducing the sequence of interest 12 into the acsA locus, the upstream homologous sequence 14 is preferably homologous to a region 15 5' of the acsA or homolog 19 on the host chromosome 18, and the downstream homologous sequence 16 is preferably homologous to a region 17 3' of the ascsA or homolog 19 on the host chromosome 18. The homologous sequences 14,16 are preferably at least about 25-base pairs (bp), about 50-bp, about 100-bp, about 200-bp, about 300-bp, about 400-bp, or about 500-bp long. The transformed culture is then plated in a concentration of an organic acid sufficient to select for transformed cells. In preferred versions, the transformed culture is plated in a sub-MIC concentration of an organic acid, such as a concentration greater than 0% the MIC but less than about 20% the MIC, about 40% the MIC, about 50% the MIC, about 60% the MIC, or about 70% the MIC. After colonies appear, the colonies are then plated on a higher concentration of the organic acid to ensure homozygosity.

Figure 1B:
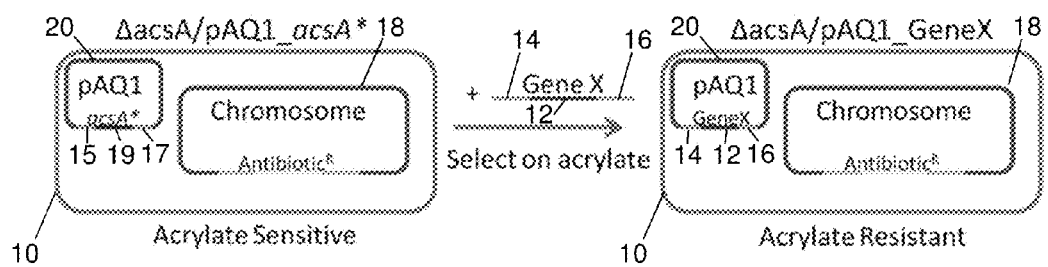
FIG. 1B depicts a schema for using acsA or a homolog thereof as a selection marker for introducing a DNA fragment of interest into a locus other than the acsA or homolog chromosomal locus.

Another version comprises using the acsA gene or homolog thereof as a counter selection marker to introduce DNA fragments of interest into loci other than an acsA or homolog locus without leaving an antibiotic resistance marker. An exemplary version is shown in FIG. 1B. The version shown in FIG. 1B is similar to that shown in FIG. 1A except that the acsA or homolog thereof 19 is not at the normal chromosomal locus. In the specific case of FIG. 1B, a homolog of acsA, acsA*, is included on a non-chromosomal plasmid 20. The acsA or homolog thereof 19 can also be at a locus on the chromosome 18 other than the native acsA or homolog locus. The upstream homologous sequence 14 in FIG. 1B is homologous to a region 15 5' of the acsA or homolog 19 on the non-chromosomal plasmid 20, and the downstream homologous sequence 16 is homologous to a region 17 3' of the acsA or homolog 19 on the on the non-chromosomal plasmid 20.

To increase the utility of acsA as a counter selection marker, two point mutations can be made, T144C and G150C. These point mutations maintain the same amino acid sequence but break up a run of base pairs that create a loss of function mutation hot spot. By creating these mutations, the background mutation frequency of this gene is reduced. This mutant version of acsA, acsA*, can be incorporated onto a non-chromosomal plasmid, such as the endogenous plasmid pAQ1 of a ΔacsA strain of PCC 7002. This base strain allows for incorporating a gene or operon of interest onto the pAQ1 plasmid without the use of antibiotics and quickly creating a homozygous strain.

The elements and method steps described herein can be used in any combination whether explicitly described or not.

The singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the following claims.

EXAMPLES

Summary of the Examples

One of the potential applications of metabolic engineering is the use of cyanobacteria to photosynthetically produce commodity chemicals traditionally derived from petroleum. In particular, acrylic acid has been identified as a high-value product that could be biologically derived. Unfortunately, a viable metabolic pathway has not previously been identified for its direct production.

As described in further detail below, a mutation resulting in increased tolerance to 3HP was discovered through investigating the metabolism of a sulfur compound, dimethylsulfoniopropionate (DMSP), by *Synechococcus* sp. PCC 7002 (PCC 7002). PCC 7002 was grown in the presence of DMSP to determine if it could be metabolized. This surprisingly resulted in the accumulation of acrylic acid, a by-product of DMSP metabolism, showing that *Synechococcus* sp. can produce acrylic acid. The accumulation of acrylic acid in the growth medium caused a stall in growth of the cyanobacteria, suggesting it had a toxic effect. After an additional incubation period, growth began to resume. It was originally hypothesized that the ability to grow in the presence of acrylic acid was the result of an adaptation to the stress through altered gene regulation. This hypothesis was later invalidated after an experiment was performed involving growing "unadapted" cells on solid medium containing acrylic acid. The number of colonies on the plate relative to a control suggested that a loss of function mutation was occurring that resulted in the ability to grow in the presence of acrylic acid. Additionally, all mutants obtained through growth in the presence of acrylic acid had increased tolerance levels to 3HP. The increase in tolerance caused by the mutation resulted in a strain of cyanobacteria constituting a platform for either 3HP or acrylic acid production.

Steps were taken to identify the site of the mutation. An RNA sequencing experiment was performed to characterize differential gene expression in the presence of either DMSP or acrylic acid. This data set was used to identify genes that had single base pair mutations relative to the wild type strain. Through this analysis, mutations were identified in the gene acsA. In order to determine if acsA was involved in acrylic acid and 3HP toxicity, a strain of PCC 7002 was created that had a deletion of the acsA gene. This strain, PCC 7002 ΔacsA, had increased MIC values compared to wild type PCC 7002. These experiments determined that it is a loss of function of acsA that results in increased tolerance. The gene acsA was annotated as an acetyl-CoA ligase.

In order to demonstrate the utility of the ΔacsA strain, a pathway for producing 3HP was introduced into both the wild type PCC 7002 and ΔacsA strains. Several pathways exist for the production of 3HP from central metabolites. The chosen pathway involves an enzyme from the $CO_2$ fixation pathway of the thermophilic bacterium *Chloroflexus aurantiacus*. In this pathway, malonyl-CoA is converted to 3HP through a two-step reaction catalyzed by the enzyme malonyl-CoA reductase. Results have shown that expression of malonyl-CoA reductase confers the ability to produce 3HP on the order of 50 µM.

The result of these experiments is an engineered strain of PCC 7002 that can produce 3HP and is more tolerant to 3HP than wild type PCC 7002 or other cyanobacterial species. Further work will increase the yield of 3HP. The approach to increasing yield will involve further metabolic engineering and optimizing of culturing conditions. To further engineer this strain, expression of the malonyl-CoA reductase will be optimized and genes related to making malonyl-CoA will be over-expressed. Additionally, the current and further engineered strains will be cultured in a photobioreactor in order to monitor 3HP production under optimal growth conditions, and culture parameters will be adjusted to increase yields. The outcome of this work will be a strain of cyanobacteria with optimized culturing conditions that will result in a competitive yield of 3HP.

Background and Significance of Examples
Engineering Bacteria to Produce Commodity Chemicals A current focus of metabolic engineering and synthetic biology is the development of new methods for producing commodity chemicals that are traditionally produced from petroleum [1,2]. Demand for methods of bioconversion of renewable resources (biomass or $CO_2$) to these compounds has increased due to price volatility and reliance on foreign production of oil, concerns of increasing atmospheric $CO_2$, and increased consumer demand for "green" and sustainable products. An example of recent commercial success is the production of 1,3-propanediol (a precursor of nylon-like materials) by DuPont via *Escherichia coli* fermentation of corn sugar [3].

Another compound that could be produced from renewable sources is acrylic acid. Acrylic acid, traditionally produced through the oxidation of propene, is used in coatings, finishes, plastics, and superabsorbent polymers [4]. US demand for acrylic acid continues to grow, exceeding $1 \times 10^9$ kg/year, and is outpacing current production [4]. For this reason, non-petroleum based, sustainable methods for producing acrylic acid would be of value. Unfortunately, a thermodynamically favorable pathway for complete biological production of acrylic acid has not been identified [5]. An alternative route would be biological production of 3-hydroxypropionic acid (3HP), followed by a non-biological catalytic conversion to acrylic acid. Additionally, 3HP can be converted to other commodity chemicals including acrylamide and 1,3-propanediol [6]. One company, OPX Biotechnologies, has developed a bio-based technology for producing acrylic acid, via *Escherichia coli* fermentation of sugars to 3HP [7].

Cyanobacteria as an Alternative to Heterotrophic Bacteria

One of the concerns of using heterotrophic bacteria and yeast for fuel and chemical production is the use of food based commodities as feedstock. As the global population continues to grow and the cost of agricultural commodities continues to rise, an alternative route for biological production of commodity chemicals may be needed. An attractive alternative is to use cyanobacteria to convert $CO_2$ and light energy directly into chemical products. Using $CO_2$ rather than organic carbon as an input circumvents the problem of using agricultural commodities and could potentially decrease costs. Species of cyanobacteria are susceptible to genetic modification and have well studied metabolisms [8,9]. Recently, cyanobacteria have been engineered to produce a variety of chemicals and fuels including ethanol, hydrogen, isobutyraldehyde, isoprene, sugars, and fatty acids [10-14].

In order for cyanobacteria to be effective host systems for chemical production, they will have to produce the compound of interest in high titers and have improved resistance to end product toxicity. As presented below, a mutant strain of cyanobacteria was isolated with dramatically increased tolerance to acrylic acid and 3HP. This mutation was identified through exploring the role cyanobacteria play in metabolism of the marine sulfur compound dimethylsulfoniopropionate (DMSP).

Metabolism of the Sulfur Compound DMSP

DMSP is an organic sulfur compound produced by eukaryotic algae and plants that accounts for 1-10% of primary productivity in the oceans [16]. DMSP has been shown to act as an osmoprotectant, antioxidant, predator deterrent, and a sink for reduced sulfur in marine eukaryotic algae [17,18]. Upon its release into the water, DMSP is metabolized by bacterioplankton for use as a carbon and reduced sulfur source [19]. The catabolism of DMSP has the potential to supply 1-15% of total carbon demand and nearly all of the sulfur demand for these bacterial communities [20]. Additionally, cyanobacteria have been shown to account for 10-34% of total DMSP assimilation in light-exposed waters [21,22].

DMSP is broken down through two major pathways. These pathways involve either direct cleavage of DMSP into dimethylsulfide (DMS) and acrylic acid or an initial demethylation followed by a cleavage reaction to form methanethiol and acrylic acid [16, 23-25]. Methanethiol is then used as a reduced sulfur source in methionine biosynthesis, while acrylic acid can be further metabolized into 3HP and used as a carbon source [26,27]. Additionally, release of DMS into the atmosphere from marine waters has been identified as a key intermediate in the cycling of terrestrial and marine sulfur pools [28]. While several genes have been identified in DMSP metabolism, none have been found in cyanobacteria.

Recent studies have shown that two different groups of cyanobacteria are involved in the metabolism of DMSP. These studies demonstrated that both *Synechococcus* and *Prochlorococcus* species are capable of assimilating radio labeled DMSP and methanethiol. In addition, four pure strains of *Synechococcus* were analyzed for DMSP assimilation. Two of the four strains were able to transport and assimilate DMSP, while another produced DMS [22]. Of the species of cyanobacteria currently being used in metabolic engineering, only one, *Synechococcus* sp. PCC 7002, is found in marine environments and potentially exposed to DMSP.

Example 1

Acrylic Acid is Produced from Incubation of DMSP with PCC 7002

Metabolism of DMSP can result in the accumulation of several metabolites, including acrylic acid and 3HP, and may alter growth patterns due to its use as a carbon and sulfur source. PCC 7002 was cultured in the presence of 5 mM DMSP and analyzed for the presence of acrylic acid and 3HP. Growth was determined by monitoring OD730 while metabolic byproducts were measured through high pressure liquid chromatography (HPLC) and gas chromatography (GC).

Figure 3:
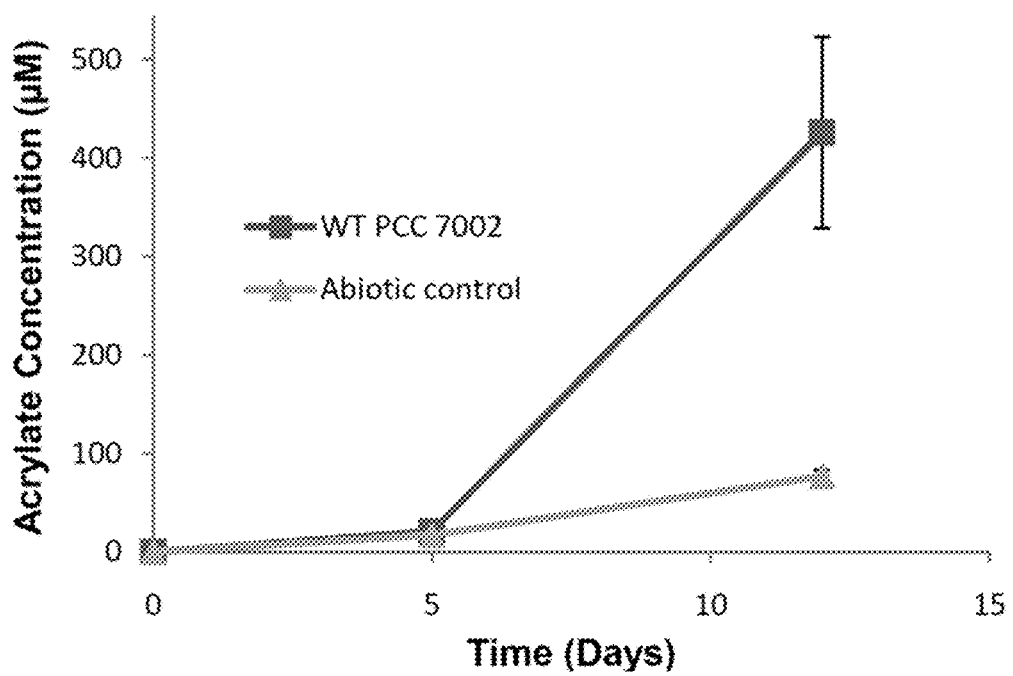
FIG. 3 depicts acrylate production from DMSP as a function of time for *Synechococcus* sp. PCC 7002 and an abiotic control.
Figure 4B:
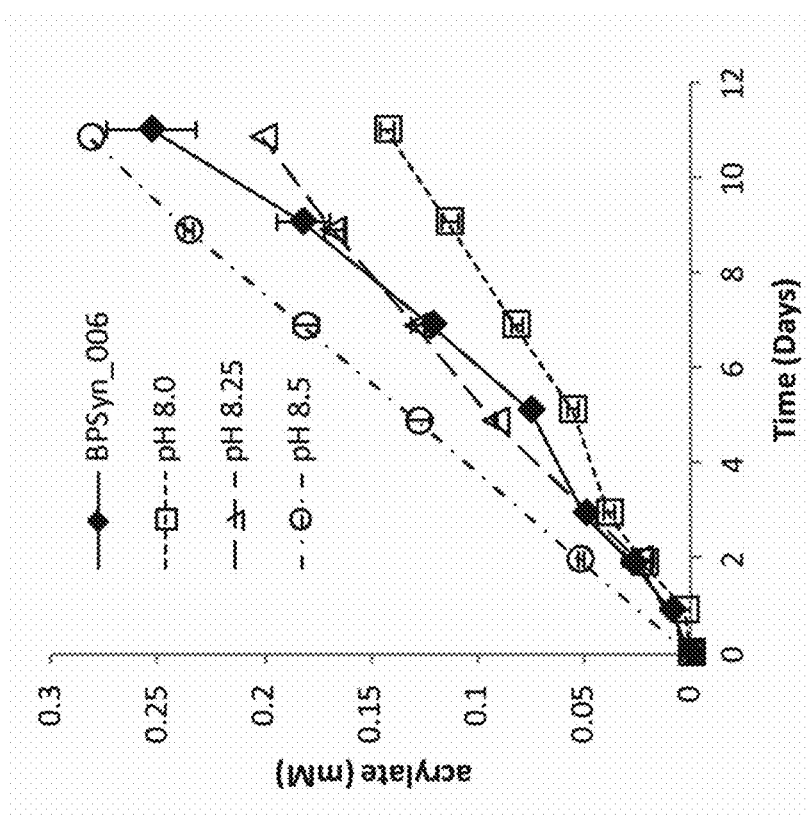
FIG. 4B depicts acrylic acid accumulation over time from cultivation of BPSyn_006 with 5 mM DMSP and abiotic controls with 5 mM DMSP at pH 8.0, 8.25, and 8.5. The rate of DMSP degradation to acrylic acid increases with an increase in pH.
Figure 4A:
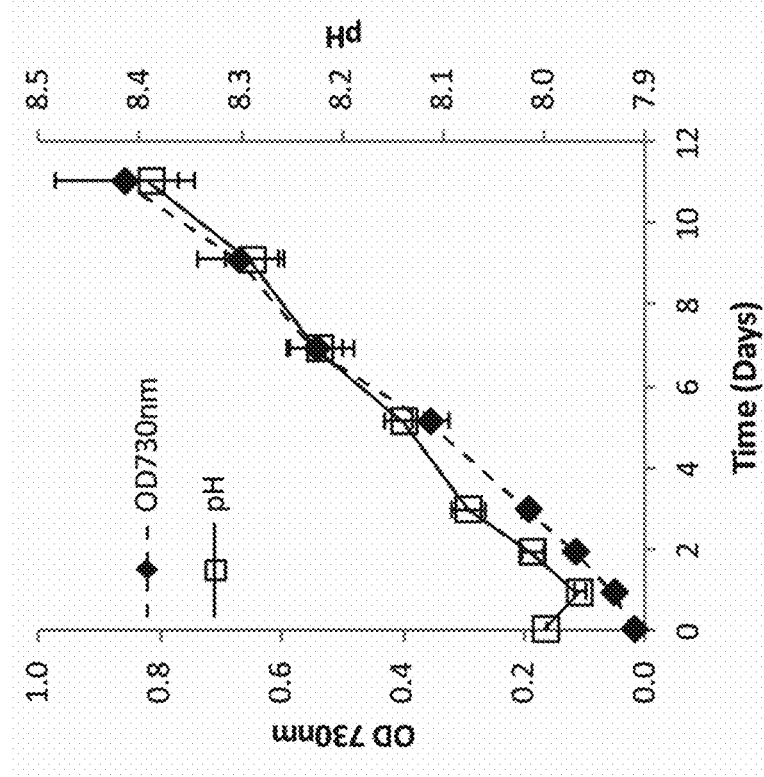
FIG. 4A depicts growth of BPSyn_006 (a ΔacsA strain of *Synechococcus* sp. PCC 7002 having a barcode sequence in place of the acsA gene (PCC 7002 acsA::BC)) and pH as a function of time in $CO_2$-limited conditions. Cultivation of BPSyn_006 with 5 mM DMSP under $CO_2$-limited conditions results in an increase in pH over time.

During incubation with DMSP, an increase in OD730 similar to a control culture was observed for several doubling events, followed by a delay in increased OD730 (FIG. 2A). HPLC analysis determined that during the initial growth period acrylic acid was being produced, although not at a rate significantly beyond an abiotic control (FIG. 3). However, extended incubation of PCC 7002 with DMSP resulted in an increase in acrylic acid concentrations beyond the abiotic control (FIG. 3). PCC 7002 does not contain genes with homology to those known to be involved in DMSP metabolism, but DMSP has been previously shown to slowly degrade to dimethylsulfide and acrylic acid at an alkaline pH [48,49]. The data presented in FIGS. 4A-B support a hypothesis that DMSP breakdown is abiotic and is enhanced by the increased pH resulting from cultivation of PCC 7002 under $CO_2$ limitation. The cultures in this study were not agitated or supplemented with bubbled air, creating a $CO_2$ limited environment. When grown in the presence of 5 mM acrylic acid, PCC 7002 exhibited a long lag followed by growth at a rate equal to the control (FIG. 2B). Both delays in increasing OD730 were linked by the presence of acrylic acid, suggesting that acrylic acid was causing growth inhibition. The eventual increase in OD730 in both cultures was due to spontaneous mutants within the population which were able to grow without inhibition. Sub-culturing of the mutant pool derived from wild type (WT) PCC 7002 grown with DMSP into medium containing acrylic acid resulted in no delay in growth (FIG. 2C). From these experiments it was concluded that DMSP incubated in the presence of PCC 7002 results in the production of acrylic acid, acrylic acid concentrations less than 5 mM are inhibitory, and spontaneous mutants can arise that are not inhibited by this concentration of acrylic acid.

Example 2

Acrylic Acid and 3HP Cause Toxicity at Low Concentrations

Accumulation of organic acid anions in the cytoplasm of bacteria has been shown to block metabolic pathways and arrest growth [32,33]. In addition to blocking metabolic pathways, high concentrations of organic acids have been shown to reduce the proton motive force through dissociation across the membrane [34]. Because of this, the toxicity of organic acids generally increases with the hydrophobicity of the compound [35]. The minimum inhibitory concentrations (MIC) for PCC 7002, *Synechococcus* sp. PCC 7942, and *Synechocystis* sp. PCC 6803 were determined for acrylic acid, 3HP, and propionic acid at a pH of about 8 (Table 1). In all three species, acrylic acid was significantly more toxic than propionic acid, which was more toxic than 3HP. Furthermore, the toxicity of acrylic acid (pKa 4.35) to PCC 7002 was shown to be pH dependent, with toxicity increasing with decreasing pH. The low MIC for acrylic acid explains why cultures grown with DMSP become growth inhibited. Cultures with DMSP only show growth inhibition when the accumulating acrylic acid concentration reaches inhibitory concentrations. This suggests that acrylic acid and not DMSP causes the inhibition of growth. The eventual increase in OD730 suggests that mutations can arise to overcome this inhibition.

TABLE 1

Minimum inhibitory concentration of organic acids in three cyanobacteria.

| Species | Acrylic Acid | 3HP | Propionic Acid |
|---|---|---|---|
| *Synechococcus* sp. PCC 7942 | 3 μM | 2 mM | 250 μM |
| *Synechocystis* sp. PCC 6803 | 50 μM | No Data | 250 μM |
| *Synechococcus* sp. PCC 7002 | 25 μM | 10 mM | 4 mM |
| [1]PCC 7002 A+ | 7 mM | No Data | No Data |

Minimum inhibitory concentration is defined as the concentration at which no increase in $OD_{730}$ was observed.
[1]Strain A+ was isolated from an agar plate containing 5 mM acrylic acid.

Example 3

A Mutation in an Acetyl-CoA Ligase Gene Increases Tolerance to Acrylic Acid and 3HP When a dense culture of PCC 7002 was plated onto solid medium containing acrylic acid, colonies resulting from spontaneous mutants uninhibited by acrylic acid were observed. The mutation frequency when selecting for growth on 50 μM acrylic acid was $7 \times 10^{-6}$. When selecting for growth on 5 mM acrylic acid, the mutation frequency was $4 \times 10^{-6}$. The mutation frequency is the frequency that a mutant with a given phenotype is found within the population of a culture. For example a mutation frequency of $1 \times 10^{-6}$ suggests that in a population of $1 \times 10^8$ cells, there are 100 mutants. The observed mutation frequencies are suggestive of a loss of function mutation. All mutants obtained from medium containing 50 μM acrylic acid were able to grow on 5 mM acrylic acid. In addition, these colonies were able to grow in media containing concentrations of propionic acid and 3HP that were above the WT PCC 7002 MIC values. One of the mutants, PCC 7002 A+, was analyzed to determine to what degree the tolerance to organic acids had increased. MIC values for this strain are presented in Table 1. Tolerance to acrylic acid increased about 280-fold over WT PCC 7002 MIC values. Increased tolerance to 3HP and propionic acid was also observed (data not shown). Due to the increased tolerance to all three organic acids, the mutation may affect a gene that links the metabolism of acrylic acid, 3HP, and propionic acid.

In addition to looking at gene expression levels, the results from the RNA-sequencing experiment were used to identify mutations that resulted in increased tolerance to acrylic acid. An analysis for single nucleotide permutations (SNP) on the data set for each condition was performed. In order to identify potential mutation candidates, two basic assumptions were made. First, growth in cultures containing DMSP and acrylic acid would require the same mutation. Second, the mutation is a base pair change, not a deletion or insertion. From the SNP analysis, mutations in five candidate genes were identified. One of these candidates was annotated as an acetyl-CoA ligase (acsA). The mutation resulted in the change of a highly conserved tryptophan residue to a leucine (W49L) in *Synechococcus* sp. PCC 7002. The mutation changes an FWGE amino acid sequence in *Synechococcus* sp. PCC 7002 to an FLGE amino acid sequence. This mutation was a result of a G146T substitution in the acsA coding sequence. The mutation was present in ~60% of reads that aligned to this segment of the open reading frame in both the DMSP and acrylic acid cultures. Manual inspection of control alignment data determined that this allele was only present in cultures containing DMSP and acrylic acid. The correlate of W49 is conserved in the acsA of *Escherichia coli* (GenBank NP_418493.1) and Bacillus subtilis (GenBank NP_390846.1), among others, suggesting it is integral to a functional protein See, e.g., Table 2.

TABLE 2

Conservation of W49 and surrounding residues of Synechococcus sp. PCC 7002 acsA in acetyl-CoA ligases of E. coli K12 and P. fulva

| Organism | Gene | Protein Sequence | SEQ ID NO: |
|---|---|---|---|
| Synechococcus sp. PCC 7942 | acsA | F-W-G-E | Residues 48-51 of SEQ ID NO: 2 |
| E. coli K12 | Acetyl-CoA ligase | F-W-G-E | Residues 39-41 of SEQ ID NO: 9 |
| P. fulva | Acetyl-CoA ligase | F-W-G-E | Residues 38-41 of SEQ ID NO: 10 |

The W49L mutation residue resulted in an insoluble protein (data not shown) and, therefore, a non-functional protein. These data led to the hypothesis that loss of function of acsA would result in the observed increase in organic acid tolerance.

Without being limited by mechanism, it was hypothesized that the AcsA acetyl-CoA ligase may have a substrate specificity that would allow it to add a coenzyme A (CoA) to all three organic acids, and that the CoA bound acids or downstream metabolism of these CoA bound acids caused toxicity.

This hypothesis was tested by creating a knockout mutant of the acsA gene. This knockout was created by transforming wild type PCC 7002 with a DNA construct that would replace the acsA gene with an antibiotic resistance marker through homologous recombination. The resulting mutant, ΔacsA, was challenged with concentrations of acrylic acid, 3HP, and propionic acid above WT PCC 7002 MIC levels. In each case the ΔacsA mutant was able to grow without inhibition, including in the presence of >500 mM 3HP. Additionally, the ΔacsA mutant did not show any growth defects relative to wild type. These results show that loss of function of the acyl-CoA ligase increases the tolerance of PCC 7002 to acrylic acid and 3HP.

Figure 5:
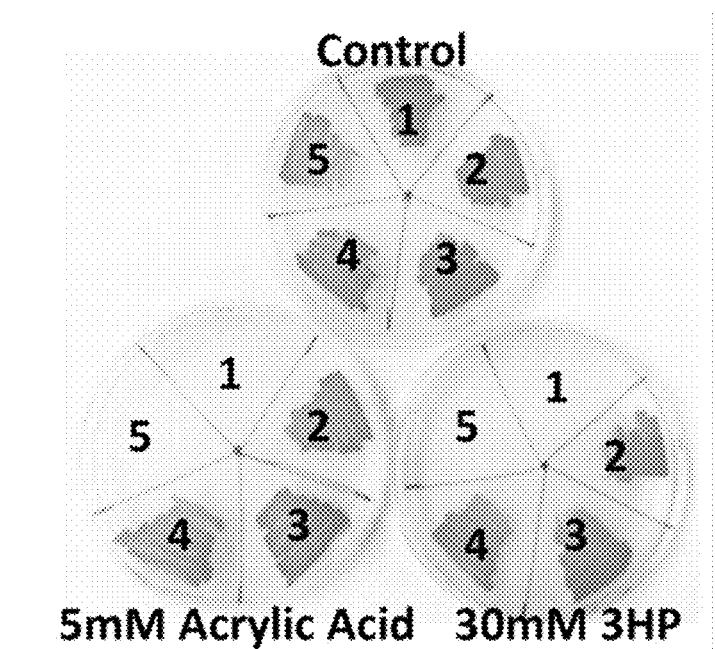
FIG. 5 depicts plating of wild-type *Synechococcus* sp. PCC 7002, a mutant generated from growth in the presence of acrylic acid, a ΔacsA mutant, a ΔacsA mutant comprising the pAQ1 plasmid containing acsAW49L, and a ΔacsA mutant comprising the pAQ1 plasmid containing acsA on media containing no organic acid, 5 mM acrylic acid, or 30 mM 3-hydroxypropionic acid (3HP).

To confirm this phenotype is the result of the deletion mutation, a complementation mutant was created by integrating a copy of acsA into a plasmid native to PCC 7002 ΔacsA. A corresponding mutant harboring a copy of acsA-W49L was also constructed. In the presence of acrylic acid, no strains harboring wild-type acsA were capable of growing while those harboring the mutant acsA were able to grow (FIG. 5).

In addition, the acsA gene was heterologously expressed in E. coli for protein purification and the substrate specificity was determined for AcsA in vitro (see below).

From these results, several conclusions can be drawn. DMSP is converted to acrylic acid by PCC 7002. Spontaneous mutations occur within the population that results in a drastically increased tolerance to acrylic acid, 3HP, and propionic acid. One mutation that can result in this phenotype is a loss of function or deletion of the acsA gene, which codes for an acetyl-CoA ligase.

Example 4

Deletion and Complementation Studies

Deletion and complementation studies were performed in various Synechococcus spp. and Synechocystis spp. The results are shown in Table 3. Replacement of the gene acsA in Synechococcus sp. PCC 7002 with an antibiotic resistance marker (aadA) resulted in a dramatic increase in tolerance to acrylic acid, 3-hydroxypropionic acid (3HP), and propionic acid. An identical level of increase was observed when acsA was replaced with a 20 base-pair barcode sequence. This phenotype was complemented in an acsA deletion strain by expression of acsA under the native promoter in another locus on the chromosome (glpK). Complementation resulted in the restored sensitivity to both acrylic acid and 3HP. The phenotype was only partially complemented upon expression of acsAW49L from the glpK locus, showing that the AW49L mutation does not result in a complete loss of AcsA activity.

Homologous genes were identified in the cyanobacteria Synechocystis sp. PCC 6803 (sll0542; SEQ ID NOS:3 and 4) and Synechococcus sp. PCC 7942 (SYNPCC7942_1342; SEQ ID NOS:5 and 6). Replacement of the gene sll0542 in PCC 6803 with an antibiotic resistance marker resulted in an increase in tolerance to acrylic acid similar to the deletion of acsA in PCC 7002. When selecting for growth of Synechocystis sp. PCC 6803 on 50 μM acrylic acid, the mutation frequency was $2 \times 10^{-6}$.

TABLE 3

Minimum inhibitory concentrations of organic acids

| Species | acrylic acid (mM) | 3-HP (mM) | Propionic acid (mM) |
|---|---|---|---|
| Synechococcus sp. PCC 7942 | 0.003 | 2 | 0.25 |
| Synechocystis sp. PCC 6803 | 0.050 | >35 | 0.25 |
| PCC 6803 sll0542::KmR | 70 | <50 | No Data |
| Synechococcus sp. PCC 7002 | 0.025 | 10 | 4 |
| PCC 7002 acsA::aadA | 70 | 260 | >400 |
| PCC 7002 acsA::BC* | 70 | 260 | No Data |
| PCC 7002 acsA::BC glpK:: acsA aadA) | 0.015 | 15 | No Data |
| PCC 7002 acsA::BC glpK:: acsAW49L aadA) | 7 | No Data | No Data |

*BC, 20 base-pair barcode

Example 5

Substrate Specificity of AcsA

The tolerance of PCC 7002 to acrylic acid and 3HP was dramatically increased by the deletion of the acetyl-CoA ligase gene (acsA). To obtain information regarding the AcsA-dependent toxicity, the substrate specificity of AcsA was determined.

Acyl-CoA ligase purification: Escherichia coli BL21 containing plasmid pET28b with acsA were grown in 50 mL of LB to an $OD_{600nm}$ of 0.6 and induced with 1 mM IPTG. The induced culture was shaken at 37° C. for 3 hrs. The culture was centrifuged and the resulting cell pellet was frozen at −20° C. The cell pellet was processed with Novagen Bug-Buster Protein Extraction Reagent (Part No. 70584-3). The resulting soluble protein fraction was used for His-tag purification using Ni-NTA agarose beads (Qiagen) and Pierce 0.8-mL centrifugation columns (Part No. 89868). Washes were done with 50 mM $NaH_2PO_4$, 300 mM NaCl, and 30 mM imidizole pH 8.0. The his-tagged protein was eluted with 50 mM $NaH_2PO_4$, 300 mM NaCl, and 250 mM imidizole pH 8.0. The insoluble fraction from the protein extraction was washed twice with BugBuster reagent followed by incubation with 400 μL 8M urea, 100 mM Tris-HCl, and 100 mM β-mercaptoethanol pH 8.2 for 30 min. The resulting solution was centrifuged at 16,000×g and the supernatant was collected. Protein fractions were run on a SDS-PAGE gel. His-tag purified protein fractions used in the acyl-CoA ligase assay were concentrated and buffered exchanged using an Amicon Ultra-4 centrifugation column. The buffer used for enzyme storage contained 0.1 M NaH$_2$PO$_4$, 1 mM EDTA, and 10% v/v glycerol.

Figure 6:
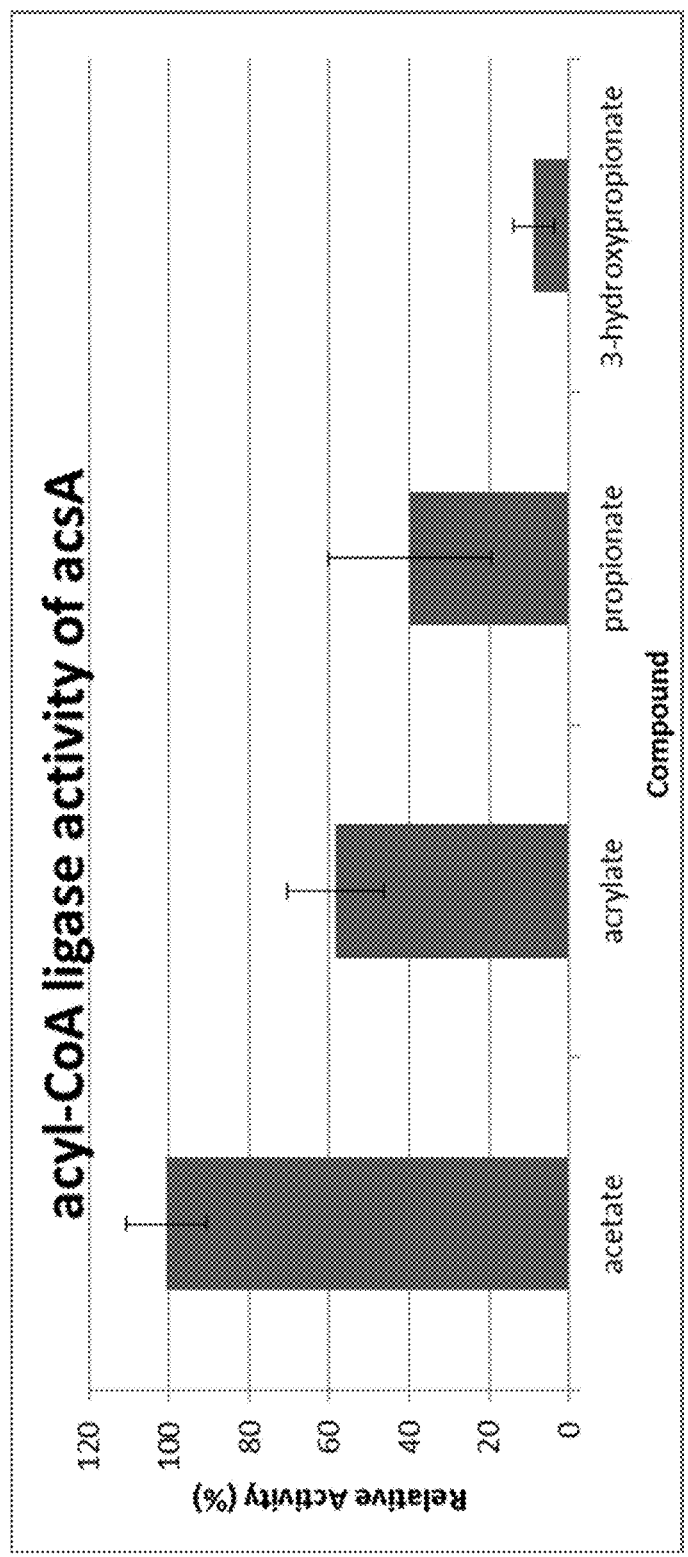
FIG. 6 depicts relative acyl-CoA ligase activity of AcsA for acetate, acrylate, propionate, and 3-hydroxypropionate (3HP).

Acyl-CoA ligase activity assay: Acyl-CoA ligase activity was determined by measuring the loss of free Coenzyme A (CoA) over time using Ellman's reagent. (Riddles P W, Blakeley R L, & Zerner B (1979) Ellman's reagent: 5,5′-dithiobis(2-nitrobenzoic acid—a reexamination. *Analytical Biochemistry* 94(1):75-81.) The enzyme reaction contained 10 mM ATP, 8 mM MgCl$_2$, 3 mM CoA, 0.1 M NaH$_2$PO$_4$, 1 mM EDTA, and 2 mM of the organic acid species. The concentration of AcsA in the reaction was 500 nM. Relative activity was determined by the amount of CoA consumed in 4 min relative to an acetate control. As shown in FIG. 6, AcsA has an activity towards acetate, acrylic acid, propionate, and 3HP.

Example 6

Use of acsA as a Counter-Selection Marker

The sensitivity of PCC 7002 to acrylic acid due to the activity of AcsA allows for one to directly integrate DNA fragments into the acsA locus and select for acrylic acid tolerance. This method results in integration into the PCC 7002 without the use of an antibiotic resistance marker. The use of antibiotic resistance markers is limited by the number of markers available and their tendency to result in heterozygous strains. PCC 7002 carries between 4-6 copies of the chromosome and the use of resistance markers can result in strains with a mixture of native and modified chromosomes. Use of acsA as a counter-selection marker can quickly produce homozygous strains.

Figure 8A:
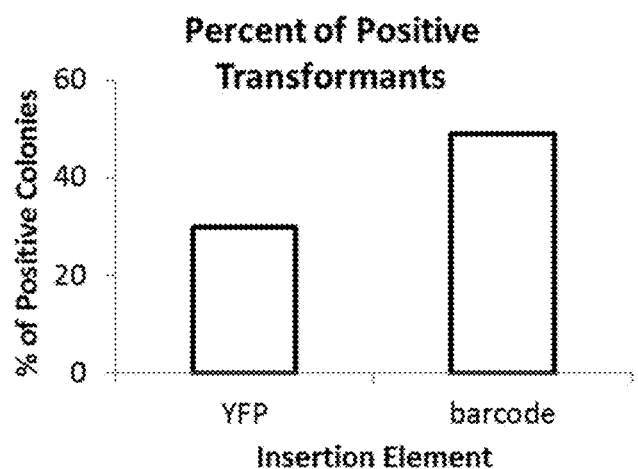
FIG. 8A depicts the percent of colonies positive for yellow fluorescent protein (YFP) or a barcode sequence resulting from use of acsA as a counter selection marker upon introducing the YFP or the barcode sequence into the chromosomal acsA locus of *Synechococcus* sp. PCC 7002.

The acsA gene was used as a counter-selection marker to introduce DNA fragments of interest into the acsA loci on the chromosome, thereby deleting acsA without leaving an antibiotic resistance marker. Wild type PCC 7002 was transformed with barcode DNA or DNA encoding yellow fluorescent protein (YFP), each flanked with 500 base-pair sequences homologous to regions directly 5′ and 3′ of acsA. The transformed culture was then plated on 50 μM acrylic acid. Colonies appeared after 3 days. The colonies were patched onto plates containing 50 μM acrylic acid and screened for the presence of the sequence of interest. Integration of the various sequences resulted in 30-50% of colonies being positive integrations. See FIG. 8A. Positive clones were streaked onto plates containing 10 mM acrylic acid. Colonies able to grow in the presence of 10 mM acrylic acid were homozygous for the integration. This method allows for fast and homozygous chromosomal integrations.

Figure 8B:
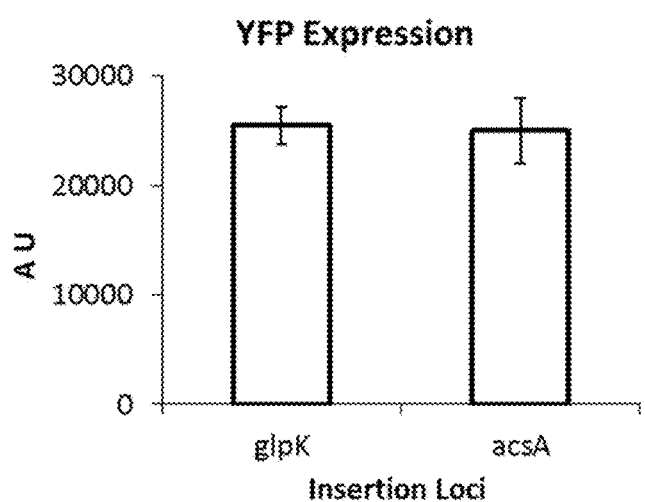
FIG. 8B depicts levels of YFP expression from cells in which YFP was introduced into the glpK chromosomal locus using acsA as a counter selection marker and cells in which YFP was introduced into the acsA chromosomal locus using acsA as a counter selection marker.

The acsA gene was also used as a counter selection marker to introduce DNA fragments of interest into other loci on the chromosome without leaving an antibiotic resistance marker. In an acsA deletion strain of PCC 7002, acsA along with an antibiotic resistance marker was introduced onto the chromosome into the gene glpK. See, e.g., PCC 7002 acsA:BC glpK:: acsA aadA in Table 3. glpK was used as an insertion site because it is a pseudogene in PCC 7002 due to a frameshift mutation. The acsA-resistance marker was then replaced with yellow fluorescent protein (YFP) under the expression of a constitutive promoter. This resulted in a strain of PCC 7002 with YFP integrated onto the chromosome without a residual marker. YFP expressed from the glpK locus was shown to have an equal level of expression to YFP expressed from the acsA locus. See FIG. 8B. These experiments demonstrate the one can directly select for integration into the acsA locus and use acsA as a counter selection tool to make clean integrations elsewhere on the chromosome.

Example 7

Production of 3HP with Engineered PCC 7002

While the ultimate goal is to produce acrylic acid through a single biological catalyst, no complete pathway has previously been demonstrated [5]. As an alternative, 3HP can be biologically derived and then catalytically converted to acrylic acid. A 3HP production pathway was introduced into PCC 7002 ΔacsA and its ability to produce 3HP from CO$_2$ and light energy was analyzed.

Figure 7:
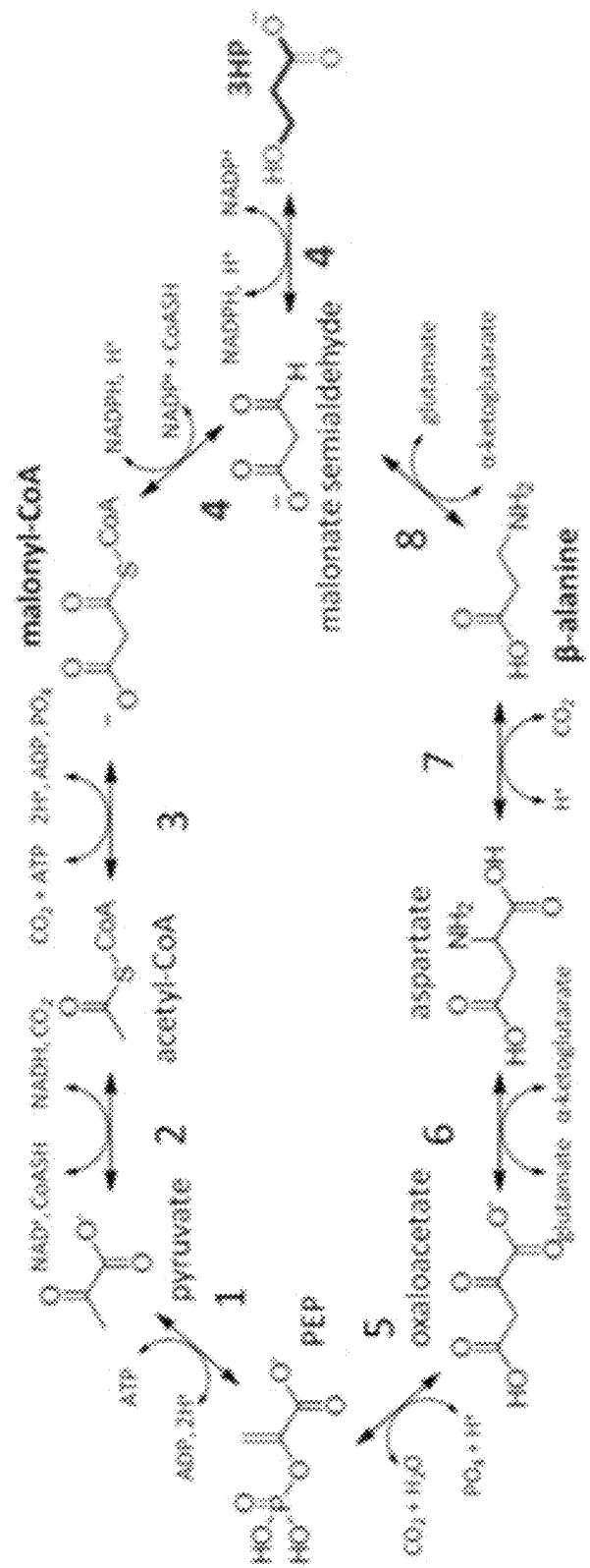
FIG. 7 depicts two 3HP-production pathways, wherein 1 represents pyruvate kinase, 2 represents pyruvate dehydrogenase, 3 represents acetyl-CoA carboxylase, 4 represents malonyl-CoA reductase, 5 represents phosphoenolpyruvate carboxylase, 6 represents aspartate aminotransferase, 7 represents aspartate decarboxylase, and 8 represents β-alanine/α-ketoglutarate aminotransferase.

Effect of a Bifunctional Malonyl-CoA Reductase from *Chloroflexus aurantiacus* on Production of 3HP FIG. 7 outlines two pathways for synthesizing 3HP from phosphoenolpyruvate (PEP). PEP is derived in cyanobacteria through the oxidation of glyceraldehyde 3-phosphate, a product of CO$_2$ assimilation. While both pathways would result in a cofactor imbalance, the route via malonyl-CoA balances out the NADPH derived from the light reactions of photosynthesis and results in the net production of 2 ATP and 2 NADH per 3HP. In order to introduce this pathway into PCC 7002, a malonyl-CoA reductase gene was heterologously expressed. Malonyl-CoA reductase from *Chloroflexus aurantiacus* was cloned into PCC 7002 ΔacsA [44]. *C. aurantiacus* is a phototrophic bacterium that produces 3HP as an intermediate in CO$_2$ fixation [45]. The malonyl-CoA reductase from *Chloroflexus aurantiacus* has been shown to have activity that converts malonyl-CoA to malonate semialdehyde and, in addition, activity that converts malonate semialdehyde to 3HP. The *C. aurantiacus* malonyl-CoA reductase gene was introduced onto a native plasmid under a highly expressed promoter [46]. Integration onto a native plasmid rather than the chromosome ensured a higher copy number of the gene. The native plasmid is required for growth, ensuring that the plasmid was not lost [46]. After integration was confirmed, the ability of the strain to produce 3HP was determined through HPLC. Preliminary results have shown that expressing malonyl-CoA reductase in wild-type PCC 7002 and PCC 7002 ΔacsA confers the ability to produce 3HP on the order of 50 μM. Further experiments will be performed to determine if the ΔacsA strain has an advantage with respect to yield and growth rate. We predict that the ΔacsA strain has an advantage with respect to yield and growth rate.

Figure 9B:
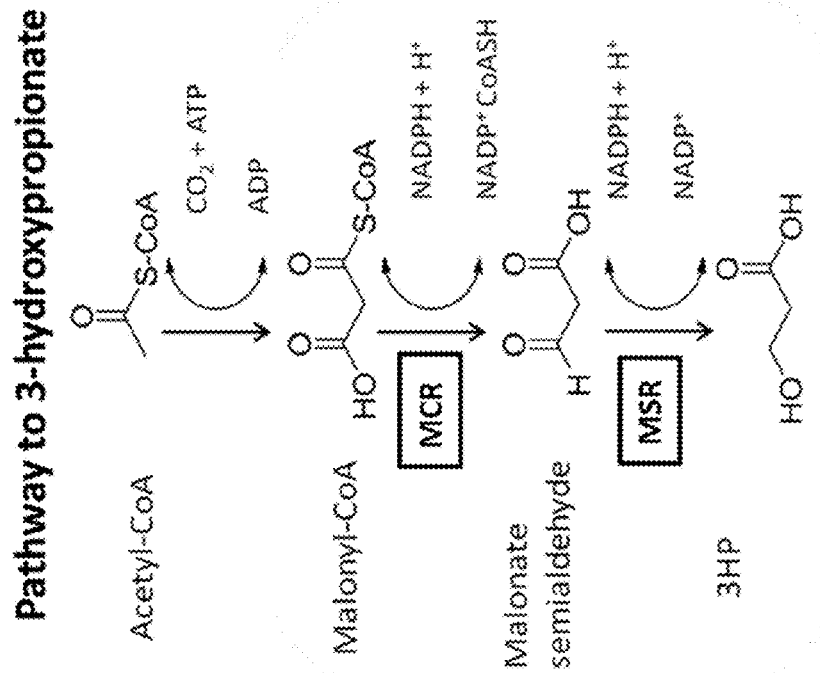
FIG. 9B depicts a schema of the production of 3HP from acetyl-CoA, showing the malonyl-CoA reductase and the malonate semialdehyde reductase steps in detail. "AccABCD" represents acetyl-CoA carboxylase. "MCR" represents malonyl-CoA reductase. "MSR" represents malonate semialdehyde reductase. "AcsA" represents acetyl-CoA synthetase.
Figure 9A:
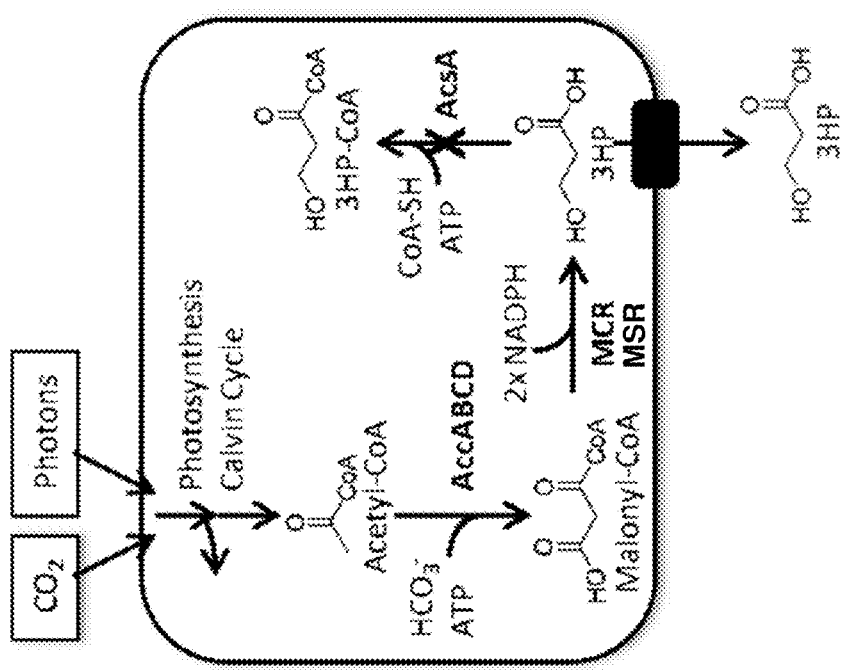
FIG. 9A depicts a schema of the production of 3HP from $CO_2$ and photons (sunlight) in cyanobacteria.

Effect of a Mono Functional Malonyl-CoA Reductase from *Metallosphaera sedula* and a Malonate Semialdehyde Reductase from *Sulfolobus tokodaii* on Production of 3HP As an alternative to producing 3HP by expressing the malonyl-CoA reductase from *Chloroflexus aurantiacus*, 3HP was produced by expressing a mono-functional malonyl-CoA reductase (MCR) from *Sulfolobus tokodaii* and a malonate semialdehyde reductase (MSR) from *Metallosphaera sedula*. Schemas outlining this strategy are shown in FIGS. 9A and 9B.

Figure 10:
FIG. 10 depicts an artificial operon construct configured to express malonyl-CoA reductase and malonate semialdehyde reductase. "$p_{cpc}$BLacOO" represents a LacI-regulatable promoter based on the cyanobacterial cpcB gene promoter. "RBS" represents a ribosome binding site. "MCR" represents a malonyl-CoA reductase coding sequence. "MSR" represents a malonate semialdehyde reductase coding sequence. "LacI" represents a gene for the lac repressor (LacI).

The acsA in *Synechococcus* sp. PCC 7002 was replaced with an artificial operon construct configured to express an N-terminally truncated version of the MCR from *Sulfolobus tokodaii* (SEQ ID NO:13) and the MSR from *Metallosphaera sedula* (SEQ ID NO:16) under IPTG-inducible conditions. The operon (lacOOI_MCR_MSR), shown in FIG. 10, included a LacI-regulatable promoter based on the cyanobacterial cpcB gene promoter ($p_{cpc}$BLacOO), a truncated, codon-optimized MCR coding sequence (SEQ ID NO:12), a codon-optimized MSR coding sequence (SEQ ID NO:15), ribosome binding sites (RBSs) upstream of each of the MCR and MSR coding sequences, and a lad gene. A strain of *Synechococcus* sp. PCC 7002 with acsA replaced with a barcode sequence (PCC 7002 acsA::BC) was generated as a control. The engineered PCC 7002 was grown in 10-ml volumes at a light intensity of 140 µE/m$^2$/s at 35° C. and bubbled with air. Cell growth was monitored by measuring the optical density at 730 nm (OD$_{730}$) using a Spectrophotometer 20 (Milton Roy). The production of 3HP was determined with each generated strain through HPLC.

As shown in Table 4, the control strain (PCC 7002 acsA::BC) was incapable of producing 3HP. By contrast, the strain comprising the artificial operon (PCC 7002 acsA::lacOOI_MCR_MSR) produced 32 µM and 66 µM in the absence and presence, respectively, of 1 mM IPTG.

TABLE 4

Production of 3-HP

| Strain | IPTG (mM) | 3HP (µM) |
|---|---|---|
| PCC 7002 acsA::BC (Control) | 0 | 0 |
| PCC 7002 acsA::lacOOI_MCR_MSR | 0 | 32 |
| PCC 7002 acsA::lacOOI_MCR_MSR | 1 | 66 |

Figure 11:
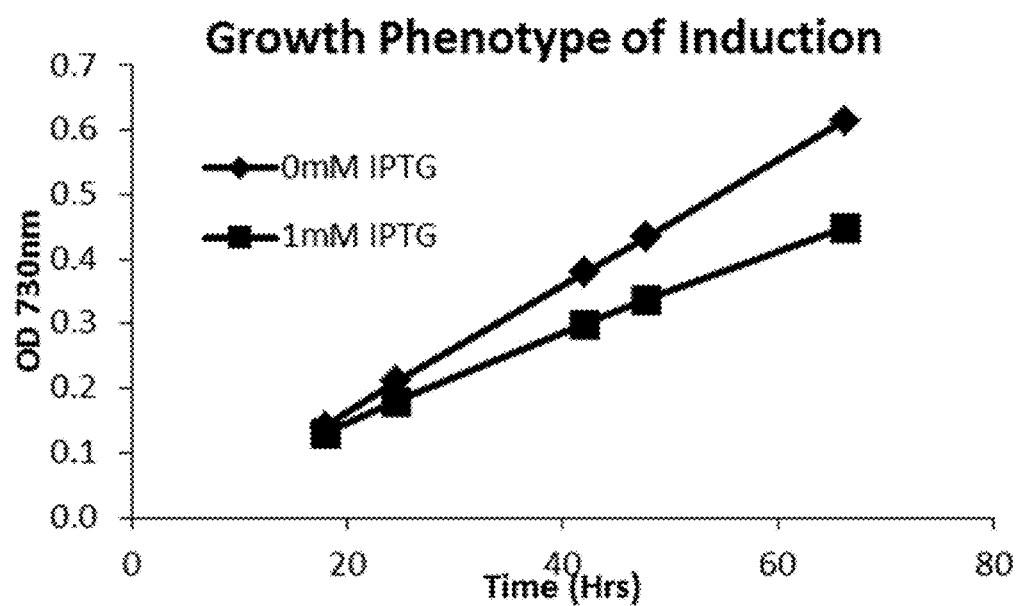
FIG. 11 depicts growth in the presence and absence of 1 mM IPTG as a function of time for *Synechococcus* sp. PCC 7002 lacking acsA and comprising the construct depicted in FIG. 10.

The growth of PCC 7002 acsA::lacOOI_MCR_MSR in both the absence and presence of 1 mM IPTG is shown in FIG. 11.

These data show that PCC 7002 and, more generally, cyanobacteria can be engineered to produce 3HP.

Further Engineering to Increase 3HP Titers

Several strategies can be employed to increase 3HP production. For example, flux through the 3HP production pathway can be increased by overexpressing the acetyl-CoA carboxylase genes, thus increasing the pool of malonyl-CoA. See FIG. 9A. Furthermore, a genome-scale metabolic model can be used to predict genetic modifications that would provide additional flux through the pathway and correct cofactor imbalances [47]. These strategies will potentially increase titers of 3HP to be comparable with production systems using heterotrophic bacteria.

Example 8

Production of Lactate with Engineered PCC 7002

A lactate production pathway was enhanced in PCC 7002 ΔacsA and its ability to produce 3HP from CO$_2$ and light energy was analyzed.

Effect of Lactase Dehydrogenase on Lactate Production

Lactate dehydrogenase catalyzes the conversion from pyruvate to lactate. See FIG. 12A. The acsA in *Synechococcus* sp. PCC 7002 was replaced with a construct configured to express the lactate dehydrogenase from *B. subtilis* (ldh, SEQ ID NOS: 17 and 18) under IPTG-inducible conditions. The resulting strain, PCC 7002 acsA::ldh, was grown in 10-ml volumes with or without 1 mM IPTG at a light intensity of 140 µE/m$^2$/s at 35° C. and bubbled with air containing ambient CO$_2$. Cell growth was monitored by measuring the optical density at 730 nm (OD$_{730}$) using a Spectrophotometer 20 (Milton Roy). Lactate production was determined using methods known in the art.

Figure 13:
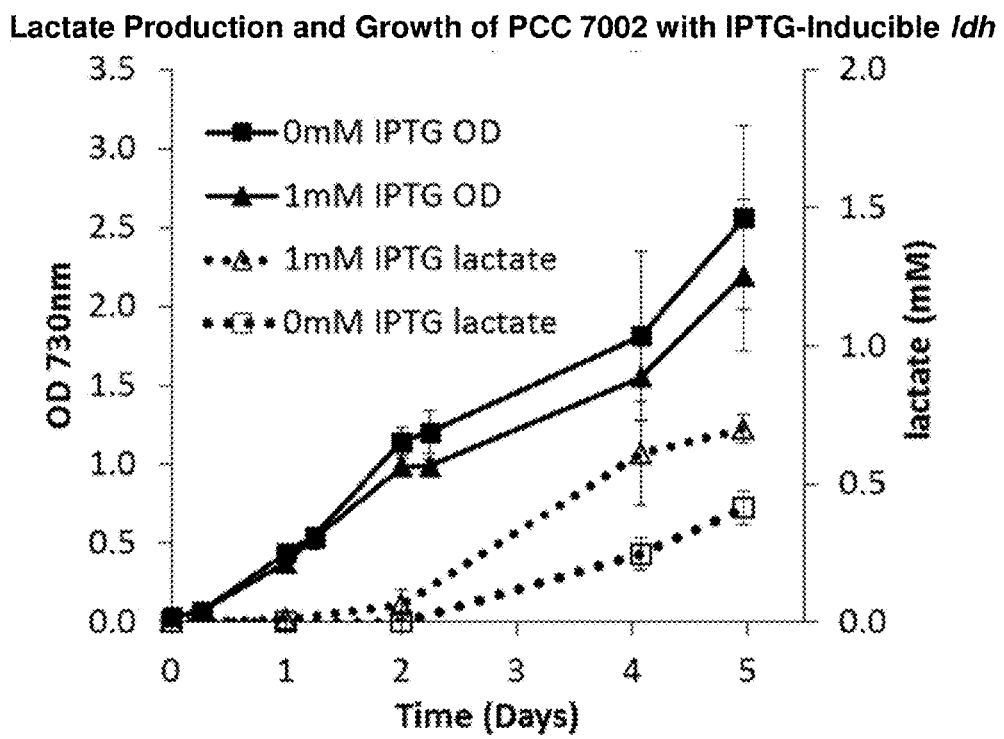
FIG. 13 depicts growth and lactate production in the presence and absence of 1 mM IPTG as a function of time for *Synechococcus* sp. PCC 7002 lacking acsA and comprising an IPTG-inducible lactate dehydrogenase gene with a coding sequence (ldh) from *Bacilllus subtilis*.

Lactate production from PCC 7002 acsA::ldh in the presence and absence of IPTG is shown in FIG. 13 and Table 5, and the growth of PCC 7002 acsA::ldh in the presence and absence of IPTG is shown in FIG. 13. Increasing expression of lactate dehydrogenase increased production of lactate without significantly compromising growth.

TABLE 5

Lactate production from PCC 7002 acsA::ldh in the presence and absence of IPTG

| IPTG | Final Lactate Concentration | Lactate Production Rate | Percent Consumed Carbon Converted to Lactate |
|---|---|---|---|
| − | 0.4 mM (36 mg/L) | 12 mg/L/Day | 2.4% |
| + | 0.7 mM (63 mg/L) | 21 mg/L/Day | 4.5% |

Effect of Lactase Dehydrogenase and a Transhydrogenase on Lactate Production

Pyridine nucleotide transhydrogenases catalyze the conversion of the reducing equivalents NADH and NADPH. See FIG. 12B. NADH is a co-factor in the lactate dehydrogenase reaction. The acsA in *Synechococcus* sp. PCC 7002 was replaced with an artificial operon construct configured to express the lactate dehydrogenase from *B. subtilis* (ldh, SEQ ID NOS: 17 and 18) and a soluble pyridine nucleotide transhydrogenase from *E. coli* (udhA, SEQ ID NOS: 19 and 20) under IPTG-inducible conditions. The resulting strain, PCC 7002 acsA::ldh-udhA, and the PCC 7002 strain replacing acsA with the ldh-only construct, PCC 7002 acsA::ldh, were grown as described above except that 1 mM IPTG was used in all cultures and the cultures were bubbled with air containing 0.5% CO$_2$. Cell growth and lactate production was determined as described above.

Figure 14:
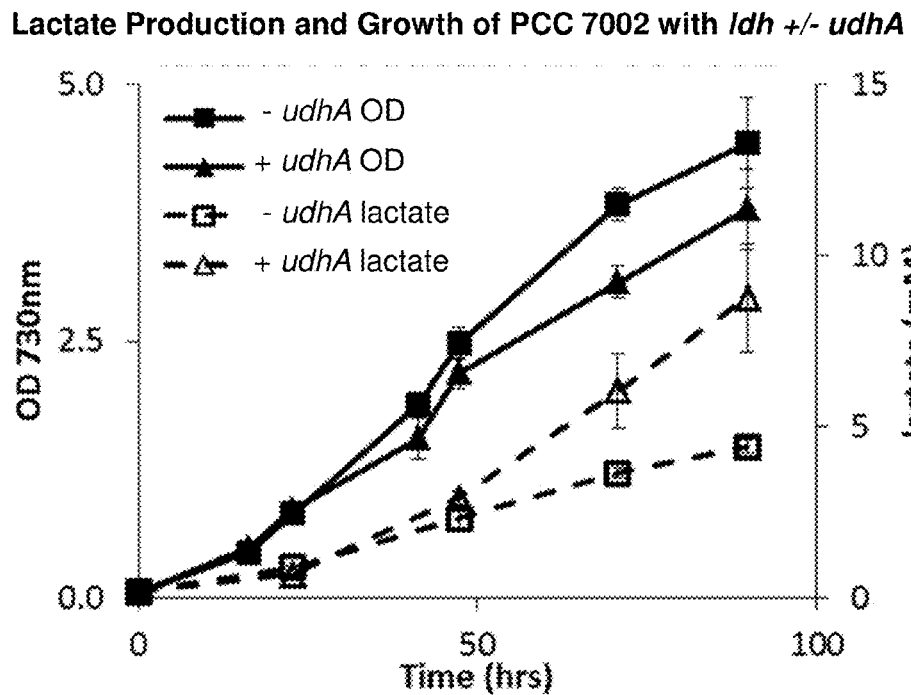
FIG. 14 depicts growth and lactate production in the presence of 1 mM IPTG as a function of time for *Synechococcus* sp. PCC 7002 lacking acsA, comprising an IPTG-inducible lactate dehydrogenase gene with a coding sequence (ldh) derived from *Bacillus subtilis*, and comprising a soluble pyridine nucleotide transhydrogenase gene with a coding sequence (udhA) derived from *Escherichia coli*.

Lactate production from the PCC 7002 acsA::ldh and PCC 7002 acsA::ldh-udhA strains is shown in FIG. 14 and Table 6, and growth of the strains is shown in FIG. 14. Increasing expression of lactate dehydrogenase increased production of lactate without significantly compromising growth. Expressing the transhydrogenase along with the lactate dehydrogenase was capable of significantly increasing lactate production without significantly compromising growth. Notably, the cells expressing the soluble transhydrogenase in addition to the lactate dehydrogenase were able to produce about 1 g/L lactate after 5 days. In addition, about 22% of the fixed carbon was converted to lactate.

TABLE 6

Lactate production from PCC 7002 ΔacsA ldh with and without the udhA soluble transhydrogenase

| udhA | Final Lactate Concentration | Lactate Production Rate | Percent Consumed Carbon Converted to Lactate |
|---|---|---|---|
| − | 4.4 mM (396 mg/L) | 115 mg/L/Day | 8.8% |
| + | 8.9 mM (801 mg/L) | 262 mg/L/Day | 22% |

Effect of the Lactase Dehydrogenase from *Lactococcus lactis* on Lactate Production Expression constructs comprising a codon-optimized coding sequence of the lactase dehydrogenase from *Lactococcus lactis* (ldhA, SEQ ID NOS: 21 and 22) either alone or with the soluble pyridine nucleotide transhydrogenase from *E. coli* (udhA, SEQ ID NOS: 19 and 20) were generated. The constructs will be used to replace the acsA in *Synechococcus* sp. PCC 7002. The resulting strains will be grown as described above. Cell growth and lactate production will be determined as described above. It is predicted that expression of the lactase dehydrogenase from *Lactococcus lactis* will increase lactate production as well as or better than expression of the lactate dehydrogenase from *B. subtilis*.

Conclusions from Examples

Increasing the tolerance to organic acids and engineering the production of commodity chemicals makes biological synthesis of these chemicals from $CO_2$ with cyanobacteria and other microorganisms a viable option.

REFERENCES

1. Keasling, J. D., *Manufacturing Molecules Through Metabolic Engineering. Science*, 2010. 330(6009): p. 1355-1358.
2. Chotani, G., et al., *The commercial production of chemicals using pathway engineering*. Biochimica et Biophysica Acta (BBA)—Protein Structure and Molecular Enzymology, 2000. 1543(2): p. 434-455.
3. Nakamura, C. E. and G. M. Whited, *Metabolic engineering for the microbial production of 1,3-propanediol*. Current Opinion in Biotechnology, 2003. 14(5): p. 454-459.
4. Bauer, W., *Acrylic Acid and Derivatives*. Kirk-Othmer Encyclopedia of Chemical Technology. 2000: John Wiley & Sons, Inc.
5. Straathof, A. J. J., et al., *Feasibility of acrylic acid production by fermentation*. Applied Microbiology and Biotechnology, 2005. 67(6): p. 727-734.
6. Bozell, J. J. and G. R. Petersen, *Technology development for the production of biobased products from biorefinery carbohydrates—the US Department of Energy's "Top 10" revisited*. Green Chemistry, 2010. 12(4): p. 539-554.
7. *OPX nears commercial goal for bio-based acrylic acid* Feb. 28, 2011; Available from: http://www.opxbiotechnologies.com/press/.
8. Thiel, T., *Genetic Analysis of Cyanobacteria*, in *The Molecular Biology of Cyanobacteria*, D. A. Bryant, Editor. 2004, Springer Netherlands. p. 581-611.
9. Ducat, D. C., J. C. Way, and P. A. Silver, *Engineering cyanobacteria to generate high-value products*. Trends in Biotechnology, 2011. 29(2): p. 95-103.
10. Angermayr, S. A., et al., *Energy biotechnology with cyanobacteria*. Current Opinion in Biotechnology, 2009. 20(3): p. 257-263.
11. Atsumi, S., W. Higashide, and J. C. Liao, *Direct photosynthetic recycling of carbon dioxide to isobutyraldehyde*. Nat Biotech, 2009. 27(12): p. 1177-1180.
12. Lindberg, P., S. Park, and A. Melis, *Engineering a platform for photosynthetic isoprene production in cyanobacteria, using Synechocystis as the model organism*. Metabolic Engineering, 2010. 12(1): p. 70-79.
13. Liu, X., J. Sheng, and R. Curtiss III, *Fatty acid production in genetically modified cyanobacteria*. Proceedings of the National Academy of Sciences, 2011.
14. Niederholtmeyer, H., et al., *Engineering Cyanobacteria To Synthesize and Export Hydrophilic Products*. Appl. Environ. Microbiol., 2010. 76(11): p. 3462-3466.
15. Kumar, K., et al., *Development of suitable photobioreactors for $CO_2$ sequestration addressing global warming using green algae and cyanobacteria*. Bioresource Technology, 2011. 102(8): p. 4945-4953.
16. Howard, E. C., et al., *Bacterial Taxa That Limit Sulfur Flux from the Ocean*. Science, 2006. 314(5799): p. 649-652.
17. Stefels, J., *Physiological aspects of the production and conversion of DMSP in marine algae and higher plants*. Journal of Sea Research, 2000. 43(3-4): p. 183-197.
18. Sunda, W., et al., *An antioxidant function for DMSP and DMS in marine algae*. Nature, 2002. 418(6895): p. 317-320.
19. Yoch, D. C., *Dimethylsulfoniopropionate: Its Sources, Role in the Marine Food Web, and Biological Degradation to Dimethylsulfide*. Appl. Environ. Microbiol., 2002. 68(12): p. 5804-5815.
20. Simó R., et al., *Coupled Dynamics of Dimethylsulfoniopropionate and Dimethylsulfide Cycling and the Microbial Food Web in Surface Waters of the North Atlantic*. Limnology and Oceanography, 2002. 47(1): p. 53-61.
21. Vila-Costa, M., et al., *Dimethylsulfoniopropionate Uptake by Marine Phytoplankton*. Science, 2006. 314(5799): p. 652-654.
22. Malmstrom, R. R., et al., *Dimethylsulfoniopropionate (DMSP) Assimilation by Synechococcus in the Gulf of Mexico and Northwest Atlantic Ocean*. Limnology and Oceanography, 2005. 50(6): p. 1924-1931.
23. González, J. M., et al., *Genetics and Molecular Features of Bacterial Dimethylsulfoniopropionate (DMSP) and Dimethylsulfide (DMS) Transformations*, in *Handbook of Hydrocarbon and Lipid Microbiology*, K. N. Timmis, Editor. 2010, Springer Berlin Heidelberg. p. 1201-1211.
24. Howard, E. C., et al., *Abundant and diverse bacteria involved in DMSP degradation in marine surface waters*. Environmental Microbiology, 2008. 10(9): p. 2397-2410.
25. Reisch, C. R., et al., *Novel pathway for assimilation of dimethylsulphoniopropionate widespread in marine bacteria*. Nature, 2011. 473(7346): p. 208-211.
26. Kiene, R. P., et al., *Dimethylsulfoniopropionate and Methanethiol Are Important Precursors of Methionine and Protein-Sulfur in Marine Bacterioplankton*. Appl. Environ. Microbiol., 1999. 65(10): p. 4549-4558.
27. Ansede, J. H., P. J. Pellechia, and D. C. Yoch, *Metabolism of Acrylate to beta-Hydroxypropionate and Its Role in Dimethylsulfoniopropionate Lyase Induction by a Salt Marsh Sediment Bacterium, Alcaligenes faecalis M3A*. Appl. Environ. Microbiol., 1999. 65(11): p. 5075-5081.
28. Simó, R., *Production of atmospheric sulfur by oceanic plankton: biogeochemical, ecological and evolutionary links*. Trends in Ecology & Evolution, 2001. 16(6): p. 287-294.
29. Ross, C. and K. L. V. Alstyne, *INTRASPECIFIC VARIATION IN STRESS-INDUCED HYDROGEN PEROXIDE SCAVENGING BY THE ULVOID MACROALGA ULVA LACTUCA1*. Journal of Phycology, 2007. 43(3): p. 466-474.
30. Latifi, A., M. Ruiz, and C.-C. Zhang, *Oxidative stress in cyanobacteria*. FEMS Microbiology Reviews, 2009. 33(2): p. 258-278.
31. Balasubramanian, R., et al., *Regulatory Roles for IscA and SufA in Iron Homeostasis and Redox Stress Responses in the Cyanobacterium Synechococcus sp. Strain PCC 7002*. J. Bacteriol., 2006. 188(9): p. 3182-3191.
32. Horswill, A. R., A. R. Dudding, and J. C. Escalante-Semerena, *Studies of Propionate Toxicity in Salmonella enterica Identify 2-Methylcitrate as a Potent Inhibitor of Cell Growth*. Journal of Biological Chemistry, 2001. 276(22): p. 19094-19101.
33. Russell, J. B., *Another explanation for the toxicity of fermentation acids at low pH: anion accumulation versus uncoupling*. Journal of Applied Microbiology, 1992. 73(5): p. 363-370.
34. Chemington, C. A., et al., *Organic Acids: Chemistry, Antibacterial Activity and Practical Applications*, in *Advances in Microbial Physiology*, A. H. Rose and D. W. Tempest, Editors. 1991, Academic Press. p. 87-108.
35. Zaldivar, J. and L. O. Ingram, *Effect of organic acids on the growth and fermentation of ethanologenic Escherichia coli LY01*. Journal Name: Biotechnology and Bioengineer- 36. Fridovich, I. and H. M. Hassan, *Paraquat and the exacerbation of oxygen toxicity*. Trends in Biochemical Sciences, 1979. 4(5): p. 113-115.
37. Sakamoto, T., V. B. Delgaizo, and D. A. Bryant, *Growth on Urea Can Trigger Death and Peroxidation of the Cyanobacterium Synechococcus sp. Strain PCC 7002*. Appl. Environ. Microbiol., 1998. 64(7): p. 2361-2366.
38. Steinke, M., et al., *Determinations of dimethylsulphoniopropionate (DMSP) lyase activity using headspace analysis of dimethylsulphide (DMS)*. Journal of Sea Research, 2000. 43(3-4): p. 233-244.
39. Hashimoto, Y., et al., *Nitrile Pathway Involving Acyl-CoA Synthetase*. Journal of Biological Chemistry, 2005. 280 (10): p. 8660-8667.
40. Kasuya, F., K. Igarashi, and M. Fukui, *Participation of a medium chain acyl-CoA synthetase in glycine conjugation of the benzoic acid derivatives with the electron-donating groups*. Biochemical Pharmacology, 1996. 51(6): p. 805-809.
41. MARUYAMA, K. and H. KITAMURA, *Mechanisms of Growth Inhibition by Propionate and Restoration of the Growth by Sodium Bicarbonate or Acetate in Rhodopseudomonas sphaeroides S*. Journal of Biochemistry, 1985. 98(3): p. 819-824.
42. Man, W.-J., et al., *The binding of propionyl-CoA and carboxymethyl-CoA to Escherichia coli citrate synthase*. Biochimica et Biophysica Acta (BBA)—Protein Structure and Molecular Enzymology, 1995. 1250(1): p. 69-75.
43. Boynton, Z. L., G. N. Bennett, and F. B. Rudolph, *Intracellular Concentrations of Coenzyme A and Its Derivatives from Clostridium acetobutylicum ATCC 824 and Their Roles in Enzyme Regulation*. Appl. Environ. Microbiol., 1994. 60(1): p. 39-44.
44. Hugler, M., et al., *Malonyl-Coenzyme A Reductase from Chloroflexus aurantiacus, a Key Enzyme of the 3-Hydroxypropionate Cycle for Autotrophic $CO_2$ Fixation*. J. Bacteriol., 2002. 184(9): p. 2404-2410.
45. Holo, H., *<i>Chloroflexus aurantiacus</i> secretes 3-hydroxypropionate, a possible intermediate in the assimilation of CO<sup>2</sup> and acetate*. Archives of Microbiology, 1989. 151(3): p. 252-256.
46. Xu, Y., et al., *Expression of Genes in Cyanobacteria: Adaptation of Endogenous Plasmids as Platforms for High-Level Gene Expression in <i>Synechococcus</i> sp. PCC 7002*, in *Photosynthesis Research Protocols*, R. Carpentier, Editor. 2011, Humana Press. p. 273-293.
47. Feist, A. M., et al., *Reconstruction of biochemical networks in microorganisms*. Nat Rev Micro, 2009. 7(2): p. 129-143.
48. Visscher, P. T., and H. van Gemerden. 1991. Production and Consumption of Dimethylsulfoniopropionate in Marine Microbial Mats. *Applied and Environmental Microbiology* 57:3237-3242.
49. Dacey, J. W. H., and N. V. Blough. 1987. Hydroxide decomposition of dimethylsulfoniopropionate to form dimethylsulfide. *Geophys. Res. Lett.* 14:1246-1249.
50. Begemann M B, Zess E K, Walters E M, Schmitt E F, Markley A L, Pfleger B F. An organic acid based counter selection system for cyanobacteria. *PLoS One*. 2013 Oct. 1; 8(10):e76594.

We claim:

1. A microorganism comprising:
    a modification that reduces or ablates AcsA activity or AcsA homolog activity in the microorganism; and
    one or more recombinant nucleic acids configured to express an enzyme selected from the group consisting of a lactate dehydrogenase and a transhydrogenase, wherein the microorganism produces an increased amount of lactic acid compared to a corresponding microorganism not comprising the one or more recombinant nucleic acids.

2. The microorganism of claim 1 wherein the microorganism is a bacterium.

3. The microorganism of claim 1 wherein the microorganism is a cyanobacterium.

4. The microorganism of claim 1 wherein the one or more recombinant nucleic acids is configured to express a lactate dehydrogenase and a pyridine nucleotide transhydrogenase.

5. The microorganism of claim 1 wherein the one or more recombinant nucleic acids is configured to express a lactate dehydrogenase selected from the group consisting of a lactate dehydrogenase from *Bacillus subtilis* or a homolog thereof and a lactate dehydrogenase from *Lactococcus lactis* or a homolog thereof.

6. The microorganism of claim 1 wherein the lactate dehydrogenase is selected from the group consisting of a lactate dehydrogenase from *Bacillus subtilis* or a homolog thereof comprising a sequence at least about 80% identical to SEQ ID NO:18 and a lactate dehydrogenase from *Lactococcus lactis* or a homolog thereof comprising a sequence at least about 80% identical to SEQ ID NO:22.

7. The microorganism of claim 1 wherein the lactate dehydrogenase is selected from the group consisting of a lactate dehydrogenase from *Bacillus subtilis* or a homolog thereof comprising a sequence at least about 90% identical to SEQ ID NO:18 and a lactate dehydrogenase from *Lactococcus lactis* or a homolog thereof comprising a sequence at least about 90% identical to SEQ ID NO:22.

8. The microorganism of claim 1 wherein the lactate dehydrogenase is selected from the group consisting of a lactate dehydrogenase from *Bacillus subtilis* or a homolog thereof comprising a sequence at least about 90% identical to SEQ ID NO:18 and a lactate dehydrogenase from *Lactococcus lactis* or a homolog thereof comprising a sequence at least about 90% identical to SEQ ID NO:22.

9. The microorganism of claim 1 wherein the one or more recombinant nucleic acids is configured to express a soluble pyridine nucleotide transhydrogenase from *Escherichia coli* or a homolog thereof.

10. The microorganism of claim 9 wherein the soluble pyridine nucleotide transhydrogenase from *Escherichia coli* or the homolog thereof comprises a sequence at least about 80% identical to SEQ ID NO:20.

11. The microorganism of claim 9 wherein the soluble pyridine nucleotide transhydrogenase from *Escherichia coli* or the homolog thereof comprises a sequence at least about 90% identical to SEQ ID NO:20.

12. The microorganism of claim 9 wherein the soluble pyridine nucleotide transhydrogenase from *Escherichia coli* or the homolog thereof comprises a sequence at least about 95% identical to SEQ ID NO:20.

13. The microorganism of claim 1 wherein the microorganism is a bacterium, the one or more recombinant nucleic acids is configured to express a soluble pyridine nucleotide transhydrogenase from *Escherichia coli* or a homolog thereof comprising a sequence at least about 95% identical to SEQ ID NO:20 and a lactate dehydrogenase selected from the group consisting of a lactate dehydrogenase from *Bacillus subtilis* or a homolog thereof comprising a sequence at least about 95% identical to SEQ ID NO:18 and a lactate dehydrogenase from *Lactococcus lactis* or a homolog thereof comprising a sequence at least about 95% identical to SEQ ID NO:22.

14. The microorganism of claim 13 wherein the microorganism is a cyanobacterium.

15. The microorganism of claim 14 wherein the lactase dehydrogenase comprises the lactate dehydrogenase from *Bacillus subtilis* or the homolog thereof comprising the sequence at least about 95% identical to SEQ ID NO:18.

16. The microorganism of claim 14 wherein the lactase dehydrogenase comprises the lactate dehydrogenase from *Lactococcus lactis* or the homolog thereof comprising the sequence at least about 95% identical to SEQ ID NO:18.

17. A method of producing lactic acid comprising culturing a microorganism as recited in claim 1.

18. The method of claim 17 wherein the culturing produces lactic acid to a concentration of at least about 5 mM.

19. The method of claim 17 wherein the culturing produces lactic acid at a rate of at least about 200 mg/L/Day.

20. The method of claim 17 wherein the culturing converts at least about 15% of carbon consumed by the microorganism to lactic acid.

* * * * *